(12) United States Patent
Gai et al.

(10) Patent No.: US 7,635,683 B2
(45) Date of Patent: Dec. 22, 2009

(54) QUINOXALINYL TRIPEPTIDE HEPATITIS C VIRUS INHIBITORS

(75) Inventors: Yonghua Gai, North Grafton, MA (US); Deqiang Niu, Lexington, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 13 days.

(21) Appl. No.: 11/499,917

(22) Filed: Aug. 4, 2006

(65) Prior Publication Data

US 2008/0032936 A1 Feb. 7, 2008

(51) Int. Cl.
*A61K 38/06* (2006.01)
(52) U.S. Cl. .......................... 514/18; 530/331
(58) Field of Classification Search .................. None
See application file for complete search history.

(56) References Cited

U.S. PATENT DOCUMENTS

| | | | |
|---|---|---|---|
| 6,323,180 | B1 | 11/2001 | Linas-Brunet et al. |
| 6,995,174 | B2 * | 2/2006 | Wang et al. ............... 514/312 |
| 7,132,504 | B2 | 11/2006 | Scola et al. |
| 7,135,462 | B2 | 11/2006 | Scola et al. |
| 7,176,208 | B2 | 2/2007 | Nakajima et al. |
| 2004/0106559 | A1 * | 6/2004 | Wang et al. ............... 514/18 |
| 2004/0266668 | A1 * | 12/2004 | Nakajima et al. ............ 514/9 |

OTHER PUBLICATIONS

R.C. Griffith et al., "HCV Anti-viral Agents", Annual Reports in Medicinal Chemistry, vol. 39, p. 223-237. (2004 Elsevier Inc.).
U.S. Appl. No. 11/489,011, filed Jul. 18, 2006, Nakajima et al.
U.S. Appl. No. 11/768,723, filed Jun. 26, 2007, Niu et al.
U.S. Appl. No. 11/768,712, filed Jun. 26, 2007, Niu et al.

* cited by examiner

*Primary Examiner*—Andrew D Kosar
(74) *Attorney, Agent, or Firm*—Carolyn S. Elmore; Edgar W. Harlan; Elmore Patent Law Group P.C.

(57) ABSTRACT

The present invention relates to compounds of Formula I, or a pharmaceutically acceptable salt, ester, or prodrug, thereof:

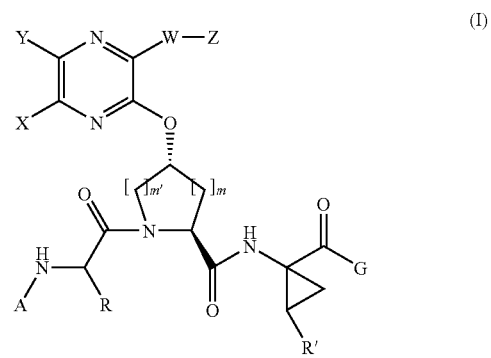

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

5 Claims, No Drawings

QUINOXALINYL TRIPEPTIDE HEPATITIS C VIRUS INHIBITORS

TECHNICAL FIELD

The present invention relates to novel tripeptides having activity against the hepatitis C virus (HCV) and useful in the treatment of HCV infections. More particularly, the invention relates to tripeptide compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug would desirably possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3.4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov. 1, 867-881 (2002). Other patent disclosures describing the synthesis of HCV protease inhibitors are: US 2005/0261200; WO 03/099274 (2003); US 2003/0008828; US2002/0037998 (2002); WO 00/59929 (2000); WO 00/09543 (2000); WO 99/50230 (1999); U.S. Pat. No. 5,861,297 (1999); WO 99/07733 (1999).

SUMMARY OF THE INVENTION

The present invention relates to novel tripeptide compounds and methods of treating a hepatitis C infection in a subject in need of such therapy with said tripeptide compounds. The present invention further relates to pharmaceutical compositions comprising the compounds of the present invention, or pharmaceutically acceptable salts, esters, or prodrugs thereof, in combination with a pharmaceutically acceptable carrier or excipient.

In one embodiment of the present invention there are disclosed compounds represented by Formulas I, or pharmaceutically acceptable salts, esters, or prodrugs thereof:

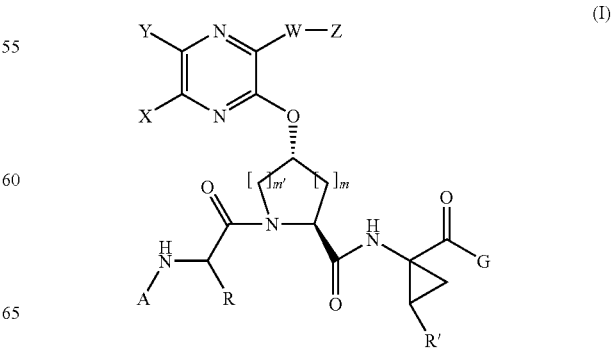

Wherein

A is selected from —C(=O)—O—$R_1$, —C(=O)—$R_2$, —C(=O)—NH—$R_2$, or —S(O)$_2$—$R_1$, —S(O)$_2$NH$R_2$;

$R_1$ is selected from the group consisting of:
(i) aryl; substituted aryl; heteroaryl; substituted heteroaryl;
(ii) heterocycloalkyl or substituted heterocycloalkyl;
(iii) —$C_1$-$C_8$ alkyl, —$C_2$-$C_8$ alkenyl, or —$C_2$-$C_8$ alkynyl containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

$R_2$ is independently selected from the group consisting of:
(i) hydrogen;
(ii) aryl; substituted aryl; heteroaryl; substituted heteroaryl;
(iii) heterocycloalkyl or substituted heterocycloalkyl;
(iv) —$C_1$-$C_8$ alkyl, —$C_2$-$C_8$ alkenyl, or —$C_2$-$C_8$ alkynyl containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

R and R' are independently selected from the group consisting of:
(i) —$C_1$-$C_8$ alkyl, —$C_2$-$C_8$ alkenyl, or —$C_2$-$C_8$ alkynyl containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_4$-$C_{12}$ alkylcycloalkyl, or substituted —$C_4$-$C_{12}$ alkylcycloalkyl; —$C_3$-$C_{12}$ cycloalkenyl, or substituted —$C_3$-$C_{12}$ cycloalkenyl; —$C_4$-$C_{12}$ alkylcycloalkenyl, or substituted —$C_4$-$C_{12}$ alkylcycloalkenyl;
(ii) aryl; substituted aryl; heteroaryl; substituted heteroaryl;
(iii) heterocycloalkyl or substituted heterocycloalkyl;
(iv) hydrogen; deuterium;

G is selected from —OH, —NHS(O)$_2$—$R_3$, —NH(SO$_2$)N$R_4R_5$;

$R_3$ is selected from:
(i) aryl; substituted aryl; heteroaryl; substituted heteroaryl
(ii) heterocycloalkyl or substituted heterocycloalkyl;
(iii) —$C_1$-$C_8$ alkyl, —$C_2$-$C_8$ alkenyl, or —$C_2$-$C_8$ alkynyl containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

$R_4$ and $R_5$ are independently selected from:
(i) hydrogen;
(ii) aryl; substituted aryl; heteroaryl; substituted heteroaryl;
(iii) heterocycloalkyl or substituted heterocycloalkyl;
(iv) —$C_1$-$C_8$ alkyl, —$C_2$-$C_8$ alkenyl, or —$C_2$-$C_8$ alkynyl containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

X and Y taken together with the carbon atoms to which they are attached to form a cyclic moiety which selected from aryl, substituted aryl, heteroaryl, or substituted heteroaryl;

W is absent, or selected from —O—, —S—, —NH—, —N(Me)—, —C(O)NH—, or —C(O)N(Me)—;

Z is selected from the groups consisting of:
(i) hydrogen;
(ii) aryl, substituted aryl;
(iii) heteroaryl, substituted heteroaryl;
(iv) —$C_3$-$C_{12}$ cycloalkyl, substituted —$C_3$-$C_{12}$ cycloalkyl, heterocycloalkyl, substituted heterocycloalkyl;
(v) —$C_1$-$C_6$ alkyl containing 0, 1, 2, or 3 heteroatoms selected from O, S, or N, optionally substituted with one or more substituent selected from halogen, aryl, substituted aryl, heteroaryl, or substituted heteroaryl;
(vi) —$C_2$-$C_6$ alkenyl containing 0, 1, 2, or 3 heteroatoms selected from O, S, or N, optionally substituted with one or more substituent selected from halogen, aryl, substituted aryl, heteroaryl, or substituted heteroaryl;
(vii) —$C_2$-$C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;
W-Z taken together, is —CN, —$N_3$, halogen, —NH—N=CH($R_2$), where $R_2$ is as previously defined.

m=0, 1, or 2;
m'=1 or 2

DETAILED DESCRIPTION OF THE INVENTION

A first embodiment of the invention is a compound represented by Formula I as described above, or a pharmaceutically acceptable salt, ester or prodrug thereof, alone or in combination with a pharmaceutically acceptable carrier or excipient.

A second embodiment of the invention is a compound represented by Formula II as described above, or a pharmaceutically acceptable salt, ester or prodrug thereof, alone or in combination with a pharmaceutically acceptable carrier or excipient.

Representative subgenera of the invention include, but are not limited to:

A compound of Formula II:

(II)

where $X_1$-$X_4$ are independently selected from —$CR_6$ and N, wherein $R_6$ is independently selected from:

(i) hydrogen; halogen; —$NO_2$; —CN;

(ii) -M-$R_4$, M is O, S, NH, where $R_4$ is as previously defined.

(iii) $NR_4R_5$, where $R_4$ and $R_5$ are as previously defined.

(iv) —$C_1$-$C_8$ alkyl, —$C_2$-$C_8$ alkenyl, or —$C_2$-$C_8$ alkynyl containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

(v) aryl; substituted aryl; heteroaryl; substituted heteroaryl;

(vi) heterocycloalkyl or substituted heterocycloalkyl;

where A, G, W, Z are as previously defined.

A compound of Formula III:

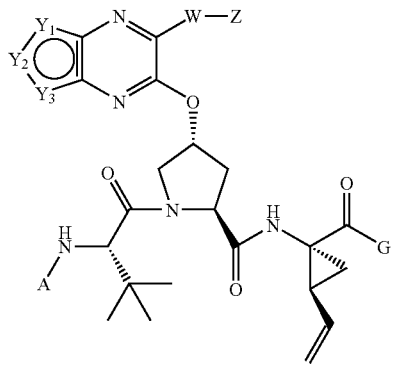

(III)

where $Y_1$-$Y_3$ are independently selected from $CR_6$, N, $NR_6$, S and O; where $R_6$, A, G, W, Z are as previously defined.

Representative compounds of the invention include, but are not limited to, the following compounds (table 1) according to Formula IV:

TABLE 1

(IV)

| Example# | A | Q | G |
|---|---|---|---|
| 1 | [tert-butyl ester group] | [quinoxaline-thiophene group] | —OH |
| 2 | [tert-butyl ester group] | [quinoxaline-thiophene group] | [cyclopropylsulfonamide group] |
| 3 | H | [quinoxaline-thiophene group] | [cyclopropylsulfonamide group] |

TABLE 1-continued
(IV)
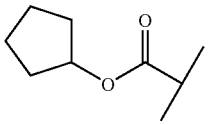
| Example# | A | Q | G |
|---|---|---|---|
| 4 | 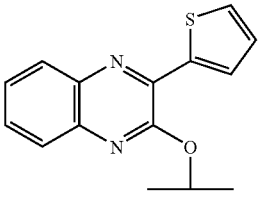 | 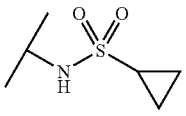 | 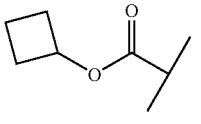 |
| 5 | 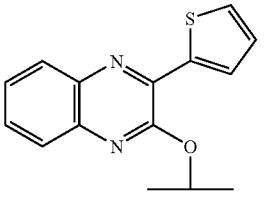 | 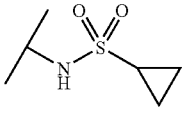 | 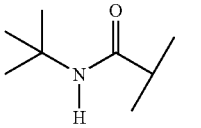 |
| 6 | 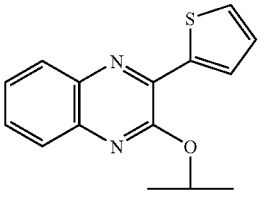 | 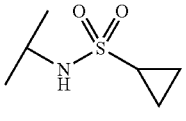 | 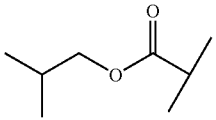 |
| 7 | 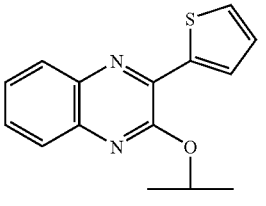 | 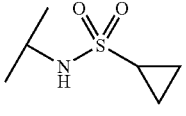 | 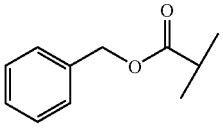 |
| 8 | 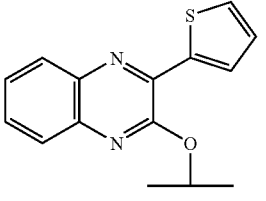 | 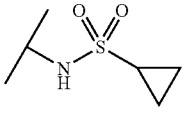 | 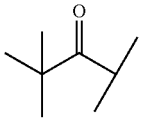 |
| 9 | 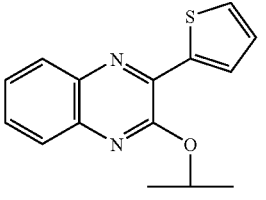 | 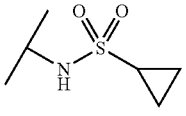 | |

TABLE 1-continued (IV)

| Example# | A | Q | G |
|---|---|---|---|
| 10 | 3-fluorophenyl ethylsulfonyl | 3-thiophen-2-yl-quinoxalin-2-yloxy (isopropoxy) | N-cyclopropylsulfonyl isopropylamide |
| 11 | cyclopropylsulfonyl ethyl | 3-thiophen-2-yl-quinoxalin-2-yloxy (isopropoxy) | N-cyclopropylsulfonyl isopropylamide |
| 12 | tetrahydropyran-4-yl isobutyrate | 3-thiophen-2-yl-quinoxalin-2-yloxy (isopropoxy) | N-cyclopropylsulfonyl isopropylamide |
| 13 | tert-butyl isobutyrate | 5,8-dimethoxy-3-thiophen-2-yl-quinoxalin-2-yloxy (isopropoxy) | —OH |
| 14 | tert-butyl isobutyrate | 3-(5-chlorothiophen-2-yl)-quinoxalin-2-yloxy (isopropoxy) | —OH |
| 15 | tert-butyl isobutyrate | 3-(2-pyridin-3-yl-vinyl)-quinoxalin-2-yloxy (isopropoxy) | —OH |

TABLE 1-continued
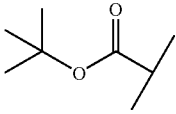
(IV)
| Example# | A | Q | G |
|---|---|---|---|
| 16 | 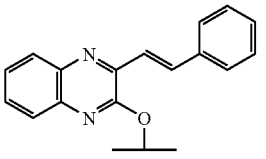 | 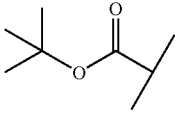 | —OH |
| 17 | 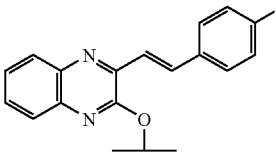 | 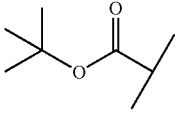 | —OH |
| 18 | 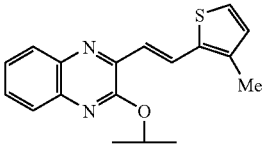 | 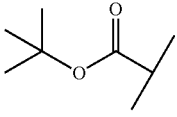 | —OH |
| 19 | 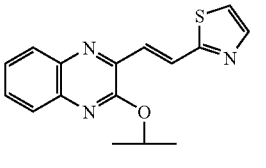 | 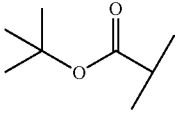 | —OH |
| 20 | 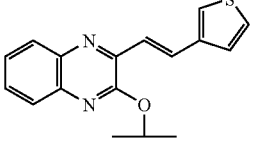 | 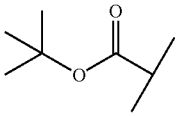 | —OH |
| 21 | 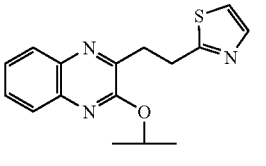 | 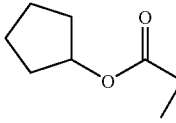 | —OH |
| 22 | 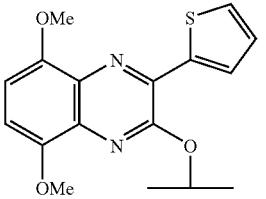 | | —OH |

TABLE 1-continued

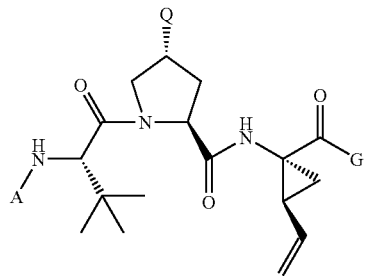

(IV)

| Example# | A | Q | G |
|---|---|---|---|
| 23 | cyclopentyl isobutyrate ester | 6,7-dichloro-3-(thiophen-2-yl)quinoxalin-2-yloxy | —OH |
| 24 | cyclopentyl isobutyrate ester | 6-methoxy-3-(thiophen-2-yl)quinoxalin-2-yloxy | —OH |
| 25 | cyclopentyl isobutyrate ester | 7-methoxy-3-(thiophen-2-yl)quinoxalin-2-yloxy | —OH |
| 26 | cyclopentyl isobutyrate ester | 6,7-dimethoxy-3-(thiophen-2-yl)quinoxalin-2-yloxy | —OH |
| 27 | cyclopentyl isobutyrate ester | 3-(5-vinylthiophen-2-yl)quinoxalin-2-yloxy | —OH |
| 28 | cyclopentyl isobutyrate ester | 3-(5-bromothiophen-2-yl)quinoxalin-2-yloxy | —OH |

TABLE 1-continued (IV)

| Example# | A | Q | G |
|---|---|---|---|
| 29 | cyclopentyl isobutyrate ester | 2-(5-chlorothiophen-2-yl)-3-alkoxyquinoxaline | —OH |
| 30 | cyclopentyl isobutyrate ester | 2-(2-(thiazol-2-yl)ethyl)-3-alkoxyquinoxaline | —OH |
| 31 | cyclopentyl isobutyrate ester | 2-((thiophen-2-ylthio)methyl)-3-alkoxyquinoxaline | —OH |
| 32 | cyclopentyl isobutyrate ester | 2-(2-(thiophen-2-yl)ethyl)-3-alkoxyquinoxaline | —OH |
| 33 | 2-fluoroethyl isobutyrate ester | 2-(thiophen-2-yl)-3-alkoxyquinoxaline | —OH |
| 34 | cyclobutyl isobutyrate ester | 2-(thiophen-2-yl)-3-alkoxyquinoxaline | —OH |

TABLE 1-continued (IV)

| Example# | A | Q | G |
|---|---|---|---|
| 35 | cyclohexyl isobutyrate ester | 3-(thiophen-2-yl)quinoxalin-2-yloxy | —OH |
| 36 | 1-(thiophen-2-yl)propan-1-one | 3-(thiophen-2-yl)quinoxalin-2-yloxy | —OH |
| 37 | 1-phenylpropan-1-one | 3-(thiophen-2-yl)quinoxalin-2-yloxy | —OH |
| 38 | 1-(1H-pyrrol-2-yl)propan-1-one | 3-(thiophen-2-yl)quinoxalin-2-yloxy | —OH |
| 39 | 1-(1-methyl-1H-pyrrol-2-yl)propan-1-one | 3-(thiophen-2-yl)quinoxalin-2-yloxy | —OH |
| 40 | 1-(furan-3-yl)propan-1-one | 3-(thiophen-2-yl)quinoxalin-2-yloxy | —OH |

TABLE 1-continued (IV)

| Example# | A | Q | G |
|---|---|---|---|
| 41 | 2,5-dimethyl-1H-pyrrol-3-yl isopropyl ketone | 3-(thiophen-2-yl)quinoxalin-2-yloxy isopropyl | —OH |
| 42 | 1-ethyl-3-methyl-1H-pyrazol-5-yl isopropyl ketone | 3-(thiophen-2-yl)quinoxalin-2-yloxy isopropyl | —OH |
| 43 | 1H-pyrazol-4-yl isopropyl ketone | 3-(thiophen-2-yl)quinoxalin-2-yloxy isopropyl | —OH |
| 44 | furan-2-yl isopropyl ketone | 3-(thiophen-2-yl)quinoxalin-2-yloxy isopropyl | —OH |
| 45 | 1H-pyrazol-5-yl isopropyl ketone | 3-(thiophen-2-yl)quinoxalin-2-yloxy isopropyl | —OH |
| 46 | thiophen-2-yl isopropyl ketone | 3-(2-(thiophen-2-yl)vinyl)quinoxalin-2-yloxy isopropyl | —OH |

TABLE 1-continued
(IV)
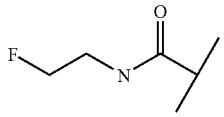
| Example# | A | Q | G |
|---|---|---|---|
| 47 | 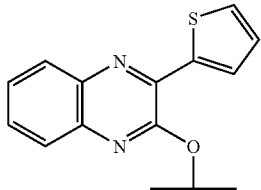 |  | —OH |
| 48 | 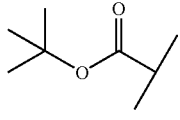 | 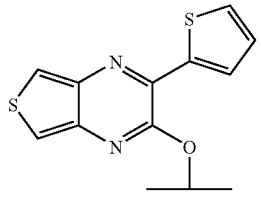 | —OH |
| 49 |  | 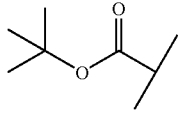 | 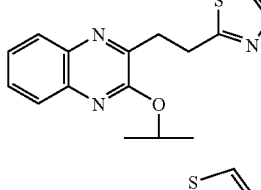 |
| 50 | 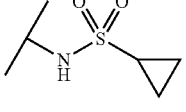 | 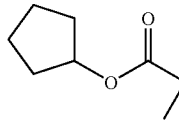 | 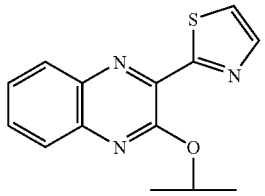 |
| 51 | 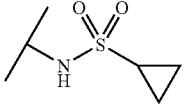 | 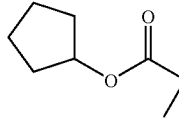 | 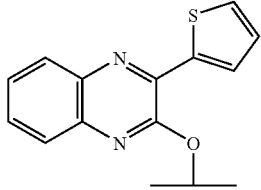 |
| 52 | 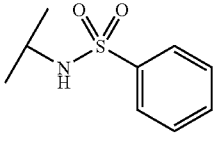 | 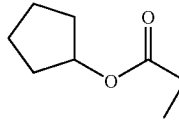 | 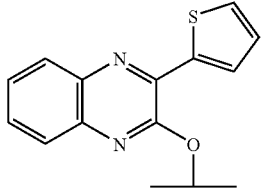 |

TABLE 1-continued (IV)

| Example# | A | Q | G |
|---|---|---|---|
| 53 | cyclopentyl-O-C(=O)-CH(CH3)- | 3-(thiophen-2-yl)-2-(isopropoxy)quinoxalinyl | -NH-SO2-morpholinyl |
| 54 | cyclopentyl-O-C(=O)-CH(CH3)- | 3-(thiophen-2-yl)-2-(isopropoxy)quinoxalinyl | -NH-SO2-(4-methylpiperazinyl) |
| 55 | cyclopentyl-O-C(=O)-CH(CH3)- | 3-(thiophen-2-yl)-2-(isopropoxy)quinoxalinyl | -NH-SO2-C6H4-NHC(=O)CH3 |
| 56 | cyclopentyl-O-C(=O)-CH(CH3)- | 3-(thiophen-2-yl)-2-(isopropoxy)quinoxalinyl | -NH-SO2-(thiophen-2-yl) |
| 57 | cyclopentyl-O-C(=O)-CH(CH3)- | 3-(thiophen-2-yl)-2-(isopropoxy)quinoxalinyl | -NH-SO2-C6H4-CH3 |
| 58 | cyclopentyl-O-C(=O)-CH(CH3)- | 3-(thiophen-2-yl)-2-(isopropoxy)quinoxalinyl | -NH-SO2-C6H4-CO2H |

TABLE 1-continued

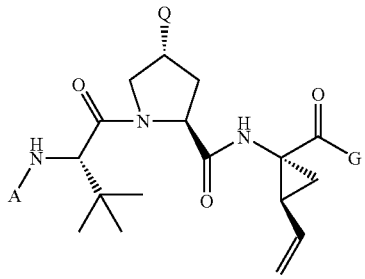
(IV)

| Example# | A | Q | G |
|---|---|---|---|
| 59 | cyclopentyl 2-methylpropanoate | 3-(thiophen-2-yl)-2-(propan-2-yloxy)quinoxaline | N-(4-methoxyphenyl)sulfonamide |
| 60 | cyclopentyl 2-methylpropanoate | 3-(thiophen-2-yl)-2-(propan-2-yloxy)quinoxaline | N-(5-methylpyridin-2-yl)sulfonamide |
| 61 | cyclopentyl 2-methylpropanoate | 3-(thiophen-2-yl)-2-(propan-2-yloxy)quinoxaline | N-(4-chloropyridin-3-yl)sulfonamide |
| 62 | cyclopentyl 2-methylpropanoate | 3-(2-(thiazol-2-yl)ethyl)-2-(propan-2-yloxy)quinoxaline | N-cyclopropylsulfonamide |
| 63 | cyclopentyl 2-methylpropanoate | 3-(5-chlorothiophen-2-yl)-2-(propan-2-yloxy)quinoxaline | N-cyclopropylsulfonamide |
| 64 | cyclopentyl 2-methylpropanoate | 6,7-dimethoxy-3-(thiophen-2-yl)-2-(propan-2-yloxy)quinoxaline | N-cyclopropylsulfonamide |

TABLE 1-continued
(IV)
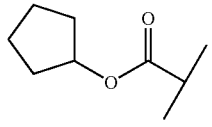
| Example# | A | Q | G |
|---|---|---|---|
| 65 | 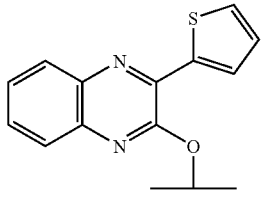 | 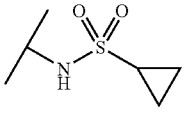 | 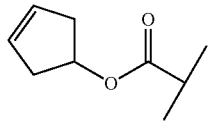 |
| 66 | 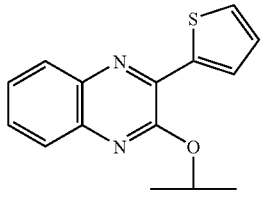 | 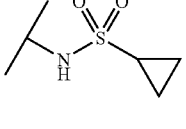 | 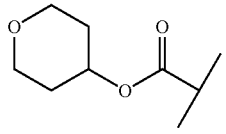 |
| 67 | 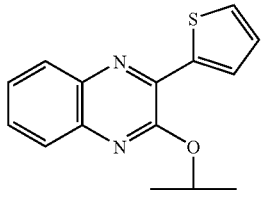 | 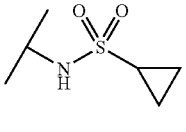 | 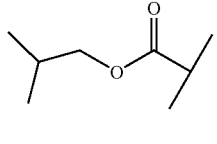 |
| 68 | 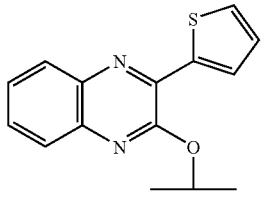 | 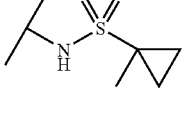 | 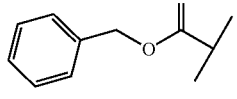 |
|  | 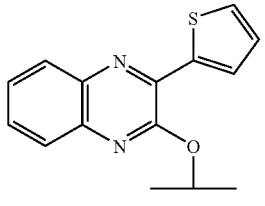 |  |  |
| 69 | 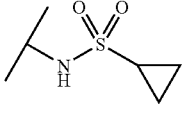 | | |

TABLE 1-continued
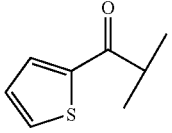
(IV)
| Example# | A | Q | G |
|---|---|---|---|
| 70 | | | |
| 71 | | | |
| 72 | | | |
| 73 | | | |
| 74 | | | |
| 75 | | | |

TABLE 1-continued
(IV)
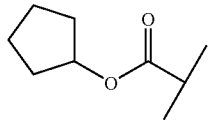
| Example# | A | Q | G |
|---|---|---|---|
| 76 | 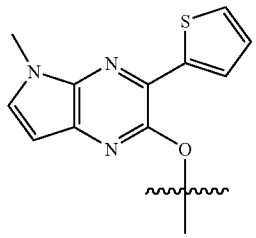 | 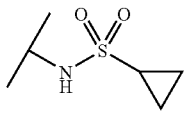 | 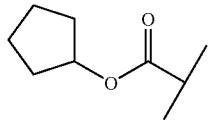 |
| 77 | 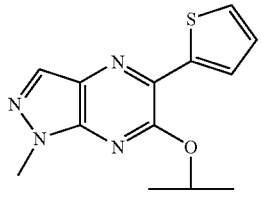 | 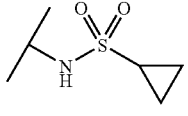 | 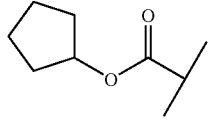 |
| 78 | 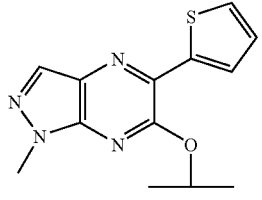 | 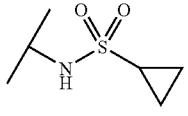 | 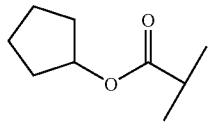 |
| 79 | 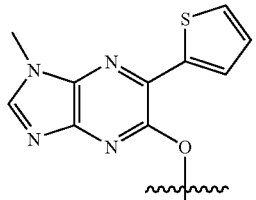 | 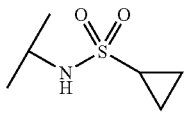 | 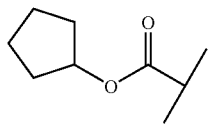 |
| 80 | 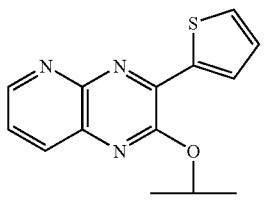 | 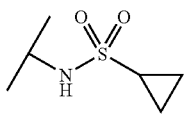 | |

TABLE 1-continued
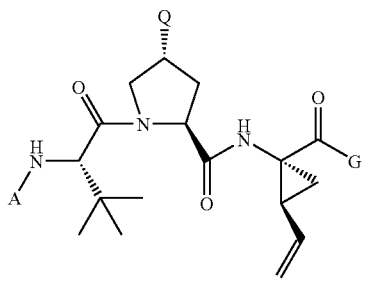
| Example# | A | Q | G |
|---|---|---|---|
| 81 | | | |
| 82 | | | |
| 83 | | | |
| 84 | | | |
| 85 | | | |
| 86 | | | |
| 87 | | | |

TABLE 1-continued (IV)

| Example# | A | Q | G |
|---|---|---|---|
| 88 | ethyl ester | 3-(thiophen-2-yl)quinoxalin-2-yloxy | N-cyclopropylsulfonyl |
| 89 | propyl ester | 3-(thiophen-2-yl)quinoxalin-2-yloxy | N-cyclopropylsulfonyl |
| 90 | isopropyl ester | 3-(thiophen-2-yl)quinoxalin-2-yloxy | N-cyclopropylsulfonyl |
| 91 | cyclopropyl ester | 3-(thiophen-2-yl)quinoxalin-2-yloxy | N-cyclopropylsulfonyl |
| 92 | isobutyl ester | 3-(thiophen-2-yl)quinoxalin-2-yloxy | N-cyclopropylsulfonyl |
| 93 | 2-fluoroethyl ester | 3-(thiophen-2-yl)quinoxalin-2-yloxy | N-cyclopropylsulfonyl |

TABLE 1-continued
(IV)
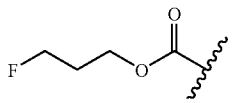
| Example# | A | Q | G |
|---|---|---|---|
| 94 | 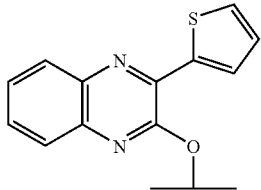 | 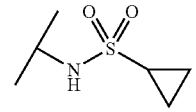 | 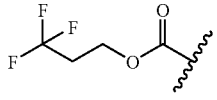 |
| 95 | 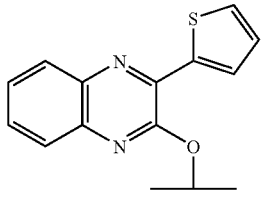 | 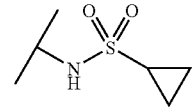 | 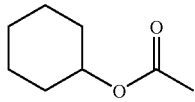 |
| 96 | 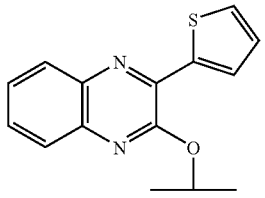 | 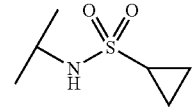 | 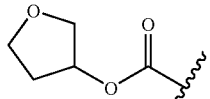 |
| 97 | 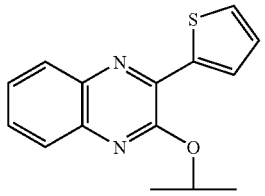 | 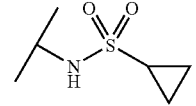 | 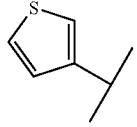 |
| 98 | 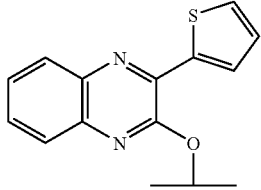 | 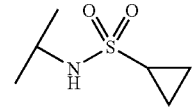 | 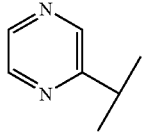 |
| 99 | 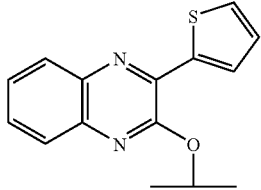 | 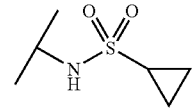 | |

TABLE 1-continued
(IV)
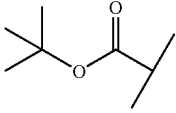
| Example# | A | Q | G |
|---|---|---|---|
| 100 | 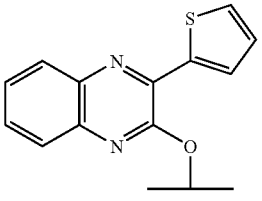 | 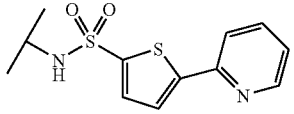 | 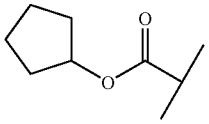 |
| 101 | 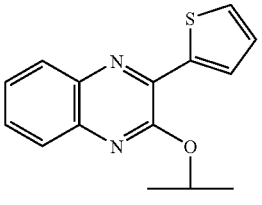 | 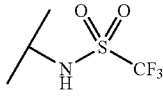 | 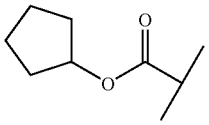 |
| 102 | 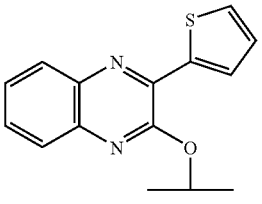 | 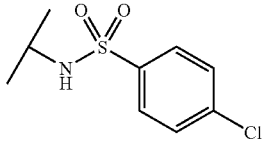 | 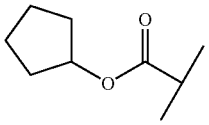 |
| 103 | 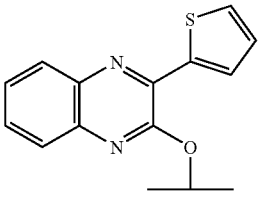 | 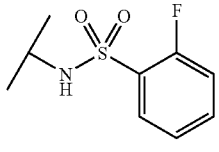 | 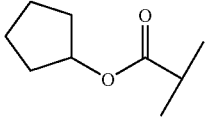 |
| 104 | 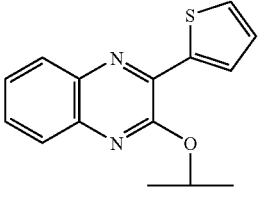 | 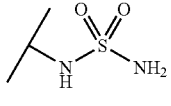 | 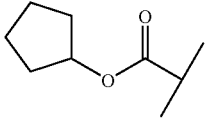 |
| 105 | 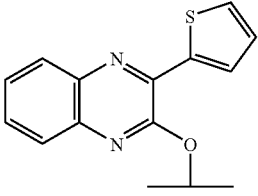 | 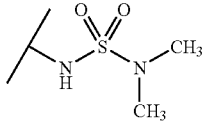 | |

US 7,635,683 B2
TABLE 1-continued
(IV)
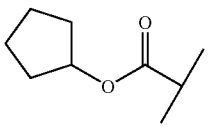
| Example# | A | Q | G |
|---|---|---|---|
| 106 | 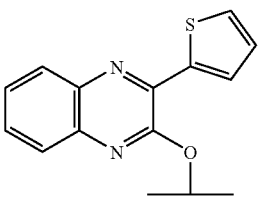 | 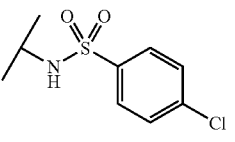 | 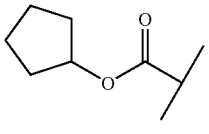 |
| 107 | 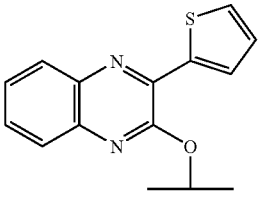 | 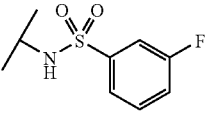 | 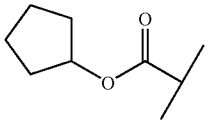 |
| 108 | 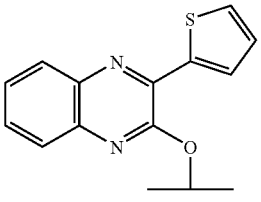 | 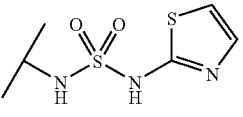 | 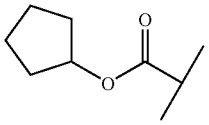 |
| 109 | 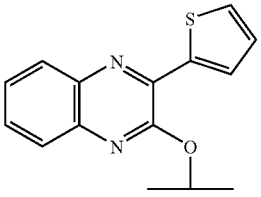 | 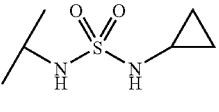 | 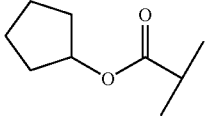 |
| 110 | 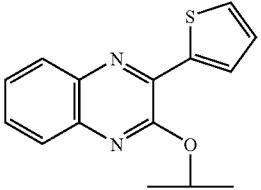 | 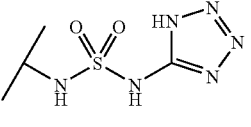 | 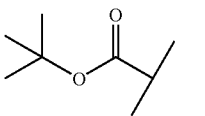 |
| 111 | 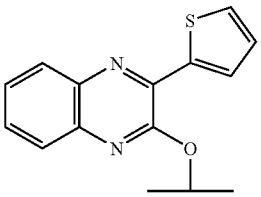 | 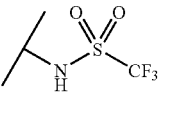 | |

TABLE 1-continued
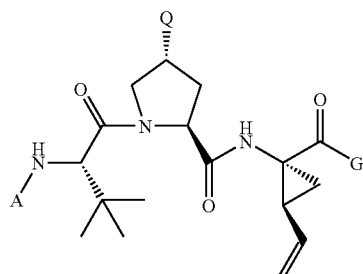
(IV)
| Example# | A | Q | G |
|---|---|---|---|
| 112 | 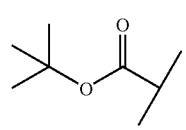 | 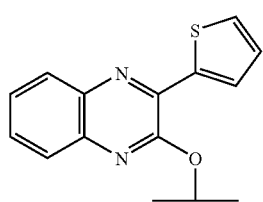 | 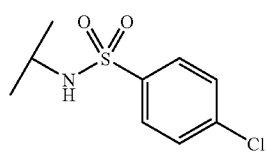 |
| 113 | 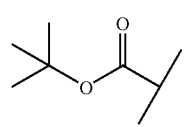 | 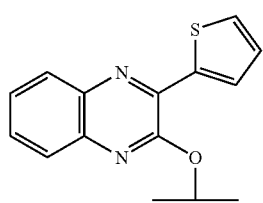 | 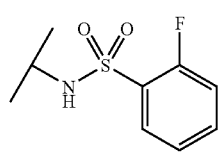 |
| 114 | 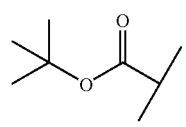 | 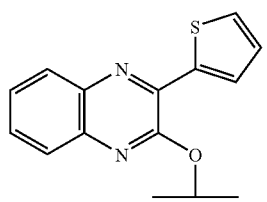 | 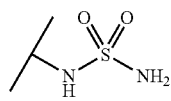 |
| 115 | 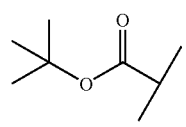 | 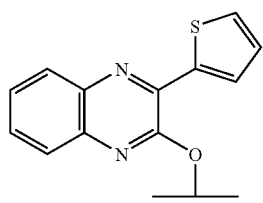 | 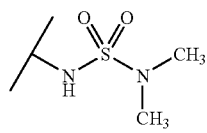 |
| 116 | 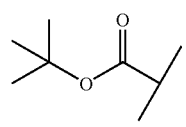 | 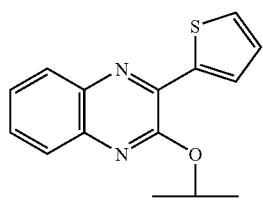 | 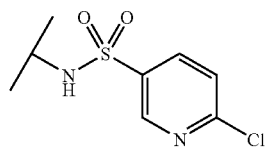 |

TABLE 1-continued
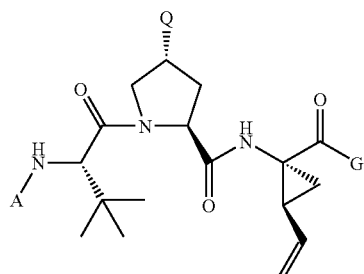
(IV)
| Example# | A | Q | G |
|---|---|---|---|
| 117 | 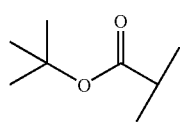 | 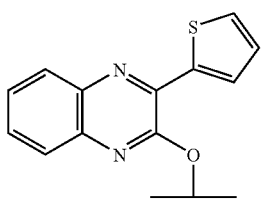 | 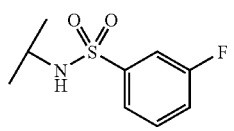 |
| 118 | 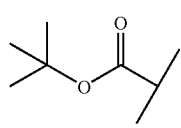 | 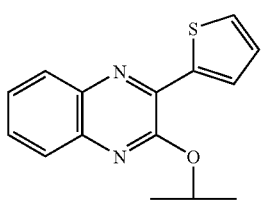 | 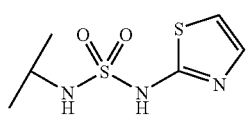 |
| 119 | 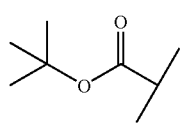 | 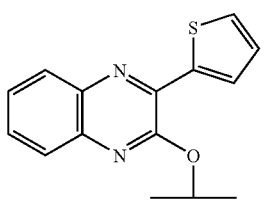 | 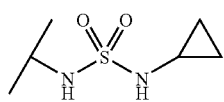 |
| 120 | 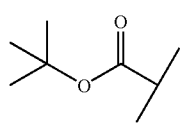 | 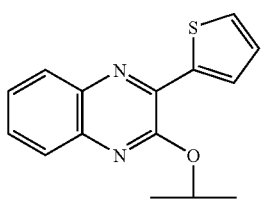 | 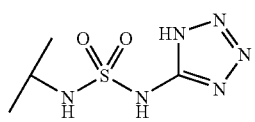 |
| 121 | 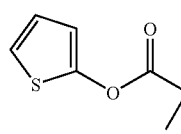 | 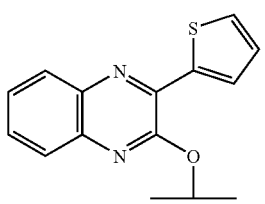 | 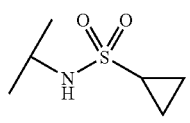 |

TABLE 1-continued
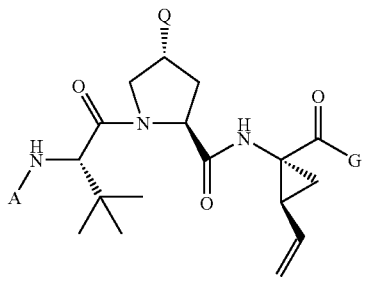
(IV)
| Example# | A | Q | G |
|---|---|---|---|
| 122 | 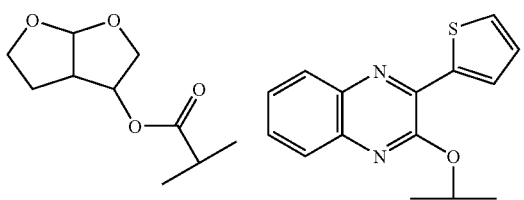 | 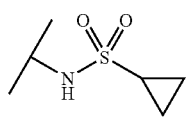 | |
| 123 | 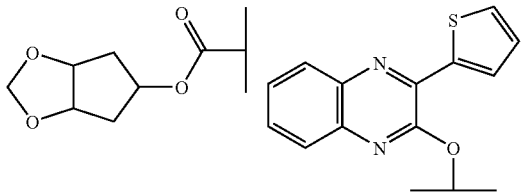 | 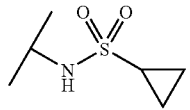 | |
| 124 | 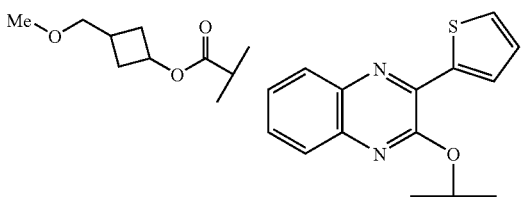 | 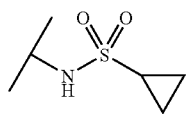 | |
| 125 | 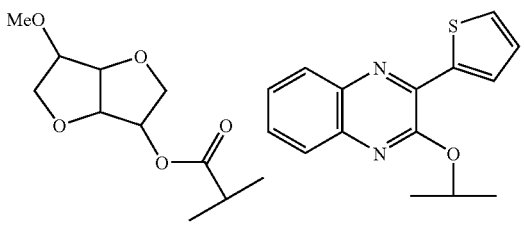 | 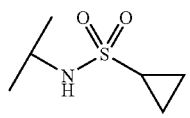 | |
| 126 | 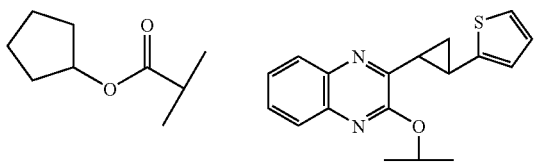 | 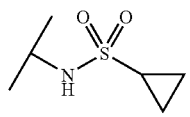 | |

TABLE 1-continued
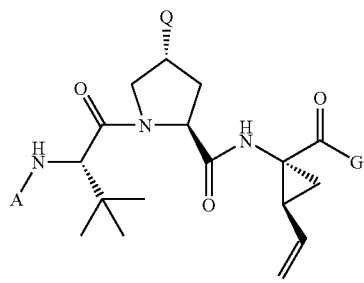
(IV)
| Example# | A | Q | G |
|---|---|---|---|
| 127 | 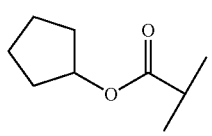 | 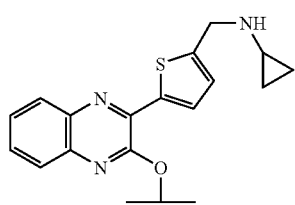 | 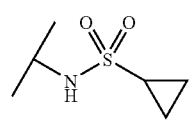 |
| 128 | 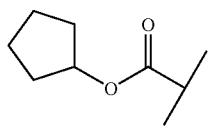 | 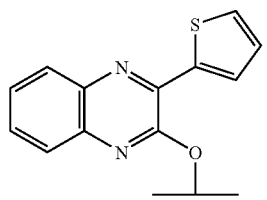 | 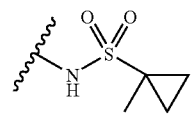 |
| 129 | 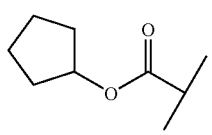 | 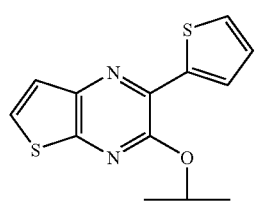 | 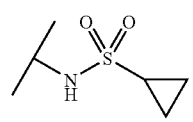 |

Additional compounds of the invention are those of Formula IV:

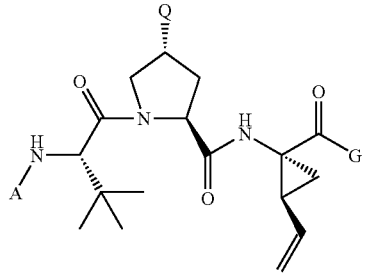

, wherein A, Q and G are as defined in the A-Matrix, Q-Matrix and G-Matrix tables herein (Tables 2-4). The A-Matrix, Q-Matrix and G-Matrix tables below set forth substituents present on the core ring structure shown in formula (IV) which when one A substituent is selected from the A-Matrix, one Q substituent is selected from the Q-Matrix and one G substituent is selected from the G-Matrix, an additional compound of the invention is described. Compounds are formed by selecting any element from the A-Matrix with any element from the Q-matrix with any element from the G-matrix to arrive upon an A, Q, G-substituted macrocycle of formula IV. For example, a compound of Formula IV, wherein A is element A01 from the A-Matrix, Q is element Q01 from the Q-Matrix, and G is element G02 from the G-Matrix is designated by the number A01Q01G02.

Thus, the invention includes compounds of the formula IV and the pharmaceutically acceptable salts thereof, wherein A is any element in the A-Matrix, Q is any element of the Q-Matrix and G is any element of the G-Matrix.

Specific compounds include, but are not limited to, the following:

A01Q01G02; A01Q02G02; A01Q03G02; A01Q38G02; A01Q48G02; A01Q49G02; A01Q61G02; A05Q01G03; A01Q02G03; A05Q03G05; A09Q38G02; A30Q48G02; A01Q49G03; A05Q01G20; A05Q01G24; A05Q01G05; A05Q61G11; A05Q01G11; A30Q01G11; A05Q38G24; A05Q38G02; A05Q49G05; A30Q02G03; A09Q01G02; A09Q02G02; A09Q03G02; A095Q38G02; A09Q48G02; A09Q61G03; A30Q03G02; A30Q03G03; A30Q05G09; A30Q61G02; A05Q03G09; A05Q03G09; A01Q38G02; A01Q49G24; A05Q61G20; A09Q38G20; A30Q48G24; A30Q48G20; A30Q49G24; A05Q38G09; A05Q17G09; A05Q09G09; A05Q04G09; A05Q08G11; A05Q01G06; A05Q16G02; A05Q17G02; A05Q25G02; A03Q01G02; A06Q01G02; A16Q01G02.

TABLE 2

A-Matrix

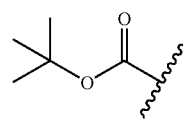

A-01

TABLE 2-continued

A-Matrix

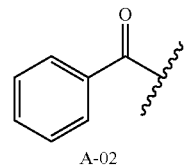

A-02

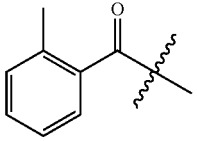

A-03

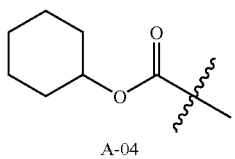

A-04

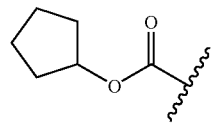

A-05

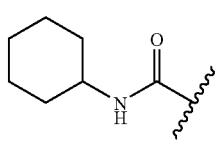

A-06

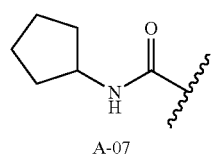

A-07

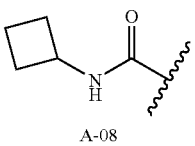

A-08

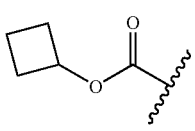

A-09

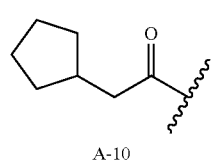

A-10

TABLE 2-continued
A-Matrix
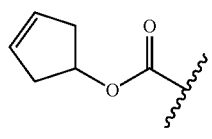
A-11
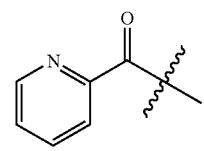
A-12
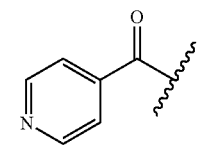
A-13
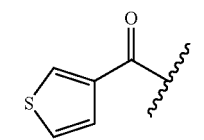
A-14
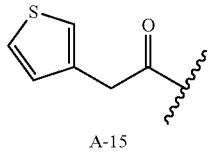
A-15
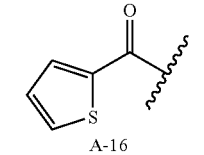
A-16
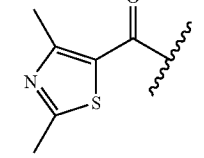
A-17
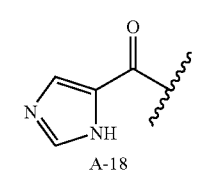
A-18
TABLE 2-continued
A-Matrix
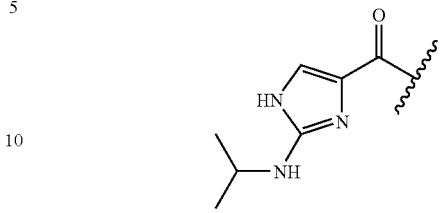
A-19
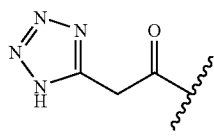
A-20
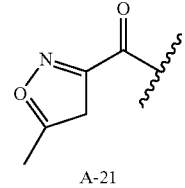
A-21
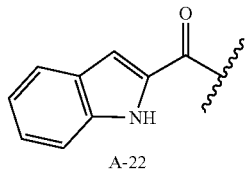
A-22
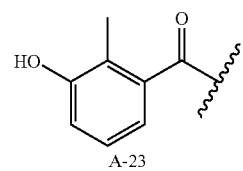
A-23
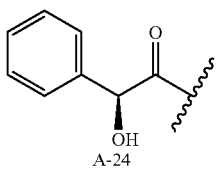
A-24
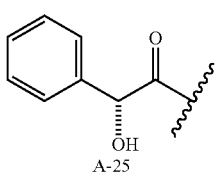
A-25
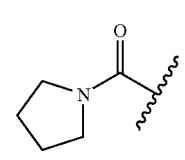
A-26

TABLE 2-continued
A-Matrix
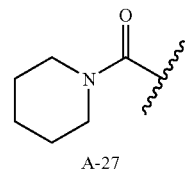
A-27
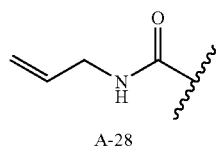
A-28
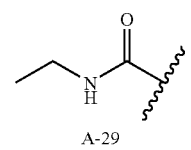
A-29
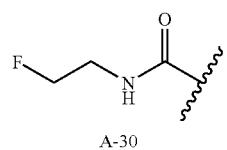
A-30
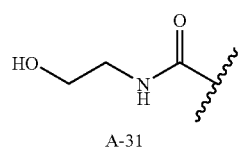
A-31
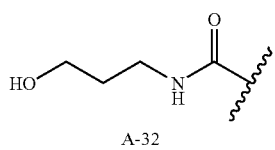
A-32
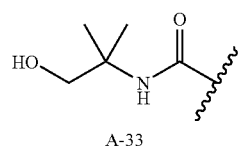
A-33
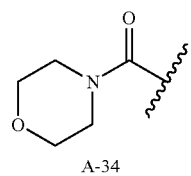
A-34
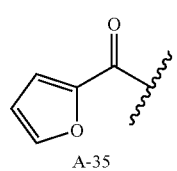
A-35
TABLE 2-continued
A-Matrix
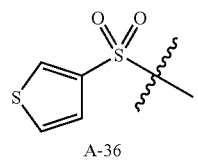
A-36
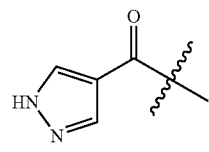
A-37
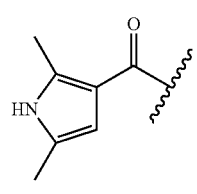
A-38
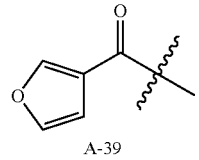
A-39
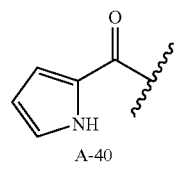
A-40
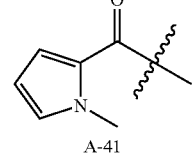
A-41
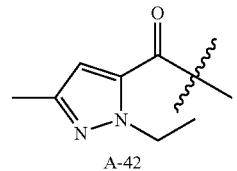
A-42
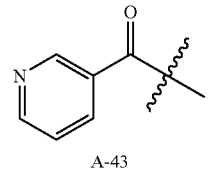
A-43

TABLE 2-continued
A-Matrix
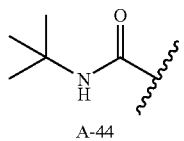
A-44
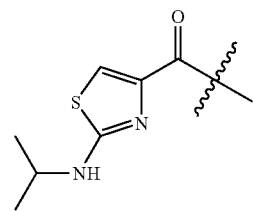
A-45
TABLE 3
Q-Matrix
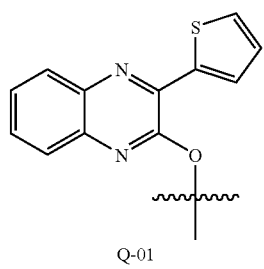
Q-01
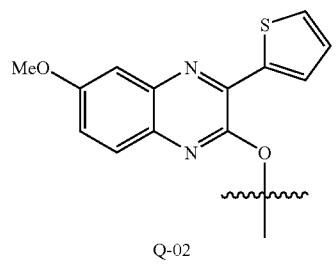
Q-02
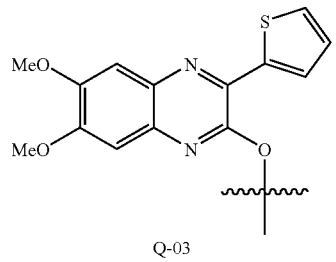
Q-03
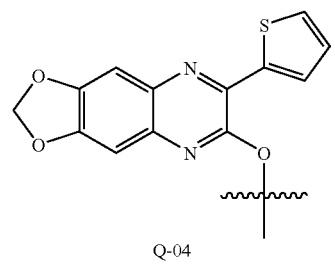
Q-04
TABLE 3-continued
Q-Matrix
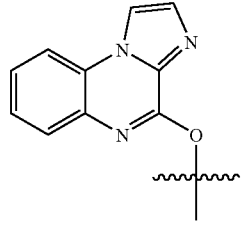
Q-05
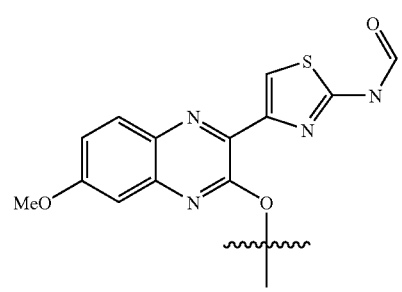
Q-06
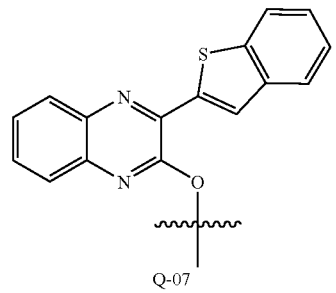
Q-07
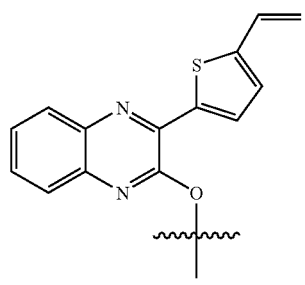
Q-08
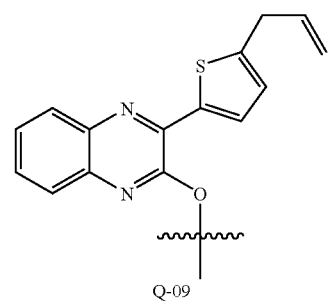
Q-09

TABLE 3-continued
Q-Matrix
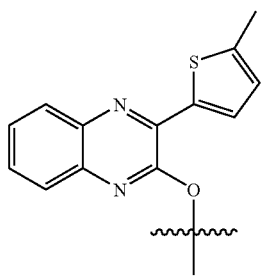
Q-10
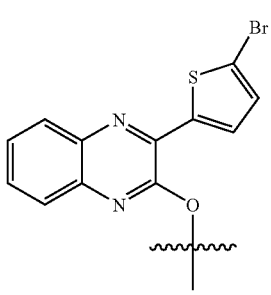
Q-11
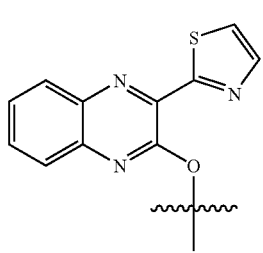
Q-12
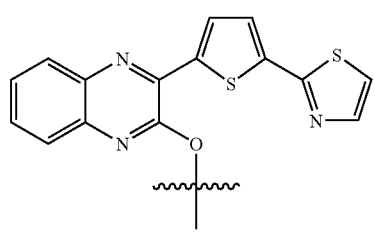
Q-13
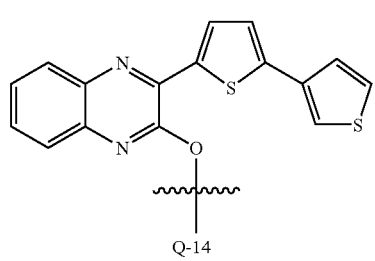
Q-14
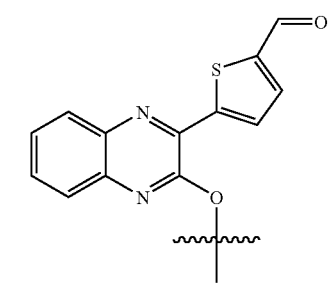
Q-15
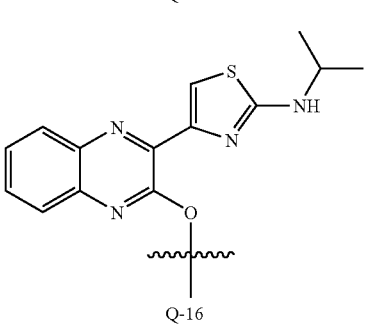
Q-16
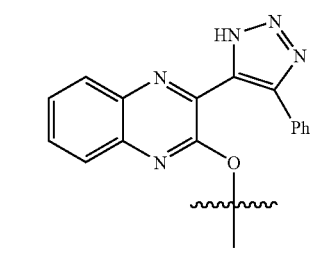
Q-17
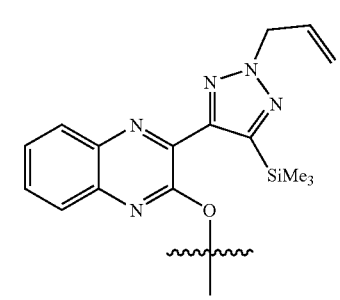
Q-18
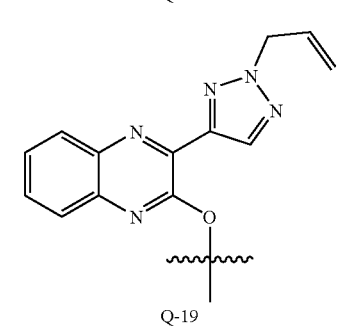
Q-19

TABLE 3-continued
Q-Matrix
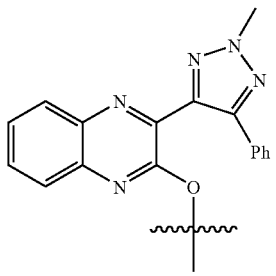
Q-20
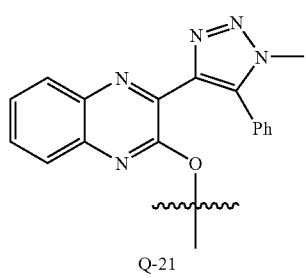
Q-21
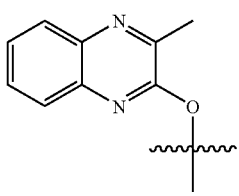
Q-22
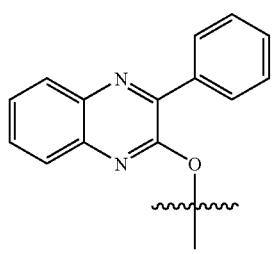
Q-23
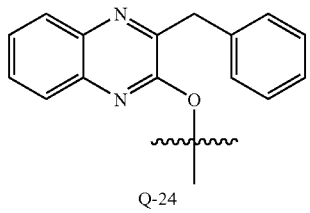
Q-24
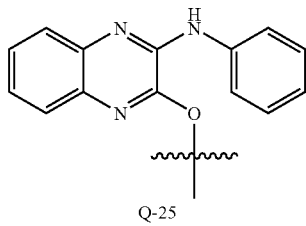
Q-25
TABLE 3-continued
Q-Matrix
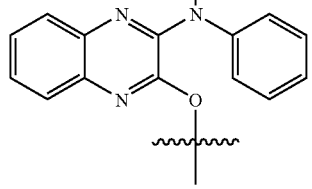
Q-26
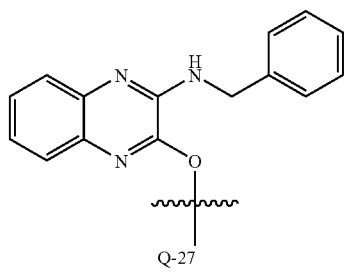
Q-27
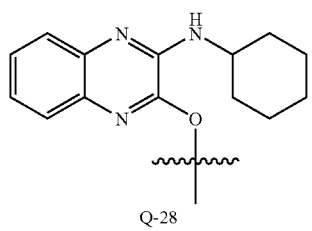
Q-28
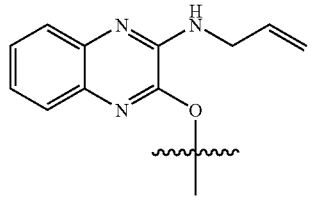
Q-29
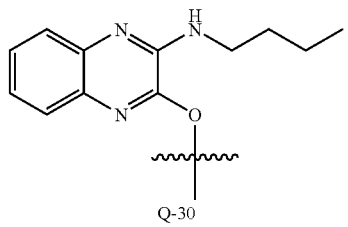
Q-30
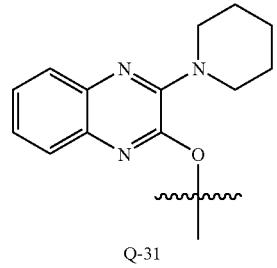
Q-31

TABLE 3-continued
Q-Matrix
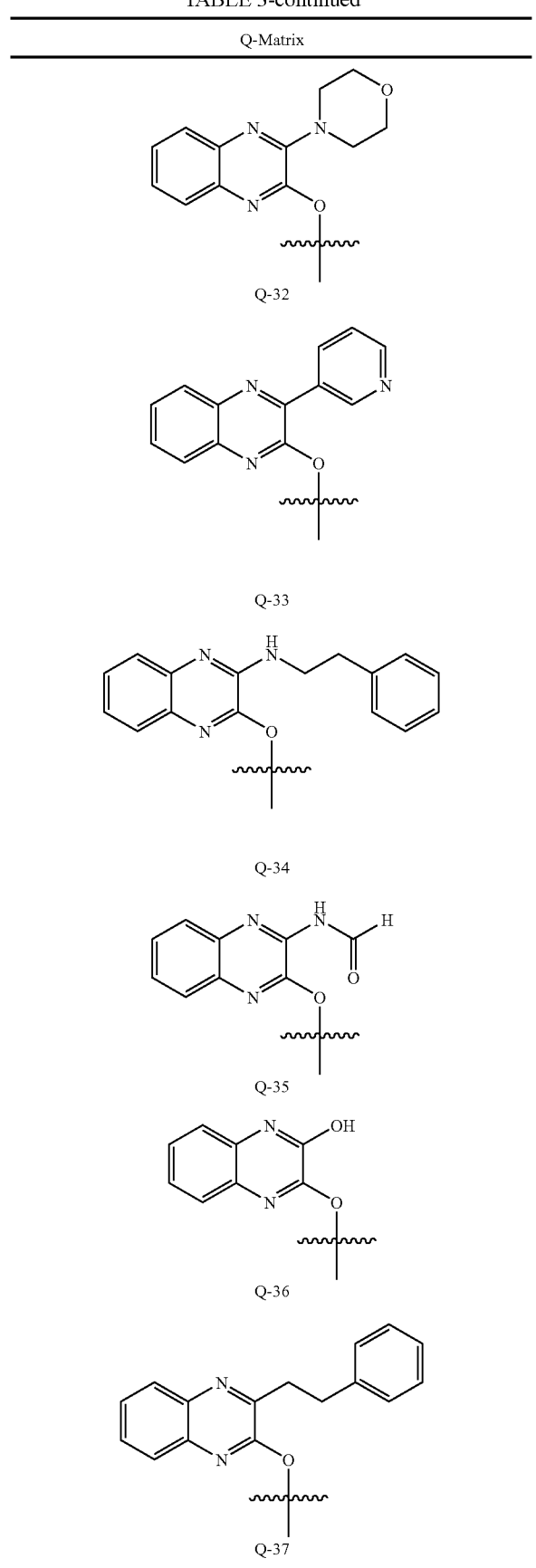
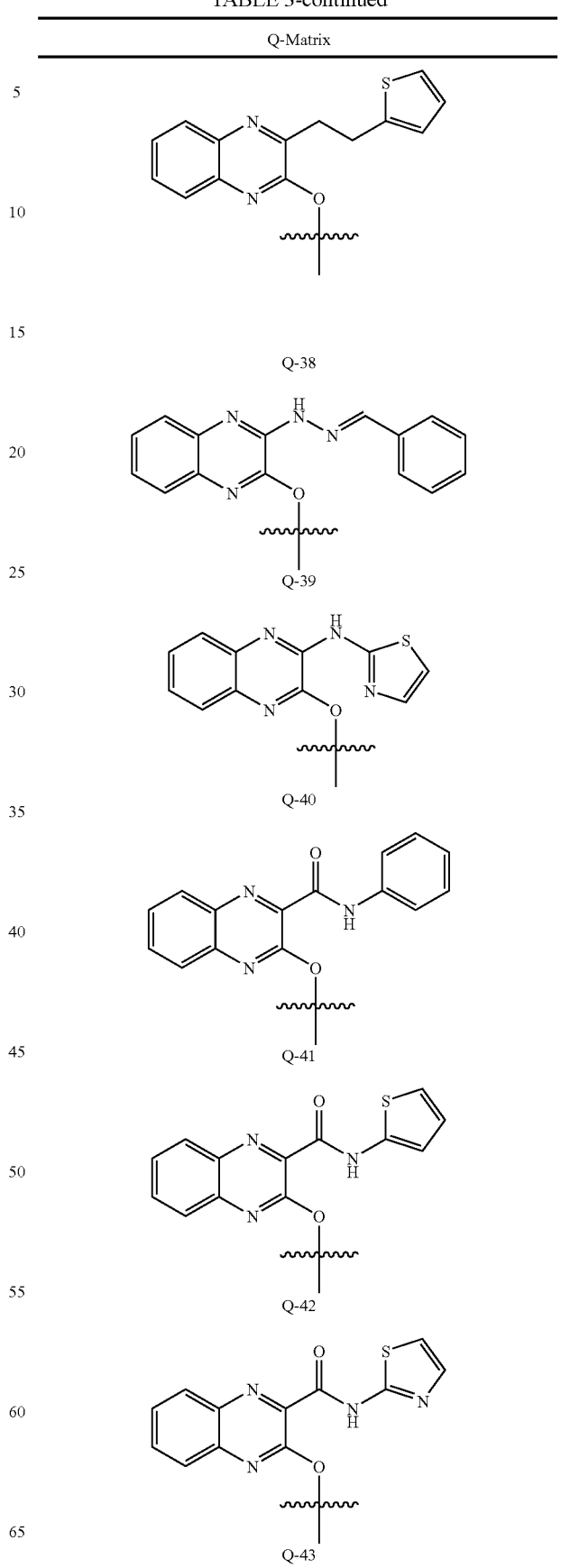

TABLE 3-continued
Q-Matrix
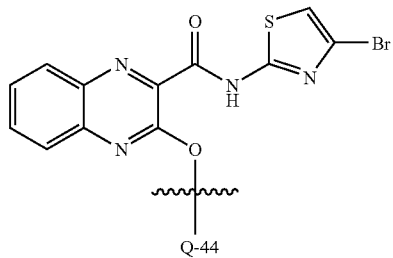
Q-44
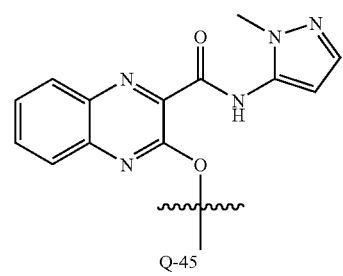
Q-45
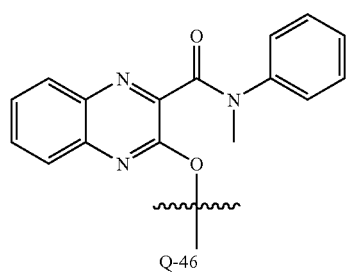
Q-46
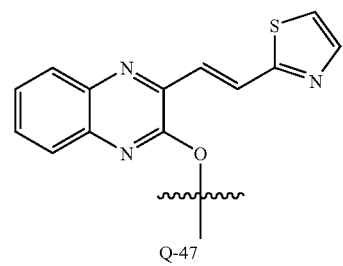
Q-47
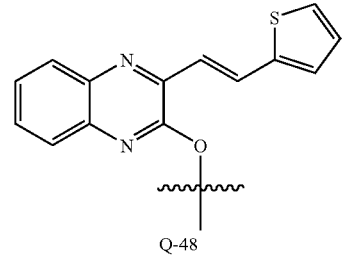
Q-48
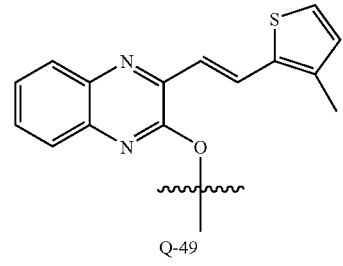
Q-49
TABLE 3-continued
Q-Matrix
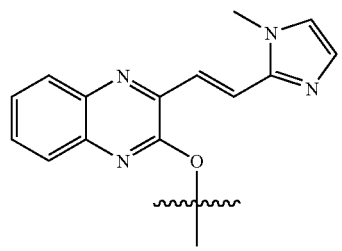
Q-50
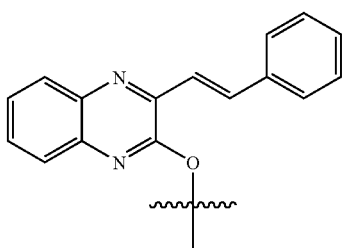
Q-51
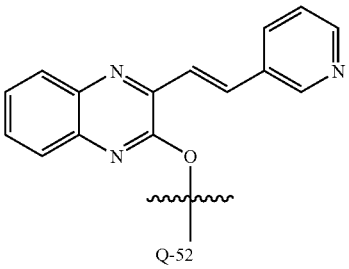
Q-52
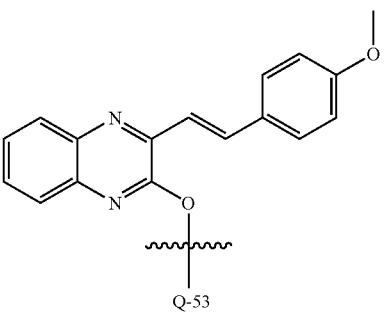
Q-53
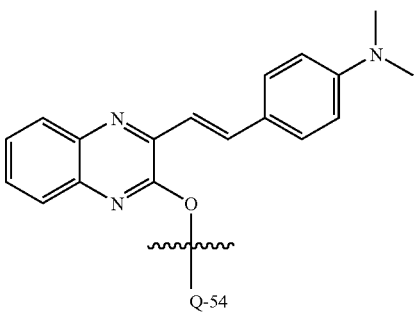
Q-54

TABLE 3-continued
Q-Matrix
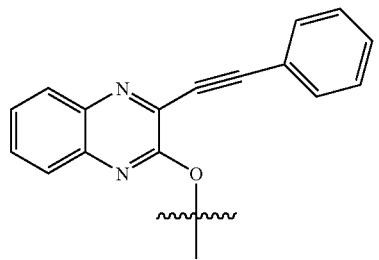
Q-55
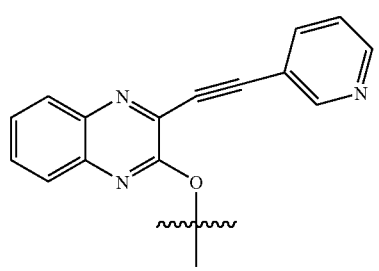
Q-56
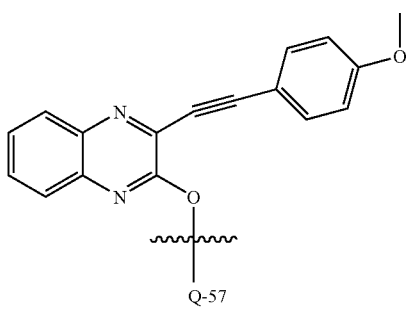
Q-57
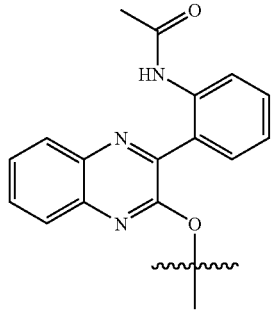
Q-58
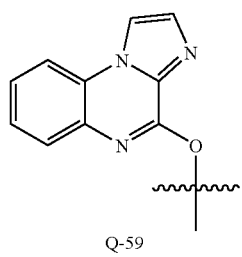
Q-59
TABLE 3-continued
Q-Matrix
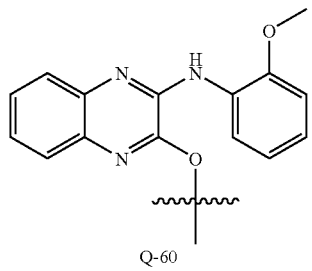
Q-60
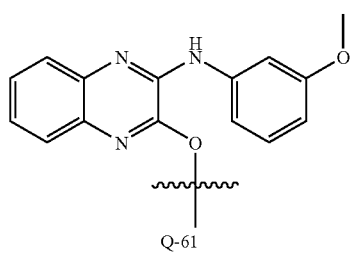
Q-61
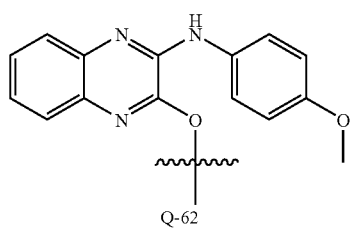
Q-62
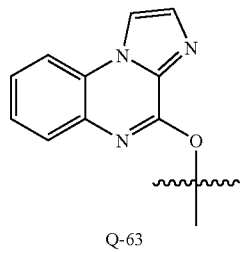
Q-63
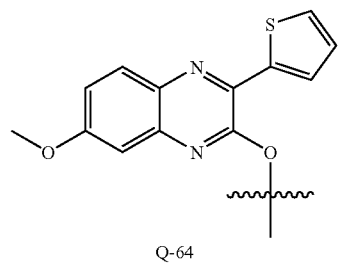
Q-64
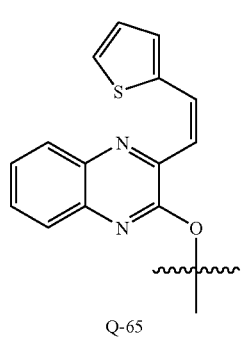
Q-65

TABLE 3-continued

Q-Matrix

Q-66

Q-67

Q-68

TABLE 4

G-Matrix

—OH
G01

G02

G03

G04

TABLE 4-continued

G-Matrix

G05

G06

G07

G08

G09

G10

G11

G12

TABLE 4-continued

G-Matrix

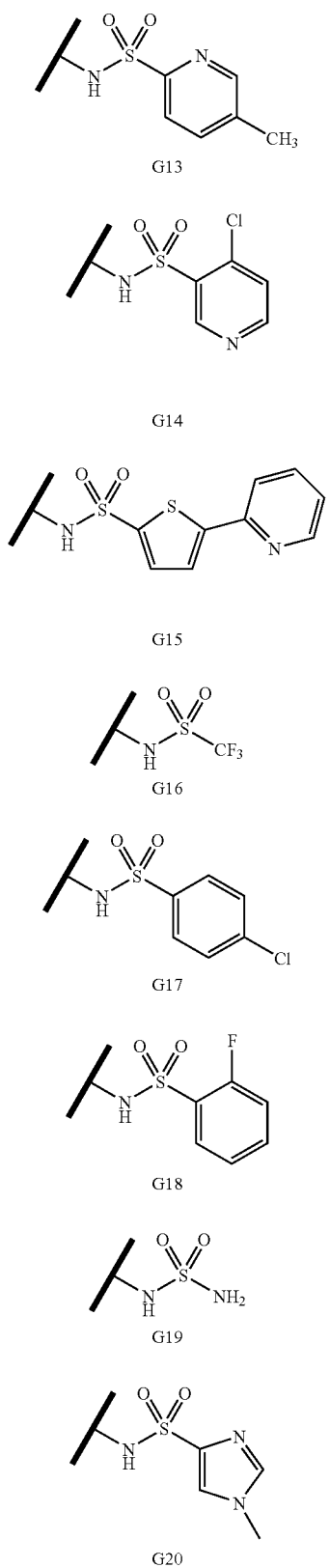

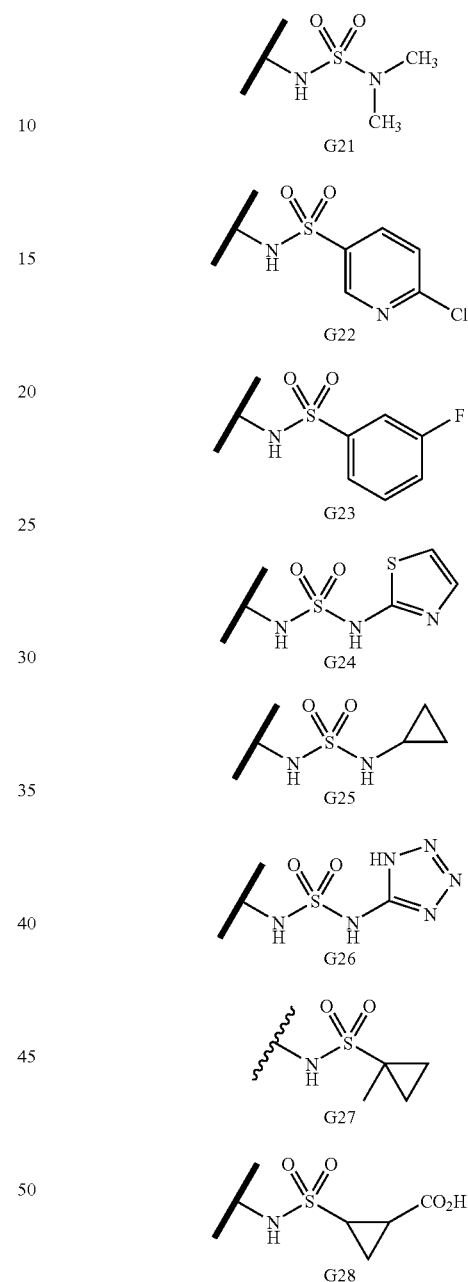

According to an alternate embodiment, the pharmaceutical compositions of the present invention may further contain other anti-HCV agents. Examples of anti-HCV agents include, but are not limited to, β-interferon, β-interferon, ribavirin, and amantadine. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002) which are herein incorporated by reference in their entirety.

According to an additional embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to a further embodiment, the present invention includes methods of treating hepatitis C infections in a subject in need of such treatment by administering to said subject an anti-HCV virally effective amount or an inhibitory amount of the pharmaceutical compositions of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a monovalent group derived from a hydrocarbon moiety containing from two to six, or two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety containing from two to six, or two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted", "substituted $C_1$-$C_6$ alkyl," "substituted $C_1$-$C_8$ alkyl," "substituted $C_2$-$C_6$ alkenyl," "substituted $C_2$-$C_8$ alkenyl," "substituted $C_2$-$C_6$ alkynyl", "substituted $C_2$-$C_8$ alkynyl", "substituted $C_3$-$C_{12}$ cycloalkyl," "substituted $C_3$-$C_8$ cycloalkenyl," "substituted $C_3$-$C_{12}$ cycloalkenyl," "substituted aryl", "substituted heteroaryl," "substituted arylalkyl", "substituted heteroarylalkyl," "substituted heterocycloalkyl," as used herein, refer to CH, NH, $C_1$-$C_6$ alkyl, $C_1$-$C_8$ alkyl, $C_2$-$C_6$ alkenyl, $C_2$-$C_8$ alkenyl, $C_2$-$C_6$ alkynyl, $C_2$-$C_8$ alkynyl, $C_3$-$C_{12}$ cycloalkyl, $C_3$-$C_8$ cycloalkenyl, $C_3$-$C_{12}$ cycloalkenyl, aryl, heteroaryl, arylalkyl, heteroarylalkyl, heterocycloalkyl groups as previously defined, substituted by independent replacement of one, two, or three or more of the hydrogen atoms thereon with substituents including, but not limited to, —F, —Cl, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-

$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_2$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art.

Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

ACN for acetonitrile;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DUPHOS for

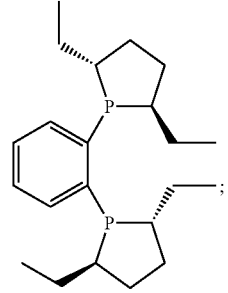

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for 0 (7-Azabenzotriazole-1-yl)-N,N,N',N'-tetramethyluronium hexafluorophosphate;
Hoveyda's Cat. for Dichloro(o-isopropoxyphenylmethylene)(tricyclohexylphosphine)ruthenium(II);
KHMDS is potassium bis(trimethylsilyl)amide;
Ms for mesyl;
NMM for N-4-methylmorpholine
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran;
TLC for thin layer chromatography;
TPP or PPh$_3$ for triphenylphosphine;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared.

Scheme 1

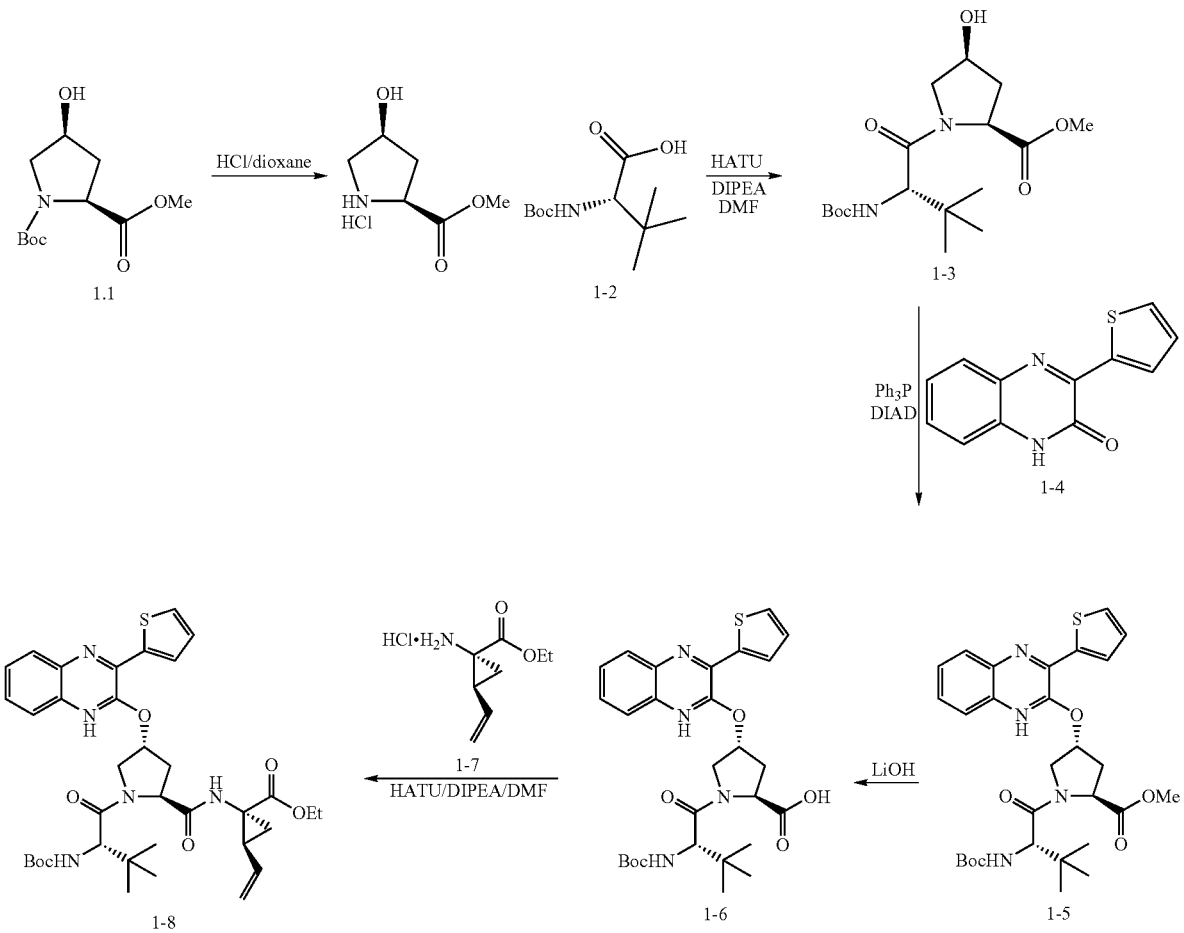

Quinoxalinyl tripeptide carboxylix acid esters can be prepared via two methods (A and B). Method A is exemplified in Scheme 1. Deprotection of commercially available Boc-hydroxyproline 1-1 with HCl in dioxane followed by coupling with acid 1-2 using HATU, afforded intermediate 1-3. Other amino acid derivatives may be used in place of 1-2 in order to generate varied analogs. Reaction of 1-3 with 1-4 (for the preparation of quinoxaline analogs, see Scheme) under Mitsunobu conditions gave compound 1-6. The existing literature predicts Mistonobu product formation at the 1 position nitrogen, however attachment at the carbonyl oxygen was observed to form compound 2-1. A detailed discussion of the identification and characterization of the unexpected oxo Mitosunobu addition product appears in the examples herein. For further details on the Mitsunobu reaction, see O. Mitsunobu, *Synthesis* 1981, 1-28; D. L. Hughes, *Org. React.* 29, 1-162 (1983); D. L. Hughes, *Organic Preparations and Procedures Int.* 28, 127-164 (1996); and J. A. Dodge, S. A. Jones, *Recent Res. Dev. Org. Chem.* 1, 273-283 (1997). Coupling of compound 1-6 with amino acid 1-7 under standard conditions afforded ester 1-8.

Scheme 2

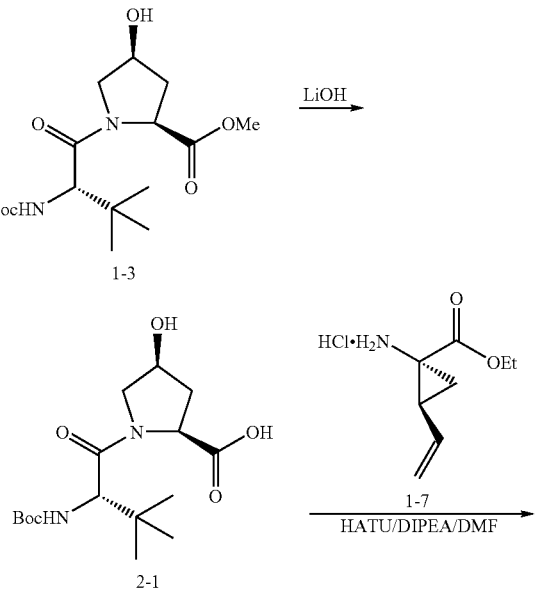

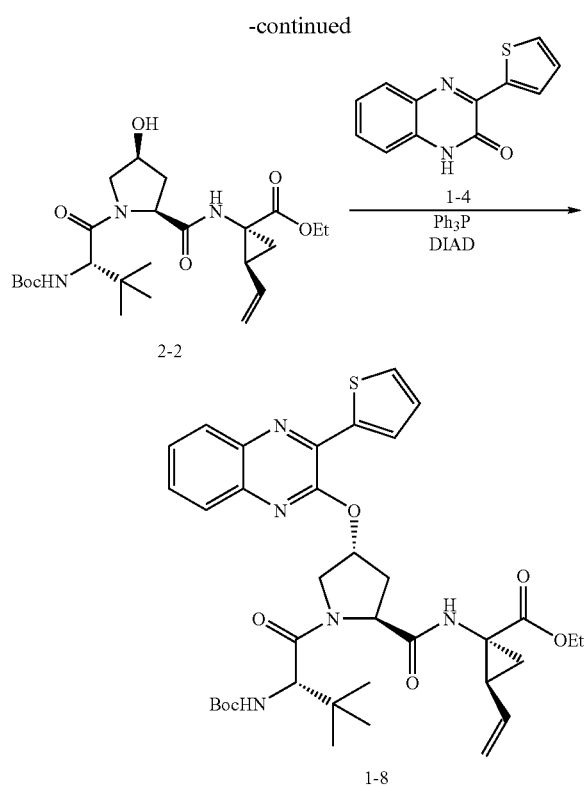

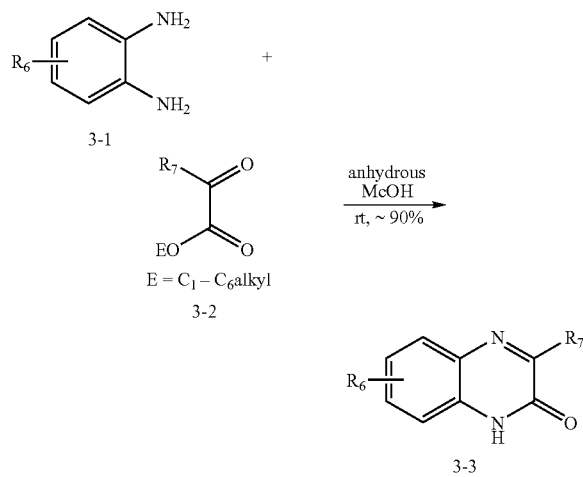

Compound 1-8 can also be prepared via Method B as shown in Scheme 2.

Various quinoxaline derivatives of compound 1-4 (i.e. formula 3-3) can be made via the condensation of phenyl diamines of formula 3-1, wherein $R_6$ is previously defined, with keto acids or esters of formula 3-2, wherein $R_7$ is W-Z as previously defined, in anhydrous methanol at room temperature (see Bekerman et al., *J. Heterocycl. Chem.* 1992, 29, 129-133 for further details of this reaction). Examples of phenyl diamines suitable for creating quinoxaline derivatives of formula 3-3 include, but are not limited to, 1,2-diamino-4-nitrobenze, o-phenylenediamine, 3,4-diaminotoluene, 4-chloro-1,2-phenylenediamine, methyl-3,4-diaminobenzoate, benzo[1,3]dioxole-5,6-diamine, 1,2-diamino-4,5-methylene dioxybenzene, 4-chloro-5-(trifluoromethyl)-1,2-benzenediamine, and the like. Examples of keto acids suitable for the reaction described in Scheme 3 include, but are not limited to, benzoylformic acid, phenylpyruvic acid, indole-3-glyoxylic acid, indole-3-pyruvic acid, nitrophenylpyruvic acid, (2-furyl)glyoxylic acid, and the like. Examples of keto esters suitable for the reaction described in Scheme 3 include, but are not limited to ethyl thiophene-2-glyoxylate, ethyl 2-oxo-4-phenylbutyrate, ethyl 2-(formylamino)-4-thiazolyl glyoxylate, ethyl-2-amino-4-thiozolyl glyoxylate, ethyl-2-oxo-4-phenylbutyrate, ethyl-(5-bromothien-2-yl)glyoxylate, ethyl-3-indolylglyoxylate, ethyl-2-methylbenzoyl formate, ethyl-3-ethylbenzoyl formate, ethyl-3-ethylbenzoyl formate, ethyl-4-cyano-2-oxobutyrate, methyl(1-methylindolyl)-3-glyoxylate, and the like.

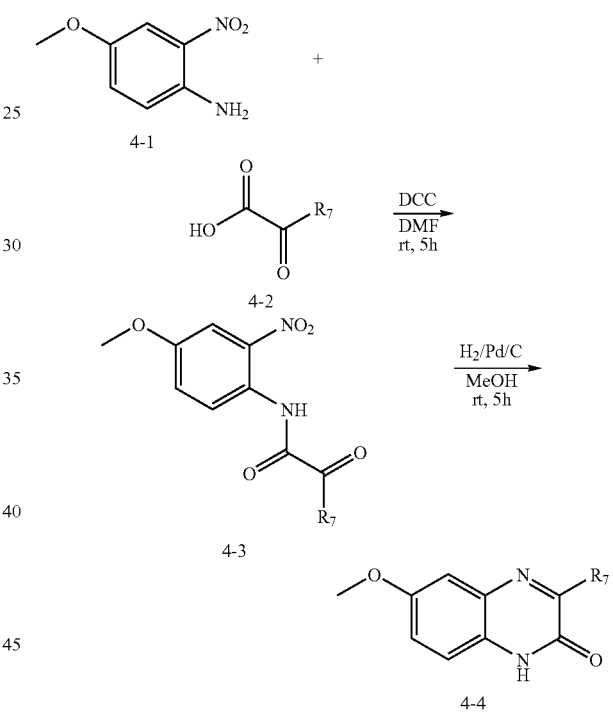

3,6-substituted quinoxalin-2-ones of formula 4-4, wherein $R_7$ is W-Z as previously defined, can be made in a regioselective manner to favor the 6-position substitution beginning with the amide coupling of 4-methoxy-2-nitro aniline 4-1 and substituted glyoxylic acid 4-2 to yield compound 4-3. The 3,6-substituted quinoxalin-2-one 4-4 was created via catalytic reduction of the nitro of compound 4-3 followed by condensation. Other substituents may be introduced into 4-4 through the use of other 2-nitroanilines. Examples of keto acids suitable for the reaction described in Scheme 4 include, but are not limited to, benzoylformic acid, phenylpyruvic acid, indole-3-glyoxylic acid, indole-3-pyruvic acid, nitrophenylpyruvic acid, (2-furyl)glyoxylic acid, and the like. Examples of 2-nitro anilines suitable for the reaction described in Scheme 4 include, but are not limited to, 4-ethoxy-2-nitroaniline, 4-amino-3-nitrobenzotrifluoride, 4,5-dimethyl-2-nitroaniline, 4-fluoro-2-nitroaniline, 4-chloro-2-nitroaniline, 4-amino-3-nitromethylbenzoate, 4-benzoyl-2-nitroaniline, 3-bromo-4-methoxy-2-nitroaniline, 3'-amino-4'-methyl-2-nitroacetophenone, 5-ethoxy-4-fluoro-2-nitroaniline, 4-bromo-2-nitroaniline, 4-(trifluoromethoxy)-2-nitroaniline, ethyl-4-amino3-nitrobenzoate, 4-bromo-2-methyl-6-nitroaniline, 4-propoxy-2-nitroaniline, 5-(propylthio)-2-nitroaniline, and the like.
Scheme 5
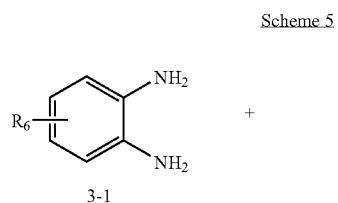
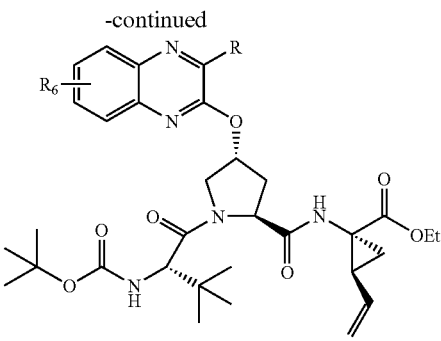
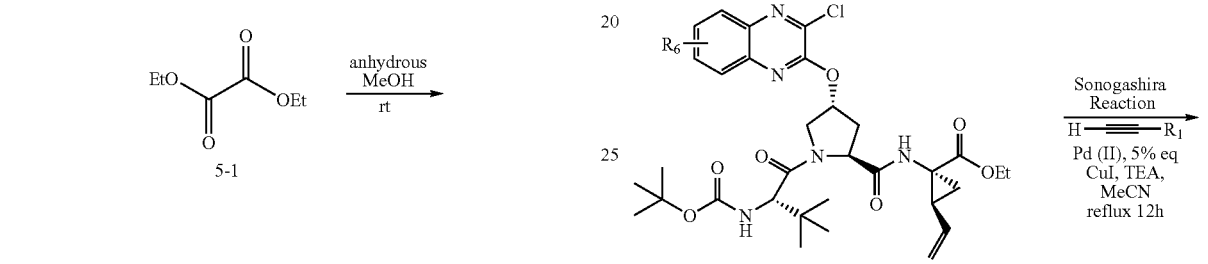
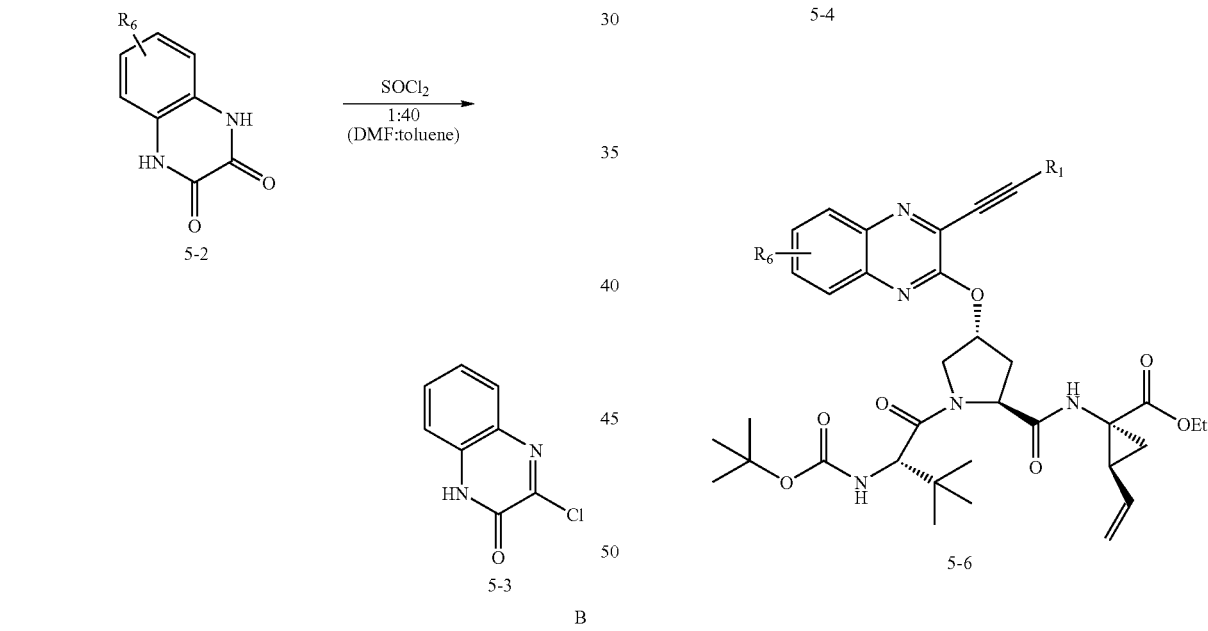
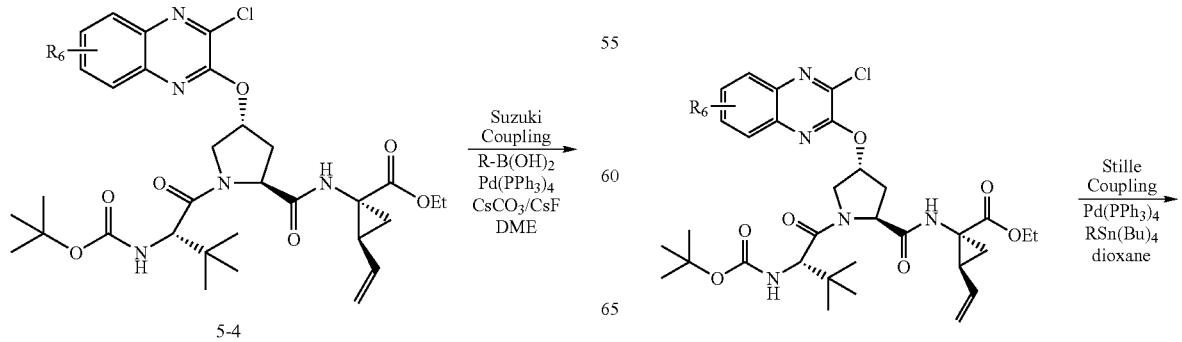

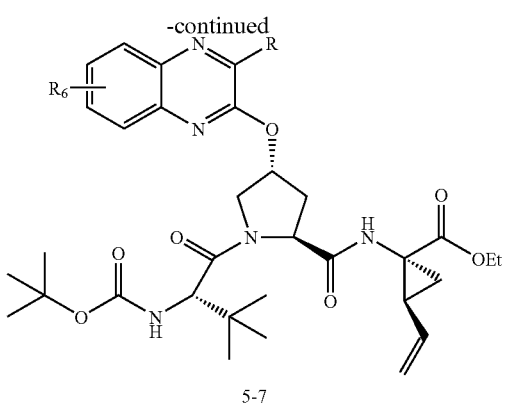

5-7

A. A key intermediate, 3-chloro-1H-quinoxalin-2-one 5-3, can be synthesized in two steps beginning with the condensation of phenyl diamines of formula 3-1, as previously defined, and oxalic acid diethyl ester 5-1 under similar conditions as discussed in Scheme 3 (see Bekerman et al., *J. Heterocycl. Chem.* 1992, 29, 129-133). The resulting 1,4-dihydro-quinoxaline-2,3-dione 5-2 was then treated with $SOCl_2$ (1.37 equiv.) in 1:40 DMF:toluene (see Loev et al, *J. Med. Chem.* (1985), 28, 363-366 for further details) to afford the desired intermediate 5-3.

B. The key 3-chloro-quinoxalin-2-one 5-3 was added to the macrocyclic precursor 1-6 via Mitsunobu conditions, adding via the carbonyl oxygen rather than the expected 1-position nitrogen, to give the macrocylic intermediate of formula 5-4. This intermediate facilitates the introduction of various substituents at the 3-position of the quinoxaline.

Suzuki Coupling

Compounds of formula 5-5, wherein $R_6$ is previously defined and R is an aryl, substituted aryl, heteroaryl or substituted heteroaryl as previously defined, can be synthesized via Suzuki coupling reaction with an aryl, substituted aryl, heteroaryl, or substituted heteroaryl boronic acid in DME in the presence of $Pd(PPh_3)_4$, and $CsCO_3$. For further details concerning the Suzuki coupling reaction see: A. Suzuki, *Pure Appl. Chem.* 1991, 63, 419-422 and A. R. Martin, Y. Yang, *Acta Chem. Scand.* 1993, 47, 221-230. Examples of boronic acids suitable for Suzuki coupling to macrocyclic key intermediate 5-5 include, but are not limited to, 2-bromo thiophene, phenylboronic acid, 5-bromothiophene-3-boronic acid, 4-cyanophenylboronic acid, 4-trifluormethoxyphenylboronic acid, and the like.

Sonogashira Reaction

Compounds of formula 5-6, wherein $R_1$ is as previously defined and $R_6$ is as previously defined, can be synthesized via Sonagashira reaction with the macrocyclic key intermediate and a terminal alkyne in acetonitrile in the presence triethylamine, $PdCl_2(PPh_3)_2$, and CuI at 90° C. for 12 hours. For further details of the Sonogashira reaction see: Sonogashira, *Comprehensive Organic Synthesis*, Volume 3, Chapters 2,4 and Sonogashira, *Synthesis* 1977, 777. Terminal alkenes suitable for the Sonogashira reaction with macrocyclic key intermediate 5-5 include, but are not limited to, ethynylbenzene, 4-cyano-ethynylbenzene, propargylbenzene, and the like.

Stille Coupling

Compounds of formula 5-7, wherein $R_6$ is previously defined and R is an aryl, substituted aryl, heteroaryl or substituted heteroaryl as previously defined, can be synthesized via Stille coupling reaction with key macrocyclic intermediate of formula 5-4 and aryl stannanes in dioxane in the presence of $Pd(PPh_3)_4$. For further details of the Stille coupling reaction see: J. K. Stille, *Angew. Chem. Int. Ed.* 1986, 25, 508-524, M. Pereyre et al., *Tin in Organic Synthesis* (Butterworths, Boston, 1987) pp 185-207 passim, and a review of synthetic applications in T. N. Mitchell, *Synthesis* 1992, 803-815. Organostannanes suitable for Stille coupling with key macrocyclic intermediate 5-4 include, but are not limited to, tributyltin cyanide, allyl-tri-n-butyltin, 2-tributyltin-pyridine, 2-tri-n-butyltin furan, 2-tri-n-butyltin thiophene, 2,3-dihydron-5-(tri-n-butyltin)benzofuran, and the like.

Scheme 6

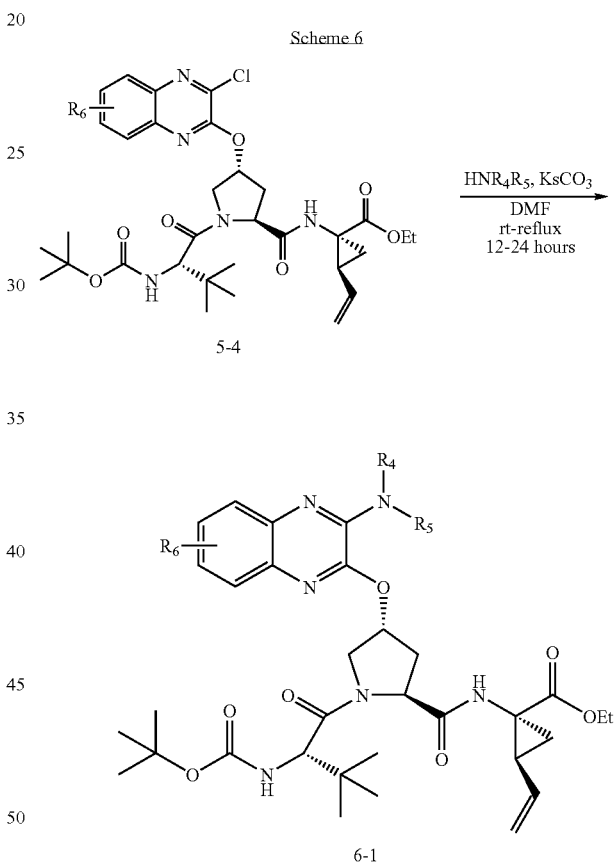

6-1

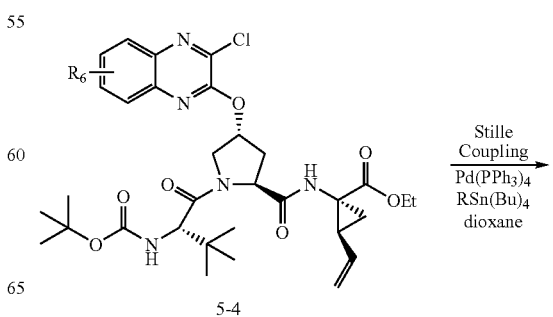

5-4

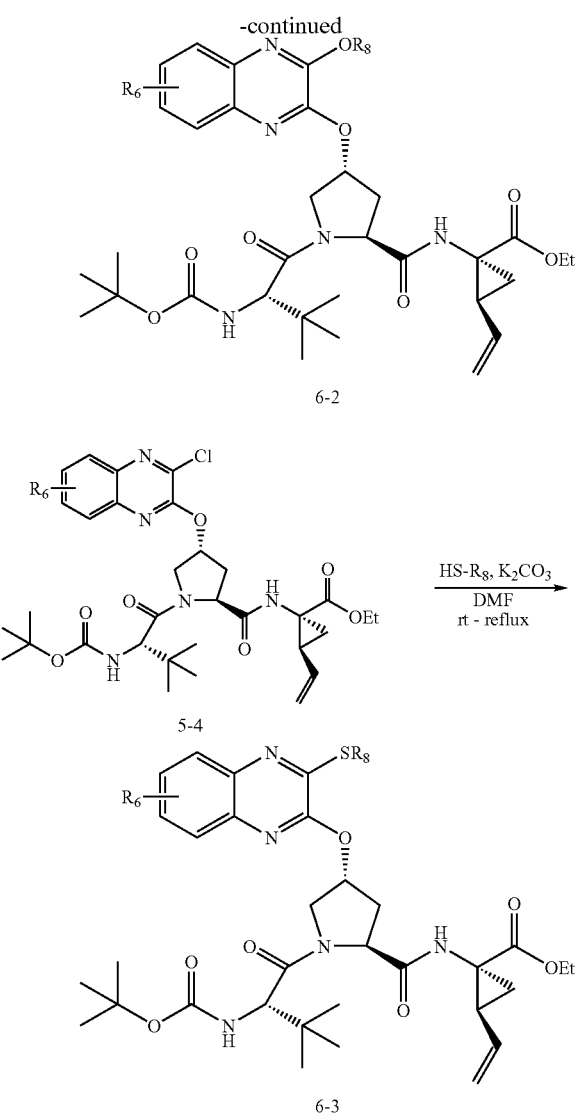

Via the key macrocyclic 3-chloro-quinoxalinyl intermediate 5-4, three additional classes of substituents may be introduced at the 3-position of the quinoxaline ring. Among the various groups that may be introduced are mono-substituted amino, di-substituted amino, ethers, and thio-ethers.

The amino-substituted quinoxaline 6-1, wherein $R_4$, $R_5$, $R_6$ are previously defined and $R_8$ is Z as previously defined, can be formed through adding $K_2CO_3$ (2.0 equiv.) and $HNR_4R_5$ (1.2 equiv.) to a 0.1M solution of macrocyclic quinoxalinyl intermediate 5-4 in 10 ml DMF, and stirring the resulting reaction mixture at room temperature for 5-12 hours. Amines suitable for these conditions include, but are not limited to, ethyl amine, 2-phenyl ethyl amine, cyclohexyl amine, ethylmethyl amine, diisopropyl amine, benzylethyl amine, 4-pentenyl amine, propargyl amine and the like.

For amines of the formula $HNR_4R_5$ wherein $R_4$ is H and $R_5$ is aryl, substituted aryl, heteroaryl, or substituted heteroaryl, a different set of conditions must be used to generate the corresponding compound 6-1. Addition of NaH (2.0 equiv.) and $HNR_4R_5$ (1.2 equiv.) to a 0.1M solution of the macrocyclic quinoxalinyl intermediate 5-4 in THF and stirring the resulting reaction mixture for 5-12 hours, afforded the aniline substituted compound 6-1. Amines suitable for these conditions are aniline, 4-methoxy aniline, 2-amino-pyridine, and the like.

Introduction of ethers to the 3-position of the quinoxaline ring can be achieved through treating a 0.1M solution of macrocyclic quinoxalinyl intermediate 5-4 in DMF with $K_2CO_3$ (2.0 equiv.) and $HOR_8$ (1.2 equiv.), wherein $R_8$=Z as previously defined. The resulting reaction mixture can then be stirred for 5-12 hours at room temperature to generate the desired ether moiety at the 3-position. Alcohols suitable for these conditions include, but are not limited to, ethanol, propanol, isobutanol, trifluoromethanol, phenol, 4-methoxyphenol, pyridin-3-ol, and the like. Thioesters can be made via the same procedure.

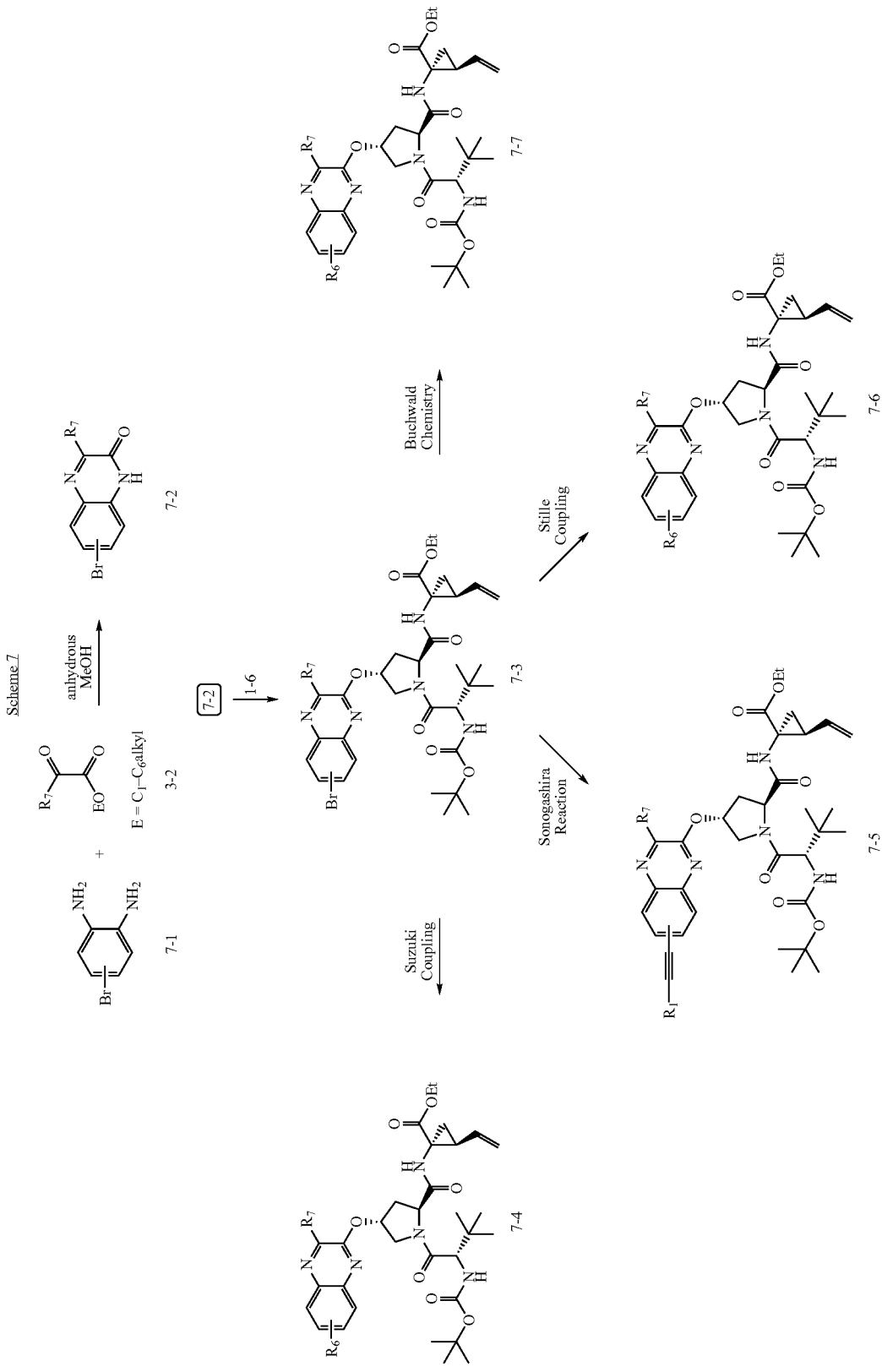

Derivation of the benzo portion of the quinoxaline ring may be achieved through the halogen-substituted quinoxaline of formula 7-2. Quinoxaline of formula 7-2 can be formed via the condensation of bromo-substituted phenyldiamine 7-1 with a diketo compound of formula 3-2, wherein $R_7$=W-Z as previously defined, in anhydrous methanol as previously detailed. Intermediate 7-3 was formed under Mitsunobu conditions with macrocyclic precursor 7-6 and bromosubstituted quinoxaline 7-2. Intermediate 7-3 may then undergo Suzuki coupling reactions, Sonogashira reactions, or Stille couplings at the position occupied by the bromo. See previous discussion of Suzuki couplings, Sonogashira reactions, and Stille couplings for further details. The Buchwald reaction allows for the substitution of amines, both primary and secondary, as well as 1H-nitrogen heterocycles at the aryl bromide. For further details of the Buchwald reaction see J. F. Hartwig, *Angew. Chem. Int. Ed.* 1998, 37, 2046-2067.

the method described previously in Scheme 3 (see Bekerman et al., *J. Heterocycl. Chem.* 1992, 29, 129-133 for further details). The resulting ethyl ester 8-3 was then hydrolyzed with LiOH in MeOH at room temperature to yield carboxylic acid intermediate 8-4.

Carboxylic acid 8-4 then may be converted to substituted ketone 8-6 (wherein $R_1$ is as previously defined) via Weinreb's amide 8-5 and subsequent treatment with various Grignard Reagents (see Weinreb et al. *Tetrahedron Lett.* 1977, 33, 4171; Weinreb et al, *Synth. Commun.* 1982, 12, 989 for details of the formation and use of Weinreb's amide; and see B. S. Furniss, A. J. Hannaford, P. W. G Smith, A. R. Tatchell, *Vogel's Textbook of Practical Organic Chemistry*, $5^{th}$ ed., Longman, 1989). The addition was performed in an inert solvent, generally at low temperatures. Suitable solvents include, but are not limited to, tetrahydrofuran, diethylether, 1,4-dioxane, 1,2-dimethoxyethane, and hexanes. Preferably

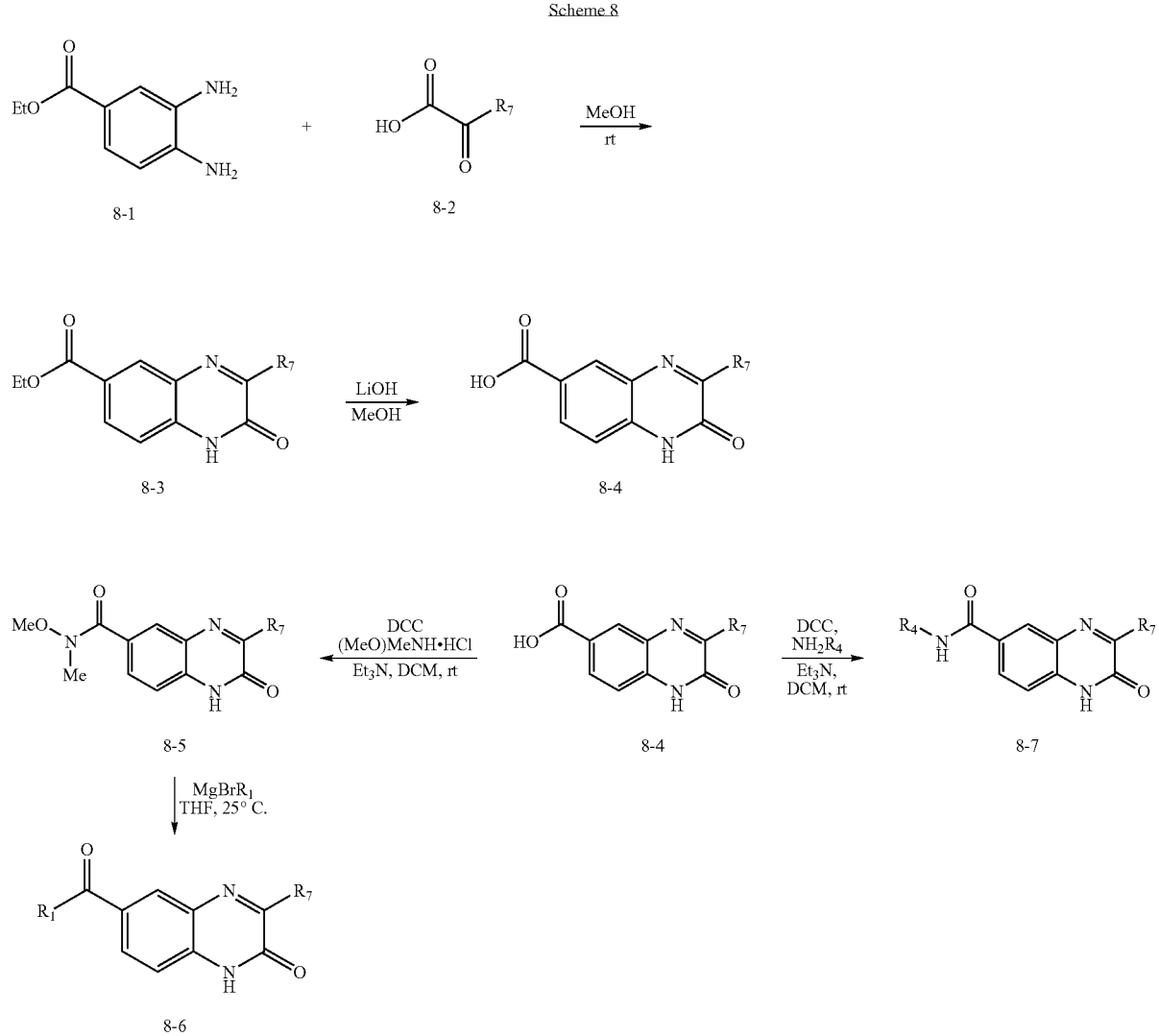

Scheme 8

The 3-substituted 2-oxo-1,2-dihydro-quinoxaline-6-carboxylic acid intermediate 8-4 can be formed via condensation of ethyl 3,4-diaminobenzoate (8-1) with oxo acetic acid of formula 8-2, wherein $R_7$=W-Z as previously defined, using the solvent was tetrahydrofuran or diethylether. Preferably the reaction was carried out at −78° C. to 0° C.

Alternatively, carboxylic acid 8-4 may be used to form various amides of formula 8-7, wherein $R_4$ is as previously defined, in a manner generally described in Scheme 8. All of the various quinoxalin-2-one compounds described in Scheme 8 are further coupled to the macrocyclic precursor via the Mitsunobu conditions described above.

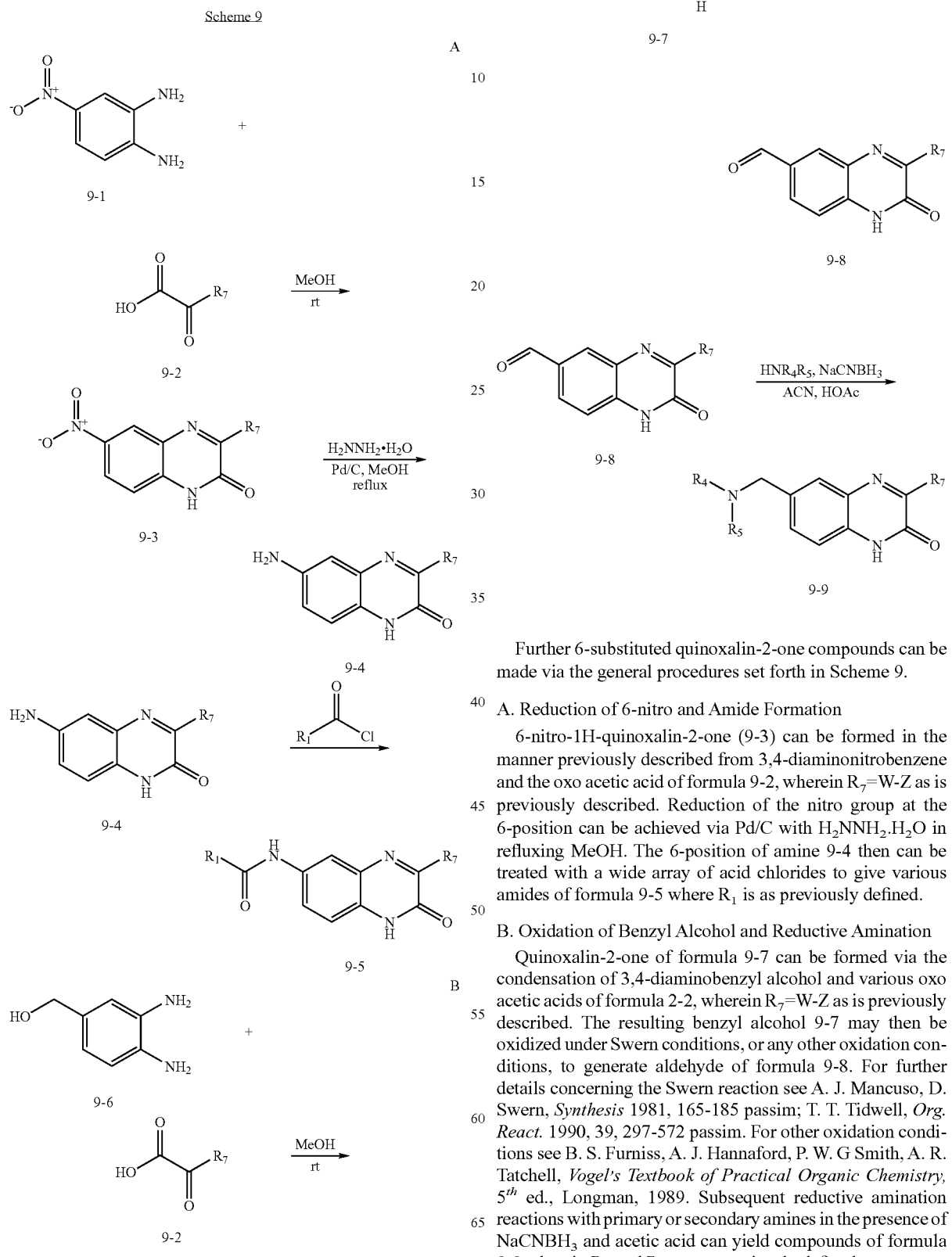

Further 6-substituted quinoxalin-2-one compounds can be made via the general procedures set forth in Scheme 9.

A. Reduction of 6-nitro and Amide Formation 6-nitro-1H-quinoxalin-2-one (9-3) can be formed in the manner previously described from 3,4-diaminonitrobenzene and the oxo acetic acid of formula 9-2, wherein $R_7$=W-Z as is previously described. Reduction of the nitro group at the 6-position can be achieved via Pd/C with $H_2NNH_2.H_2O$ in refluxing MeOH. The 6-position of amine 9-4 then can be treated with a wide array of acid chlorides to give various amides of formula 9-5 where $R_1$ is as previously defined.

B. Oxidation of Benzyl Alcohol and Reductive Amination

Quinoxalin-2-one of formula 9-7 can be formed via the condensation of 3,4-diaminobenzyl alcohol and various oxo acetic acids of formula 2-2, wherein $R_7$=W-Z as is previously described. The resulting benzyl alcohol 9-7 may then be oxidized under Swern conditions, or any other oxidation conditions, to generate aldehyde of formula 9-8. For further details concerning the Swern reaction see A. J. Mancuso, D. Swern, *Synthesis* 1981, 165-185 passim; T. T. Tidwell, *Org. React.* 1990, 39, 297-572 passim. For other oxidation conditions see B. S. Furniss, A. J. Hannaford, P. W. G Smith, A. R. Tatchell, *Vogel's Textbook of Practical Organic Chemistry*, 5$^{th}$ ed., Longman, 1989. Subsequent reductive amination reactions with primary or secondary amines in the presence of $NaCNBH_3$ and acetic acid can yield compounds of formula 9-9 wherein $R_4$ and $R_5$ are as previously defined.

Scheme 10

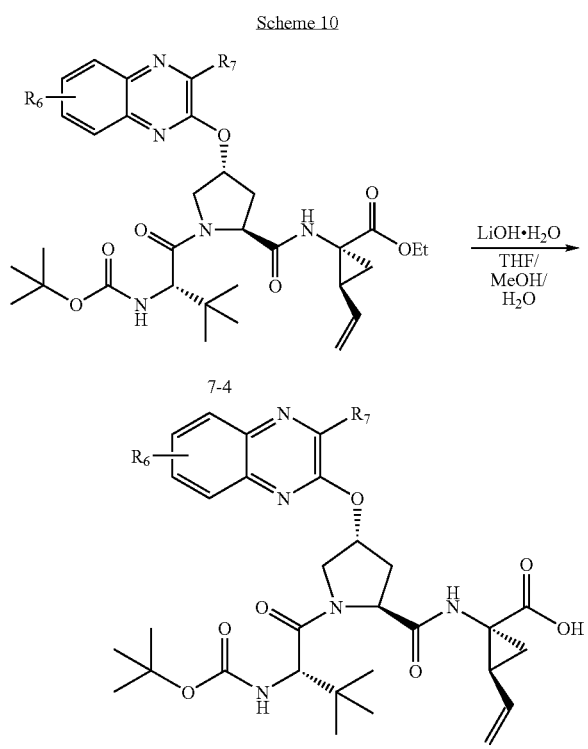

Hydrolysis of the preceding quinoxalinyl tripeptide ester compounds was carried out in standard fashion. A solution of the ethyl ester 7-4 in THF/MeOH/H₂O was treated with LiOH.H₂O to afford the corresponding free acid wherein $R_6$ is as previously defined and $R_7$=W-Z as previously defined.

Scheme 11

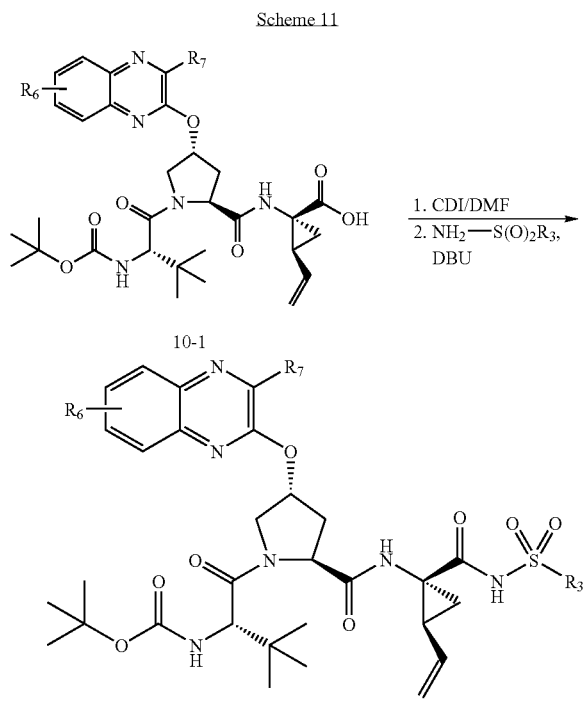

The sulfonimides 11-1 were prepared from the corresponding acids 10-1 by subjecting the acid to a coupling reagent (i.e. CDI, HATU, DCC, EDC and the like) at RT or at elevated temperature, with the subsequent addition of the corresponding sulfonamide $R_3$—S(O)$_2$—NH$_2$ in the presence of base wherein $R_3$, $R_6$ and R are as previously defined and $R_7$=W-Z as previously defined.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims

Example 1

Compound of Formula IV, wherein

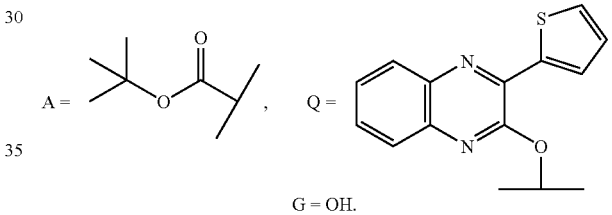

G = OH.

Step 1A

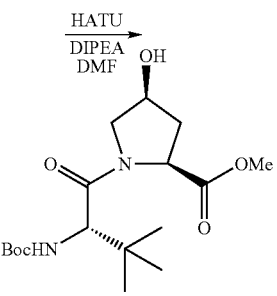

To a solution of Boc-L-tert-leucine (4.544 g, 19.65 mmol), cis-L-hydroxyproline methyl ester (19.65 mmol) and DIPEA (10.3 ml, 59.1 mmol) in DMF (80 ml) at 0° C. was added in portions HATU (7.84 g, 20.6 mmol). The mixture was stirred at rt for 18 h, diluted with EtOAc and washed with half-sat.-aq. NaCl four times. The organic phase was dried over anhydrous MgSO$_4$, filtered, and then concentrated in vacuo. The resudue was purified by silica gel chromatography (Hexane/EtOAC=1:1 to 1:2) to afford compound 1a (7.8 g). MS (ESI): m/e 359.24 (M+H).

Step 1B

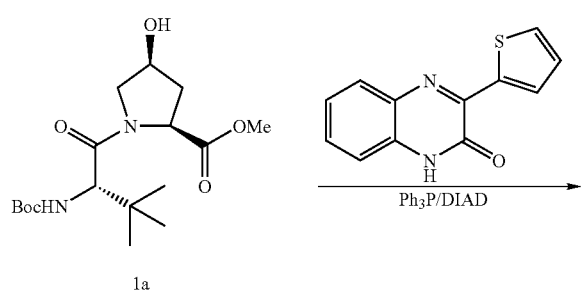

1a

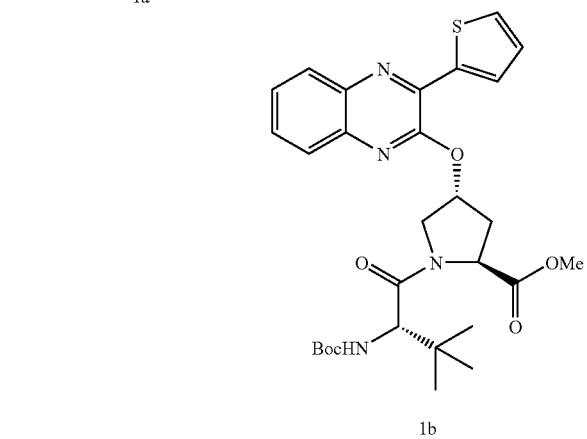

1b

To a mixture of the above 1a (1.363 g, 3.803 mmol), 3-(thiophen-2-yl)-1H-quinoxalin-2-one (0.868 g, 3.803 mmol)) and triphenylphosphine (2.0 g, 7.6 mmol) in THF at 0° C. was added dropwise DIAD (1.5 ml, 7.6 mmol). The resulting mixture was held at 0° C. for 15 min. before being warmed to room temperature. After 18 hours, the mixture was concentrated under vacuum and the residue was purified by chromatography (Hexane/EtOAC=9:1 to 7:3) to give 1b (1.8 g). MS(ESI): m/e 569.27 (M+H).

Step 1C

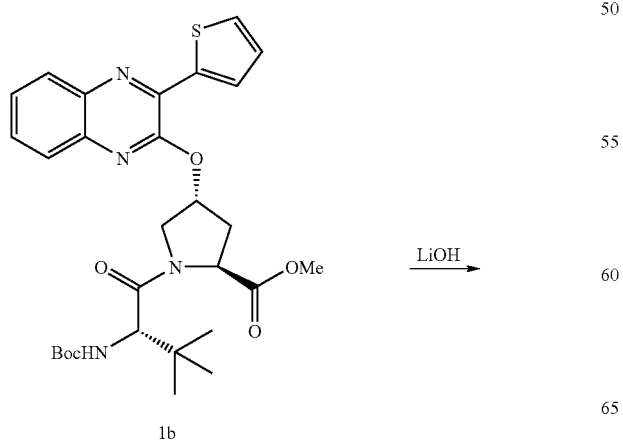

1b

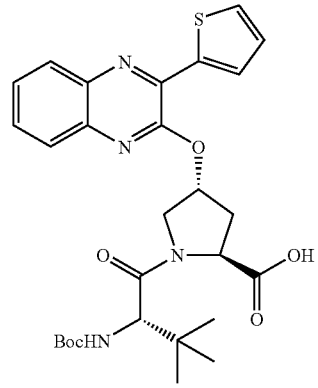

To a solution of compound 1b (1.77 g, 3.11 mmol) in THF/MeOH/H$_2$O (36 ml-18 ml-18 ml) was added lithium hydroxide mono hydrate (0.783 g, 18.6 mmol). The mixture was stirred at room temperature for 20 hours. Most organic solvents were evaporated in vacuo, and the resulting residue was diluted with water and acidified to pH 5 to 6. The mixture was extracted with EtOAc three times. The combined organic extracts were dried (MgSO$_4$), filtered and concentrated in vacuo to afford 1c (95%). MS(ESI): m/e 555.26 (M+H).

Step 1D

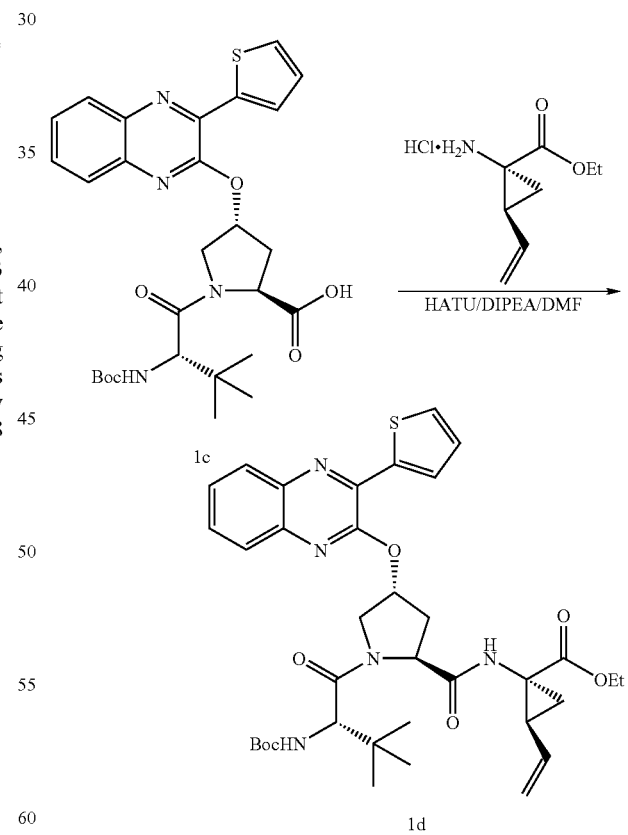

1c

1d

To a solution of 1c (98 mg, 0.177 mmol), (1R,2S)-1-Amino-2-vinyl-cyclopropanecarboxylic acid ethyl ester HCl salt (34 mg, 0.177 mmol) and DIPEA (0.125 ml, 0.71 mmol) in DMF (3 ml) at 0° C. was added HATU (81 mg, 0.212 mmol). The mixture was stirred at rt for 18 h, diluted with EtOAc and washed with half-sat.-aq. NaCl four times. The organic phase was dried over anhydrous MgSO$_4$, filtered, and then concentrated in vacuo. The resudue was purified by silica gel chromatography (Hexane/EtOAC=3:1 to 2:1) to afford compound 1d (86 mg). MS (ESI): m/e 692.32 (M+H).

Step 1E

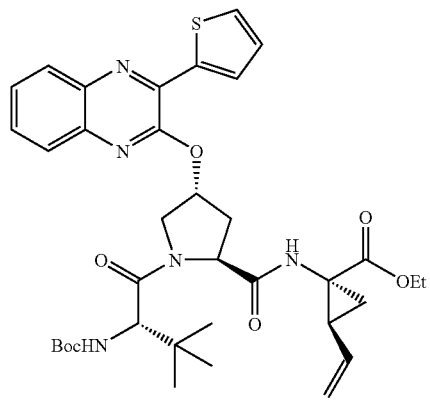

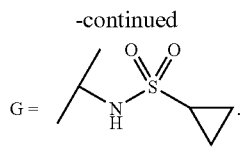

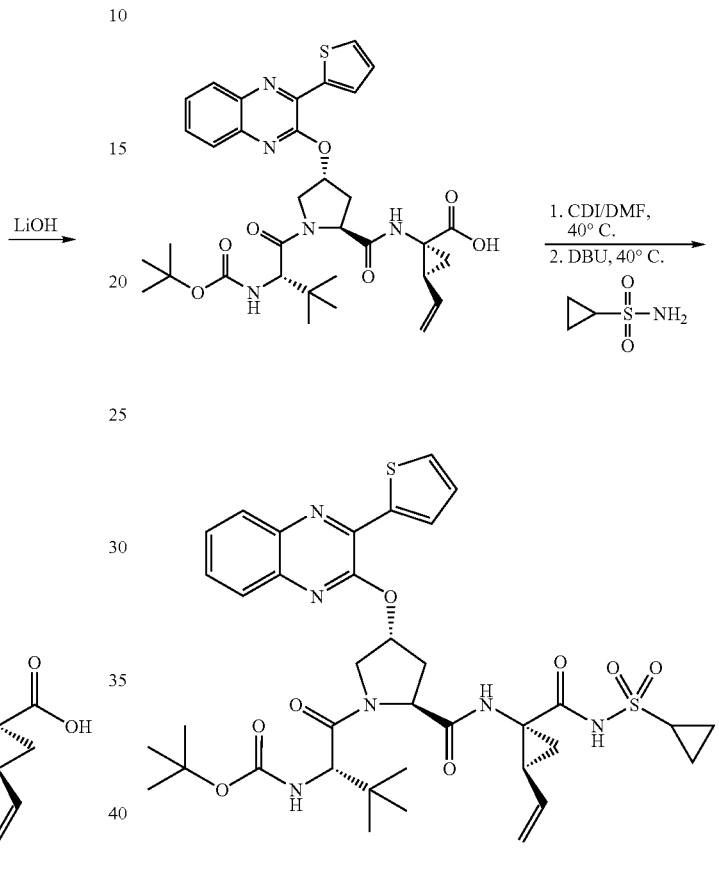

To a solution of compound 1d (79 g, 0.114 mmol) in THF/MeOH/H$_2$O (2 ml-1 ml-0.5 ml) was added aqueous lithium hydroxide (1N, 0.6 ml, 0.6 mmol.). The mixture was stirred at room temperature for 20 hours. Most organic solvents were evaporated in vacuo, and the resulting residue was diluted with water and acidified to pH 5 to 6. The mixture was extracted with EtOAc three times. The combined organic extracts were dried (MgSO$_4$), filtered and concentrated in vacuo to afford compound 1 (73 mg). MS(ESI): m/e 664.20 (M+H).

Example 2

Compound of Formula IV, wherein

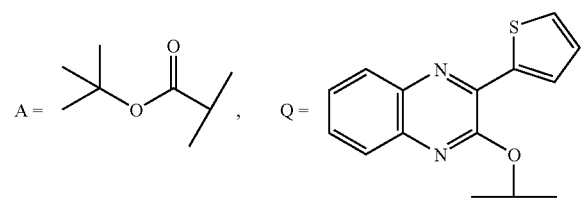

Step 2A: Cyclopropylsulfonyl chloride (5 g, 35.56 mmol) was dissolved in 0.5 M ammonia in dioxane (200 ml, 100 mmol) at RT. The reaction was stirred at RT for 3 days. The large amount of precipitation was filtered and discarded. The clear filtrate was evaporated in vacuo and the white residue was dried on vacuum for 24 hours to give the cyclopropylsulfonamide (>90%). $^1$H-NMR (500 MHz, CD$_3$Cl): δ 4.62 (2H, s), 2.59 (1H, m), 1.20 (2H, m), 1.02 (2H, m).

Step 2B: The title compound from Example 1 (37 mg, 0.056 mmol) and carbonyldiimidazole (14 mg, 0.086 mmol) were dissolved in 1 ml of anhydrous DMF and the resulting solution was stirred at 40° C. for 1 hour. Cyclopropylsulfonamide (10 mg, 0.084 mmol) was added to the reaction followed by DBU (8 ul, 0.056 mmol). The reaction mixture was stirred at 40° C. for 20 hour. The reaction mixture was diluted with ethyl acetate and washed with half-saturated-aqueous NaCl solution three times. The organic layer was dried over anhydrous (MgSO$_4$) and concentrated in vacuo. The residue was purified by silica gel chromatography (Hexans/EtOAc=3:1 to 1:1) to give the title compound (17 mg). MS(ESI): m/e 767.23 (M+H).

Example 3
Compound of Formula IV, wherein A=H,
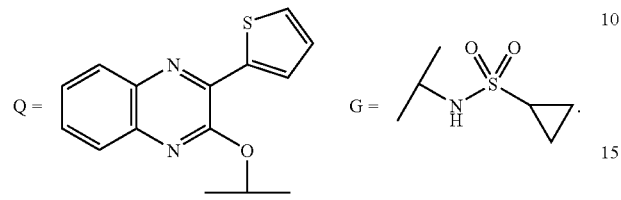
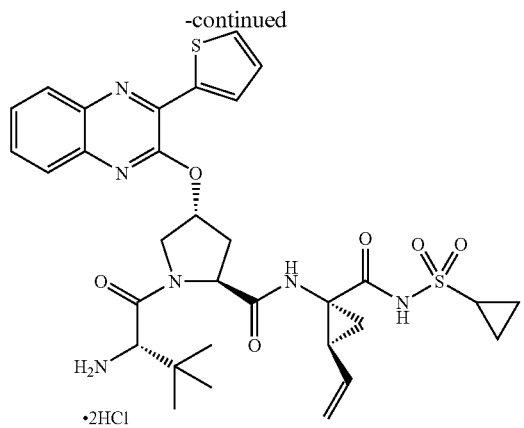
•2HCl
The title compound of Example 2 (25 mg, 0.0362 mmoL0 was treated with 4M HCl/dioxane (1 ml, 4 mmol). The mixture was stirred at room temperature for 1 hour, and concentrated in vacuo to dryness to affor the title compound (100%). MS (ESI): m/e 667.32 (M+H)
Example 4
Compound of Formula IV, wherein
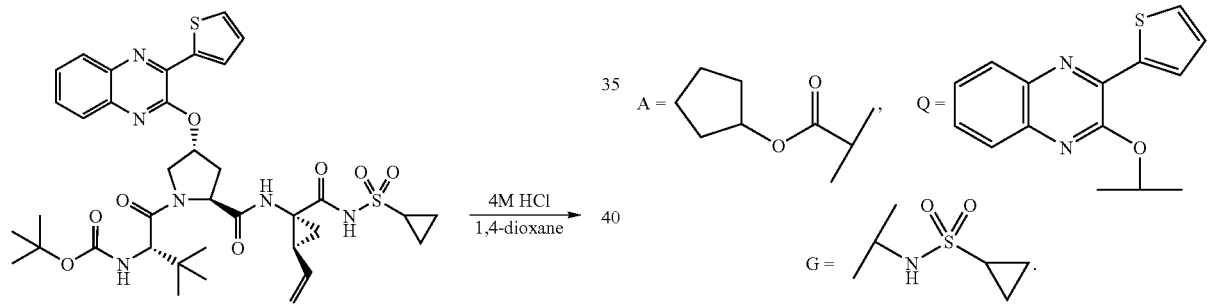
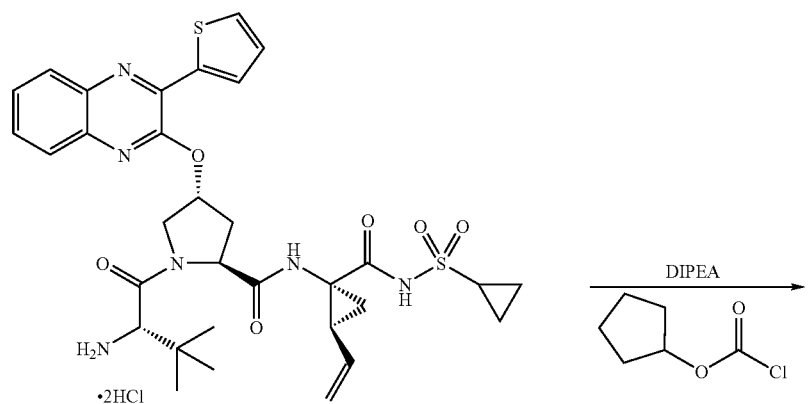

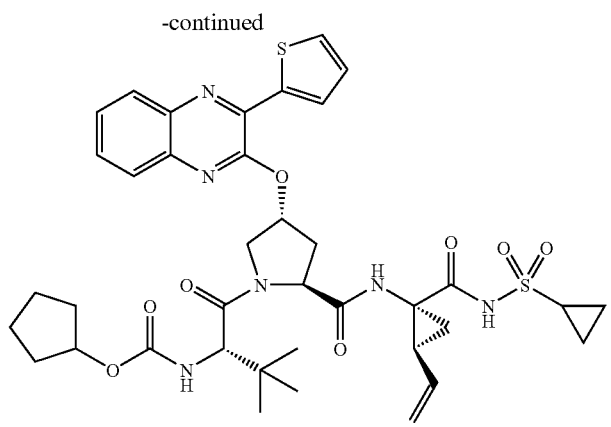

The title compound of Example 2 (0.0156 mmol) was dissolved in dichloromethane (1 m), cooled to 0° C., treated with DIPEA (27 ul, 10 eq.) followed by cyclopentylacetyl chloride (0.021 mmol). The mixture was stirred at room temperature for 0.5 to 1 hour, diluted with ethyl acetate, washed with half-sat.-aq. NaCl twice, dried (MgSO$_4$) and concentrated in vacuo. The residue was purified by silica gel chromatography (Hexans/EtOAc=2:1 to 1:1) to give the title compound (8 mg). MS(ESI): m/e 779.42 (M+H).

Example 5

Compound of Formula IV, wherein

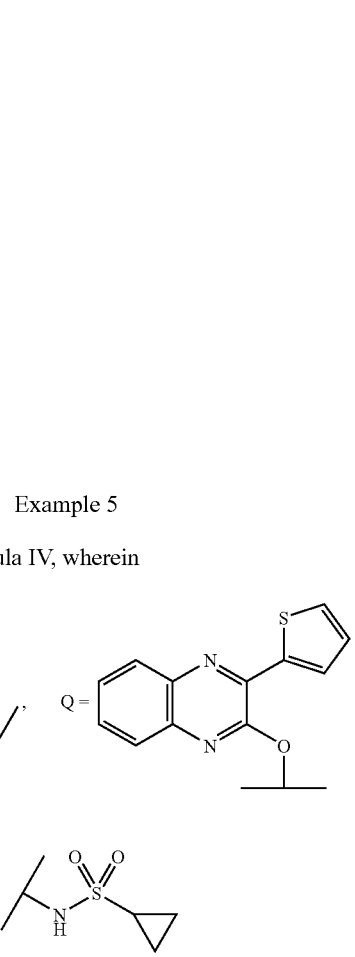

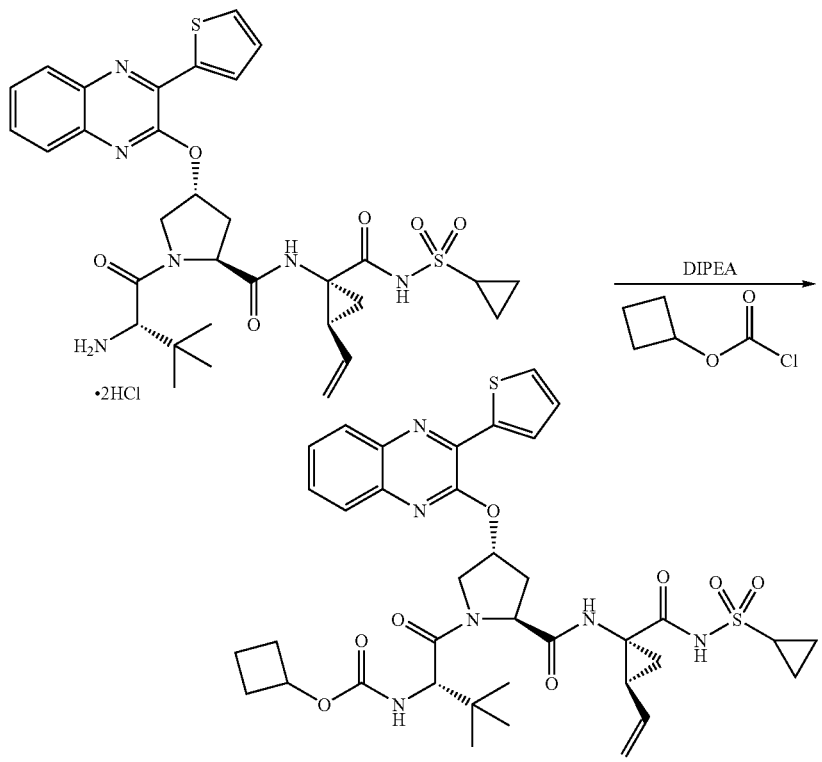

The title compound of Example 2 (0.013 mmol) was dissolved in dichloromethane (1 m), cooled to 0° C., treated with DIPEA (10 ul, 4 eq.) followed by cyclopentylacetyl chloride (0.016 mmol, 1.2 eq.). The mixture was stirred at room temperature for 0.5 to 1 hour, diluted with ethyl acetate, washed with half-sat.-aq. NaCl twice, dried (MgSO$_4$) and concentrated in vacuo. The residue was purified by silica gel chromatography (Hexans/EtOAc=2:1 to 1:1) to give the title compound (8 mg). MS(ESI): m/e 765.29 (M+H).

Example 6

Compound of Formula IV, wherein

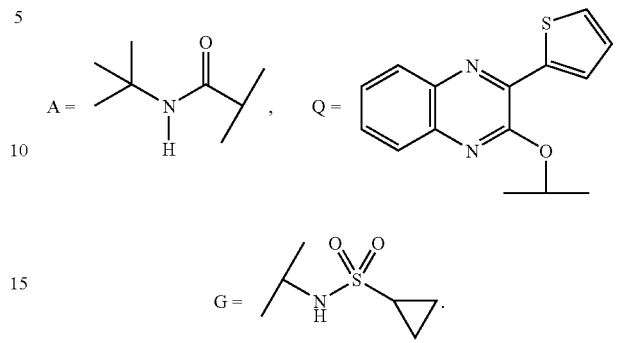

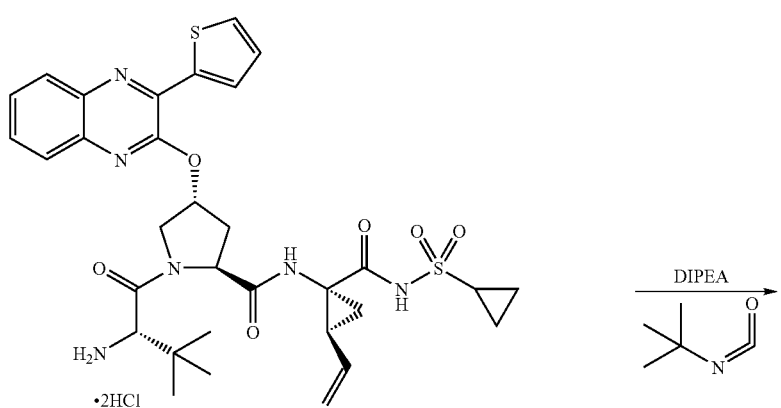

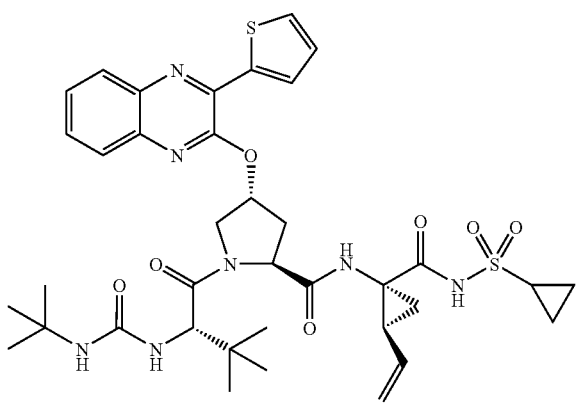

The title compound of Example 2 (0.01 mmol) was dissolved in dichloromethane (1 m), cooled to 0° C., treated with DIPEA (10 ul, 4 eq.) followed by cyclopentylacetyl chloride (1.5 to 2 eq.). The mixture was stirred at room temperature for 20 hours, diluted with ethyl acetate, washed with half-sat.-aq. NaCl twice, dried (MgSO$_4$) and concentrated in vacuo. The residue was purified by silica gel chromatography (Hexans/EtOAc=2:1 to 1:1) to give the title compound (3 mg). MS(ESI): m/e 766.30 (M+H). Example nthetic methods described in Scheme 1 to Scheme 11 and/or following the procedures described in examples 1 to Example 6.

Example 7

Compound of Formula IV, wherein

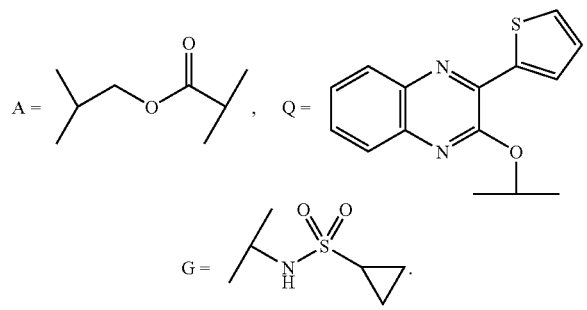

Was prepared by the same procedure as described in Example 4. MS (ESI): m/e 767.65 (M+H)

Example 8

Compound of Formula IV, wherein

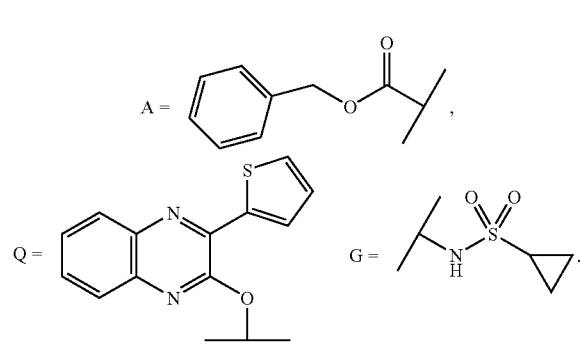

Was prepared by the same procedure as described in Example 4. MS (ESI): m/e 801.65 (M+H)

Example 9

Compound of Formula IV, wherein

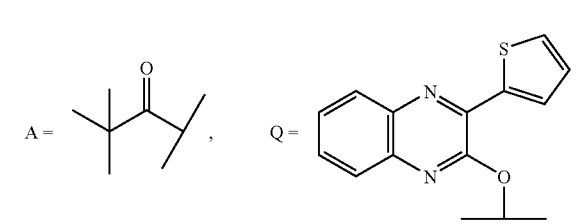

-continued

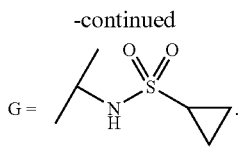

Was prepared by the same procedure as described in Example 4. MS (ESI): m/e 751.51 (M+H)

Example 10

Compound of Formula IV, wherein

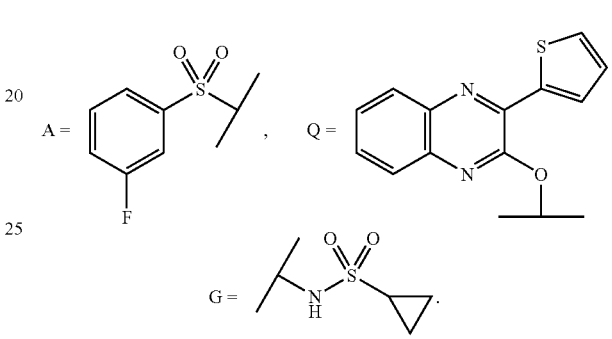

Was prepared by the same procedure as described in Example 4. MS (ESI): m/e 825.47 (M+H)

Example 11

Compound of Formula IV, wherein

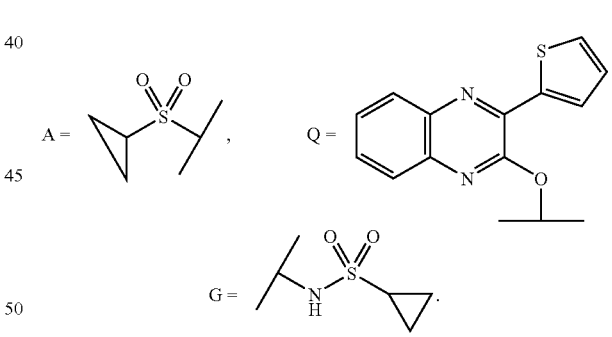

Was prepared by the same procedure as described in Example 4. MS (ESI): m/e 771.46 (M+H)

Example 12

Compound of Formula IV, wherein

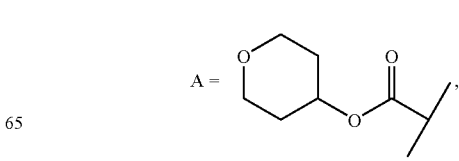

-continued

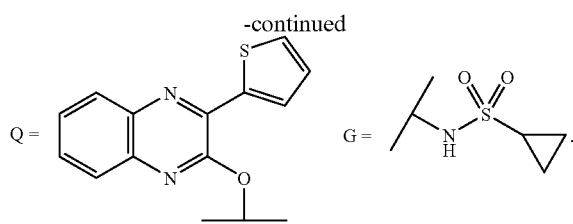

Was prepared by the same procedure as described in Example 4. MS (ESI): m/e 794.47

Example 13 to 129 can be made by synthetic methods described in Scheme 1 to Scheme 11 or by the procedures described in examples 1 to Example 6.

Representative compounds of the invention show particularly advantageous biological activity in enzyme inhibition and cell-based replicon assays for HCV activity. Such assays are known in the art and include, for example, those delineated in US 2004/0180815; US 2004/0266669; US 2005/50192212; each incorporated by reference.

What is claimed:
1. A compound of Formula I:

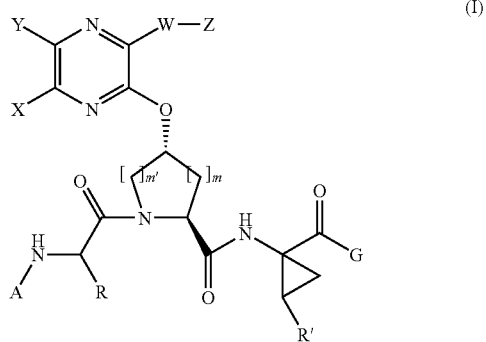

Wherein
A is selected from $-(C=O)-O-R_1$, $-(C=O)-R_2$, $-C(=O)-NH-R_2$, or $-S(O)_2-R_1$, $-S(O)_2NHR_2$;
$R_1$ is selected from the group consisting of:
(i) aryl; substituted aryl; heteroaryl; substituted heteroaryl;
(ii) heterocycloalkyl or substituted heterocycloalkyl;
(iii) $-C_1-C_8$ alkyl, $-C_2-C_8$ alkenyl, or $-C_2-C_8$ alkynyl containing 0, 1, 2, or 3 heteroatoms selected from O, S, or N; substituted $-C_1-C_8$ alkyl, substituted $-C_2-C_8$ alkenyl, or substituted $-C_2-C_8$ alkynyl containing 0, 1, 2, or 3 heteroatoms selected from O, S or N; $-C_3-C_{12}$ cycloalkyl, or substituted $-C_3-C_{12}$ cycloalkyl; $-C_3-C_{12}$ cycloalkenyl, or substituted $-C_3-C_{12}$ cycloalkenyl;
$R_2$ is independently selected from the group consisting of:
(i) hydrogen;
(ii) aryl; substituted aryl; heteroaryl; substituted heteroaryl;
(iii) heterocycloalkyl or substituted heterocycloalkyl;
(iv) $-C_1-C_8$ alkyl, $-C_2-C_8$ alkenyl, or $-C_2-C_8$ alkynyl containing 0, 1, 2, or 3 heteroatoms selected from O, S, or N; substituted $-C_1-C_8$ alkyl, substituted $-C_2-C_8$ alkenyl, or substituted $-C_2-C_8$ alkynyl containing 0, 1, 2, or 3 heteroatoms selected from O, S or N; $-C_3-C_{12}$ cycloalkyl, or substituted $-C_3-C_{12}$ cycloalkyl; $-C_3-C_{12}$ cycloalkenyl, or substituted $-C_3-C_{12}$ cycloalkenyl;

R and R' are independently selected from the group consisting of:
(i) $-C_1-C_8$ alkyl, $-C_2-C_8$ alkenyl, or $-C_2-C_8$ alkynyl containing 0, 1, 2, or 3 heteroatoms selected from O, S, or N; substituted $-C_1-C_8$ alkyl, substituted $-C_2-C_8$ alkenyl, or substituted $-C_2-C_8$ alkynyl containing 0, 1, 2, or 3 heteroatoms selected from O, S or N; $-C_3-C_{12}$ cycloalkyl, or substituted $-C_3-C_{12}$ cycloalkyl; $-C_4-C_{12}$ alkylcycloalkyl, or substituted $-C_4-C_{12}$ alkylcycloalkyl; $-C_3-C_{12}$ cycloalkenyl, or substituted $-C_3-C_{12}$ cycloalkenyl; $-C_4-C_{12}$ alkylcycloalkenyl, or substituted $-C_4-C_{12}$ alkylcycloalkenyl;
(ii) aryl; substituted aryl; heteroaryl; substituted heteroaryl;
(iii) heterocycloalkyl or substituted heterocycloalkyl;
(iv) hydrogen; deuterium;
G is selected from $-OH$, $-NHS(O)_2-R_3$, $-NH(SO_2)NR_4R_5$;
$R_3$ is selected from:
(i) aryl; substituted aryl; heteroaryl; substituted heteroaryl
(ii) heterocycloalkyl or substituted heterocycloalkyl;
(iii) $-C_1-C_8$ alkyl, $-C_2-C_8$ alkenyl, or $-C_2-C_8$ alkynyl containing 0, 1, 2, or 3 heteroatoms selected from O, S or N, substituted $-C_1-C_8$ alkyl, substituted $-C_2-C_8$ alkenyl, or substituted $-C_2-C_8$ alkynyl containing 0, 1, 2, or 3 heteroatoms selected from O, S or N; $-C_3-C_{12}$ cycloalkyl, or substituted $-C_3-C_{12}$ cycloalkyl; $-C_3-C_{12}$ cycloalkenyl, or substituted $-C_3-C_{12}$ cycloalkenyl;
$R_4$ and $R_5$ is independently selected from:
(i) hydrogen;
(ii) aryl; substituted aryl; heteroaryl; substituted heteroaryl;
(iii) heterocycloalkyl or substituted heterocycloalkyl;
(iv) $-C_1-C_8$ alkyl, $-C_2-C_8$ alkenyl, or $-C_2-C_8$ alkynyl containing 0, 1, 2, or 3 heteroatoms selected from O, S, or N; substituted $-C_1-C_8$ alkyl, substituted $-C_2-C_8$ alkenyl, or substituted $-C_2-C_8$ alkynyl containing 0, 1, 2, or 3 heteroatoms selected from O, S or N; $-C_3-C_{12}$ cycloalkyl, or substituted $-C_3-C_{12}$ cycloalkyl; $-C_3-C_{12}$ cycloalkenyl, or substituted $-C_3-C_{12}$ cycloalkenyl;
X and Y taken together with the carbon atoms to which they are attached form a cyclic moiety which selected from aryl, substituted aryl, heteroaryl, or substituted heteroaryl;
W is absent, or selected from $-O-$, $-S-$, $-NH-$, $-N(Me)-$, $-C(O)NH-$, or $-C(O)N(Me)-$;
Z is selected from the groups consisting of:
Z is selected from the groups consisting of:
(i) aryl, substituted aryl;
(ii) heteroaryl, substituted heteroaryl;
(iii) $-C_3-C_{12}$ cycloalkyl, substituted $-C_3-C_{12}$ cycloalkyl, heterocycloalkyl, substituted heterocycloalkyl;
(iv) $-C_1-C_6$ alkyl containing 0, 1, 2, or 3 heteroatoms selected from O, S, or N, optionally substituted with one or more substituent selected from halogen, aryl, substituted aryl, heteroaryl, or substituted heteroaryl;
(v) $-C_2-C_6$ alkenyl containing 0, 1, 2, or 3 heteroatoms selected from O, S, or N, optionally substituted with one or more substituent selected from halogen, aryl, substituted aryl, heteroaryl, or substituted heteroaryl;
(vi) $-C_2-C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;

W-Z taken together, is —CN, —N₃, halogen, —NH—N=CH(R₂), where R₂ is as previously defined
m=0, 1, or 2;
m'=1 or 2.

2. The compound of claim 1, wherein the compound is of Formula II:

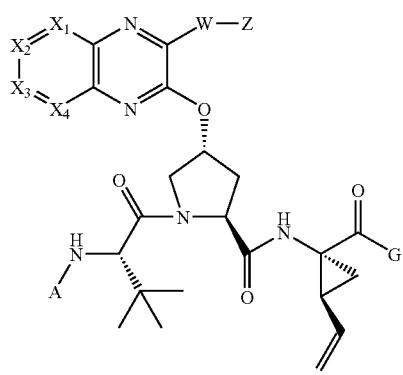

where A, G, W, Z are as previously defined.

where $X_1$-$X_4$ are independently selected from —$CR_6$ and N, wherein $R_6$ is independently selected from:

(i) hydrogen; halogen; —$NO_2$; —CN;

(ii) -M-$R_4$, M is O, S, NH, where $R_4$ is as previously defined;

(iii) $NR_4R_5$, where $R_4$ and $R_5$ are as previously defined;

(iv) —$C_1$-$C_8$ alkyl, —$C_2$-$C_8$ alkenyl, or —$C_2$-$C_8$ alkynyl containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

(v) aryl; substituted aryl; heteroaryl; substituted heteroaryl;

(vi) heterocycloalkyl or substituted heterocycloalkyl;

where A, G, W, Z are as previously defined.

3. A compound according to claim 1 which is selected from compounds of Formula IV, table 1

TABLE 1

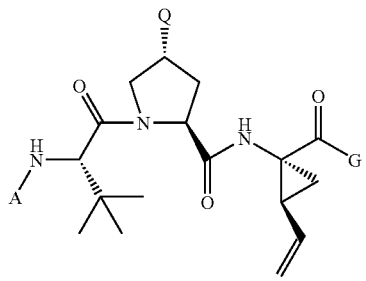

(IV)

| Example# | A | Q | G |
|---|---|---|---|
| 1 | ![tBu ester] | ![quinoxaline-thiophene-O] | —OH |
| 2 | ![tBu ester] | ![quinoxaline-thiophene-O] | ![cyclopropylsulfonamide] |
| 3 | H | ![quinoxaline-thiophene-O] | ![cyclopropylsulfonamide] |

TABLE 1-continued
(IV)
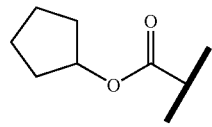
| Example# | A | Q | G |
|---|---|---|---|
| 4 | 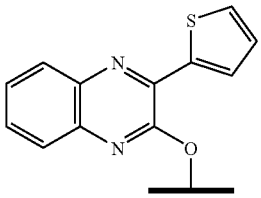 | 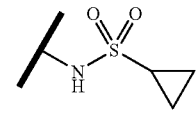 | 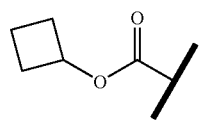 |
| 5 | 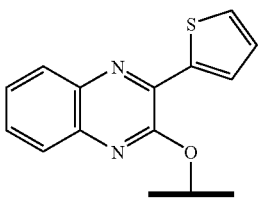 | 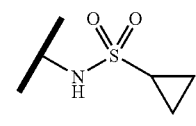 | 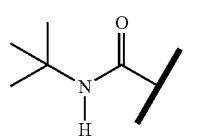 |
| 6 | 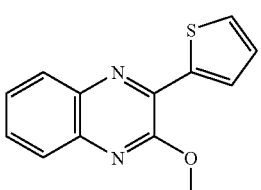 | 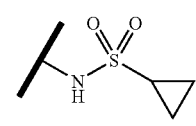 | 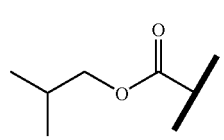 |
| 7 | 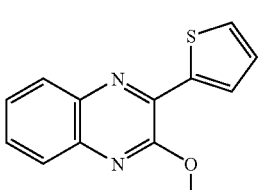 | 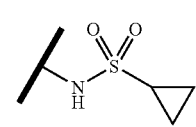 | 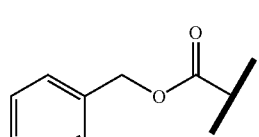 |
| 8 | 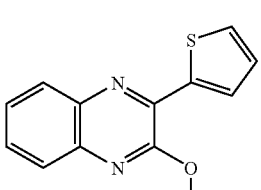 | 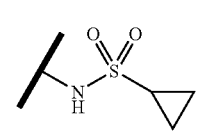 | 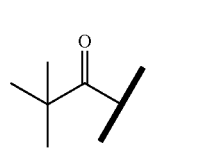 |
| 9 | 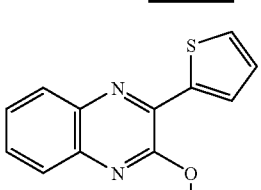 | 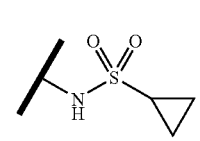 | |

TABLE 1-continued
(IV)
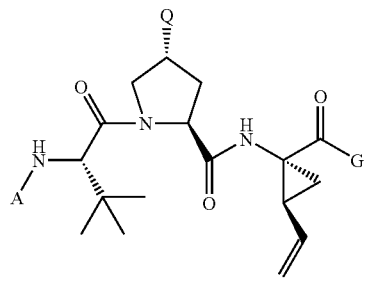
| Example# | A | Q | G |
|---|---|---|---|
| 10 | 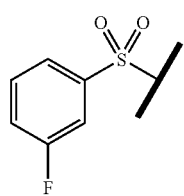 | 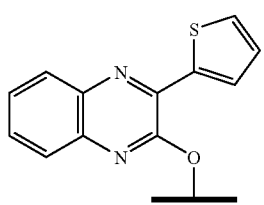 | 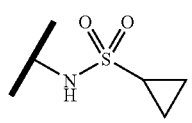 |
| 11 | 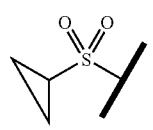 | 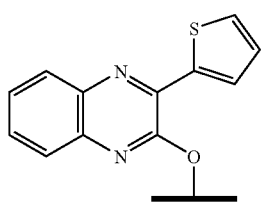 | 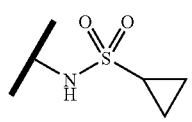 |
| 12 | 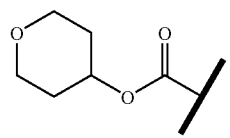 | 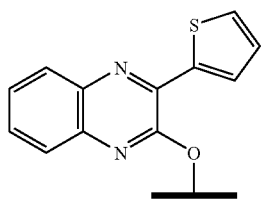 | 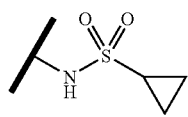 |
| 13 | 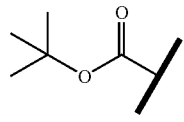 | 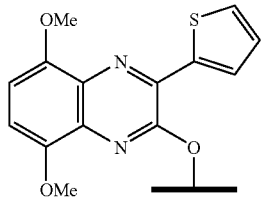 | —OH |
| 14 | 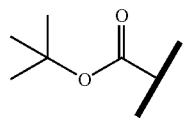 | 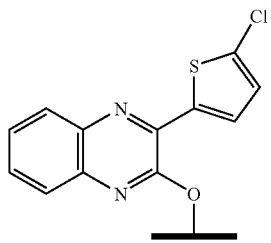 | —OH |

TABLE 1-continued
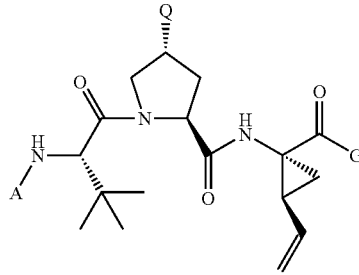
(IV)
| Example# | A | Q | G |
|---|---|---|---|
| 15 | 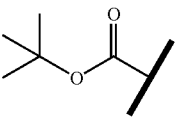 | 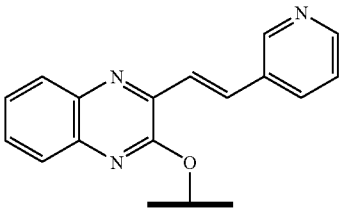 | —OH |
| 16 | 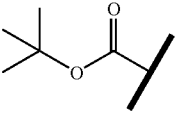 | 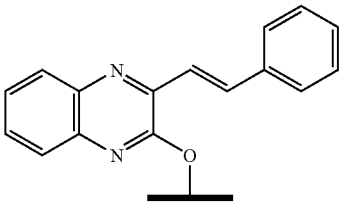 | —OH |
| 17 | 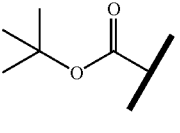 | 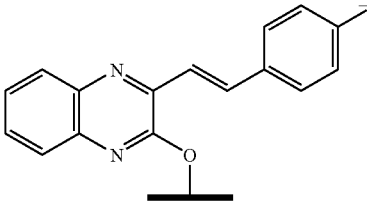 | —OH |
| 18 | 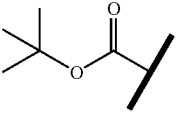 | 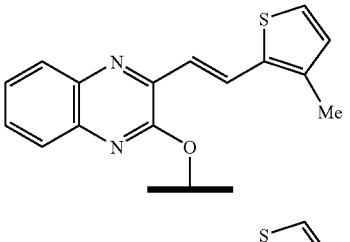 | —OH |
| 19 | 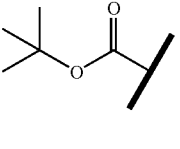 | 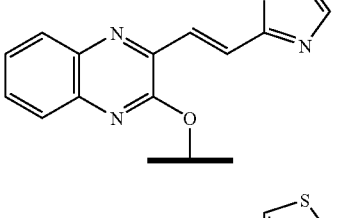 | —OH |
| 20 | 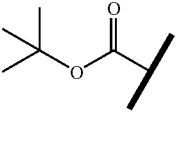 | 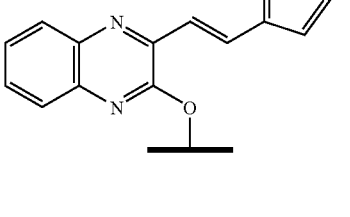 | —OH |

TABLE 1-continued
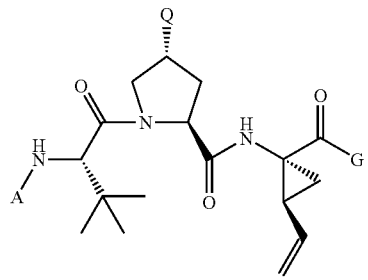
(IV)
| Example# | A | Q | G |
|---|---|---|---|
| 21 | | | —OH |
| 22 | | | —OH |
| 23 | | | —OH |
| 24 | | | —OH |
| 25 | | | —OH |
| 26 | | | —OH |

TABLE 1-continued
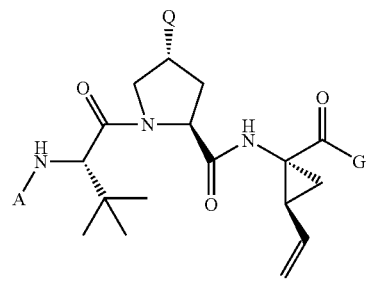
(IV)
| Example# | A | Q | G |
|---|---|---|---|
| 27 | 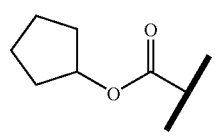 | 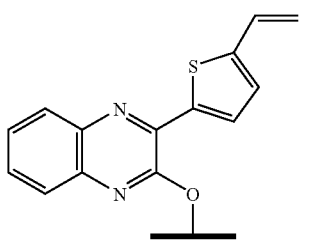 | —OH |
| 28 | 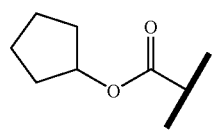 | 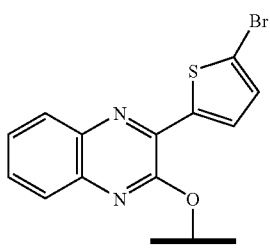 | —OH |
| 29 | 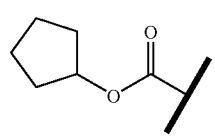 | 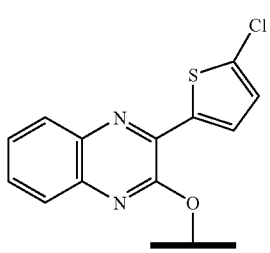 | —OH |
| 30 | 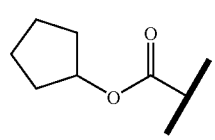 | 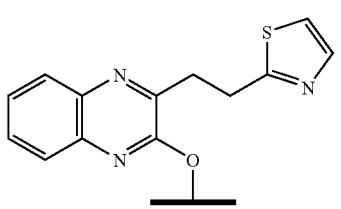 | —OH |
| 31 | 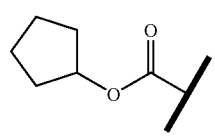 | 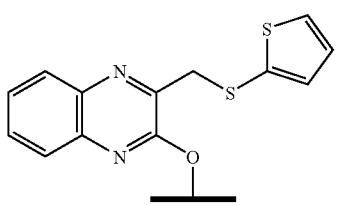 | —OH |

TABLE 1-continued
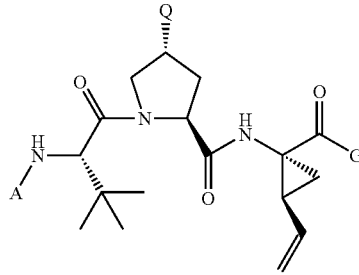
(IV)
| Example# | A | Q | G |
|---|---|---|---|
| 32 | 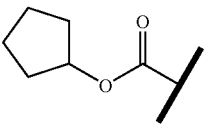 | 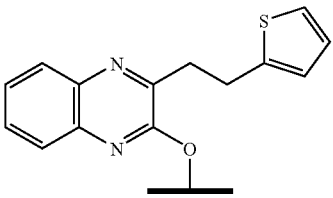 | —OH |
| 33 | 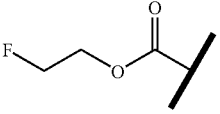 | 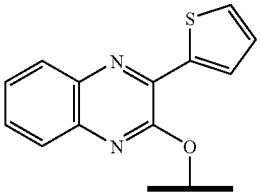 | —OH |
| 34 | 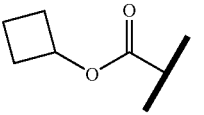 | 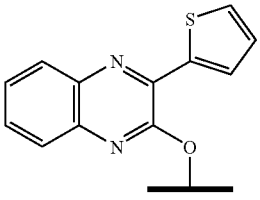 | —OH |
| 35 | 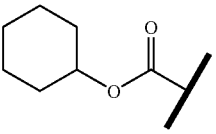 | 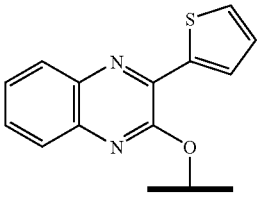 | —OH |
| 36 | 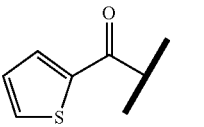 | 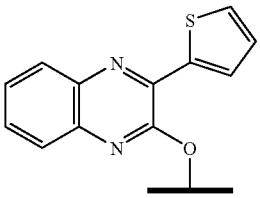 | —OH |
| 37 | 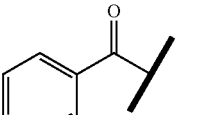 | 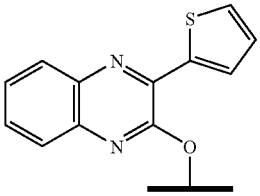 | —OH |

TABLE 1-continued

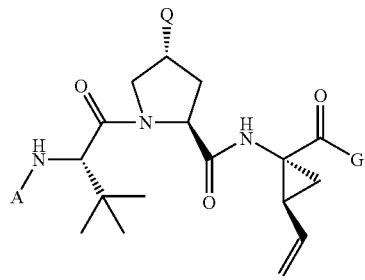

(IV)

| Example# | A | Q | G |
|---|---|---|---|
| 38 | pyrrole-2-carbonyl | 3-(thiophen-2-yl)quinoxalin-2-yloxy | —OH |
| 39 | 1-methylpyrrole-2-carbonyl | 3-(thiophen-2-yl)quinoxalin-2-yloxy | —OH |
| 40 | furan-3-carbonyl | 3-(thiophen-2-yl)quinoxalin-2-yloxy | —OH |
| 41 | 2,5-dimethylpyrrole-3-carbonyl | 3-(thiophen-2-yl)quinoxalin-2-yloxy | —OH |
| 42 | 1-ethyl-3-methylpyrazole-5-carbonyl | 3-(thiophen-2-yl)quinoxalin-2-yloxy | —OH |
| 43 | 1H-pyrazole-4-carbonyl | 3-(thiophen-2-yl)quinoxalin-2-yloxy | —OH |

TABLE 1-continued (IV)

| Example# | A | Q | G |
|---|---|---|---|
| 44 | furan-2-carbonyl | 3-(thiophen-2-yl)quinoxalin-2-yloxy | —OH |
| 45 | 1H-pyrazole-5-carbonyl | 3-(thiophen-2-yl)quinoxalin-2-yloxy | —OH |
| 46 | thiophene-2-carbonyl | 3-(2-(thiophen-2-yl)vinyl)quinoxalin-2-yloxy | —OH |
| 47 | N-(2-fluoroethyl)acetamide | 3-(thiophen-2-yl)quinoxalin-2-yloxy | —OH |
| 48 | tert-butoxycarbonyl | 3-(thiophen-2-yl)thieno[3,4-b]pyrazin-2-yloxy | —OH |
| 49 | tert-butoxycarbonyl | 3-(2-(thiazol-2-yl)ethyl)quinoxalin-2-yloxy | N-(cyclopropylsulfonyl) |

TABLE 1-continued
(IV)
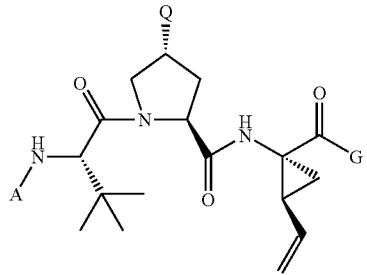
| Example# | A | Q | G |
|---|---|---|---|
| 50 | 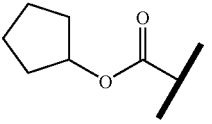 | 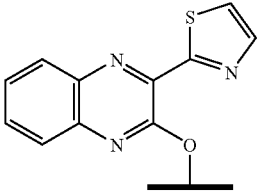 | 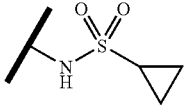 |
| 51 | 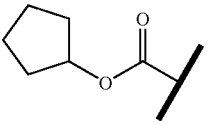 | 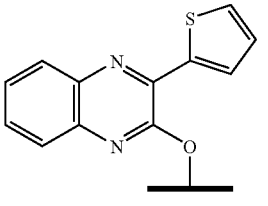 | 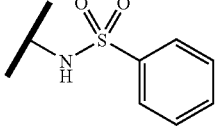 |
| 52 | 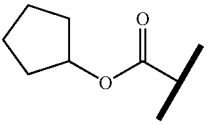 | 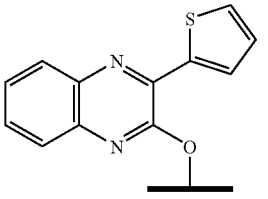 | 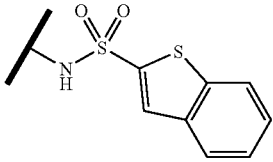 |
| 53 | 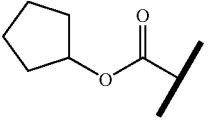 | 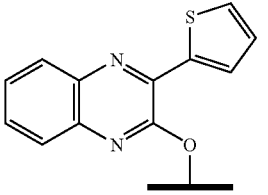 | 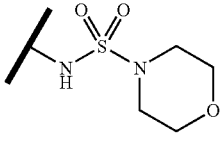 |
| 54 | 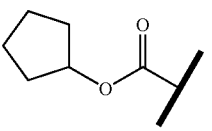 | 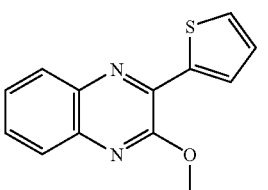 | 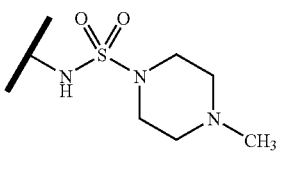 |
| 55 | 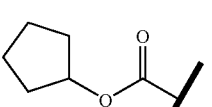 | 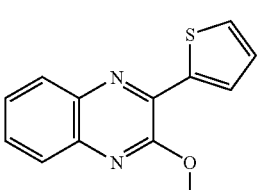 | 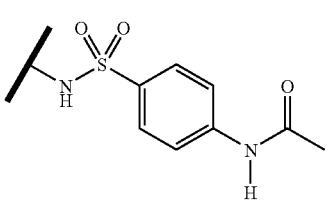 |

TABLE 1-continued
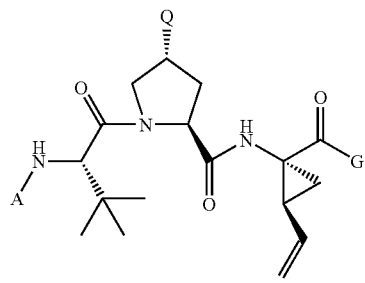
(IV)
| Example# | A | Q | G |
|---|---|---|---|
| 56 | 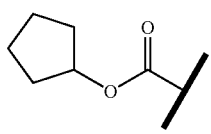 | 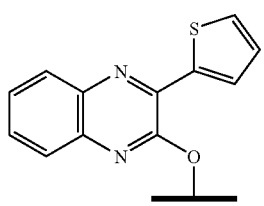 | 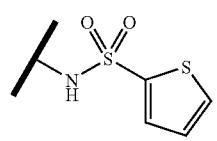 |
| 57 | 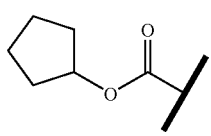 | 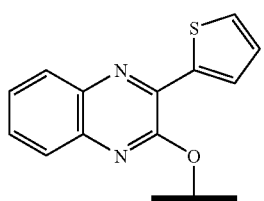 | 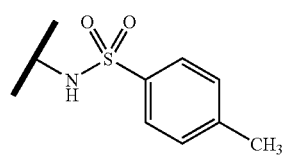 |
| 58 | 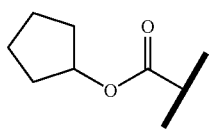 | 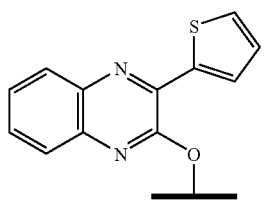 | 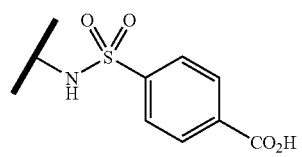 |
| 59 | 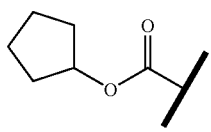 | 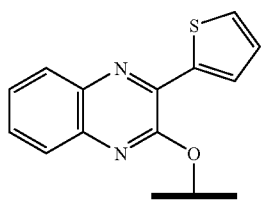 | 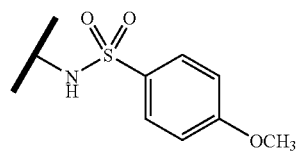 |
| 60 | 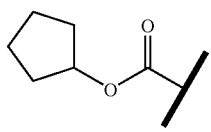 | 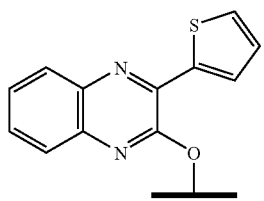 | 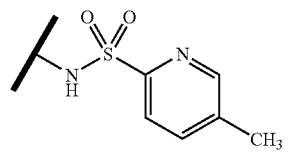 |
| 61 | 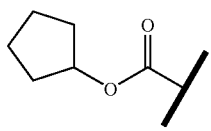 | 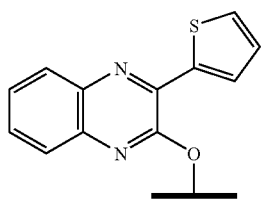 | 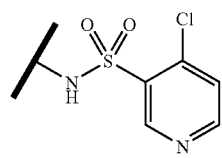 |

TABLE 1-continued
(IV)
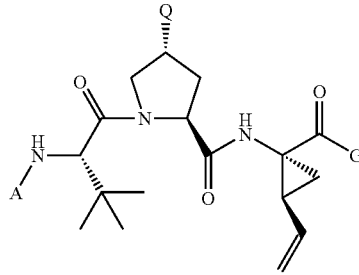
| Example# | A | Q | G |
|---|---|---|---|
| 62 | 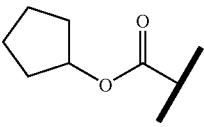 | 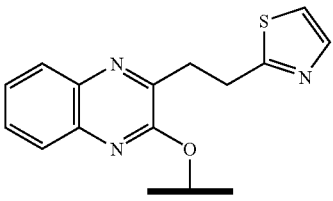 | 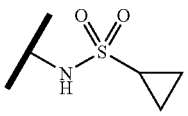 |
| 63 | 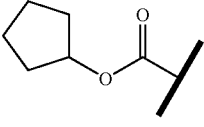 | 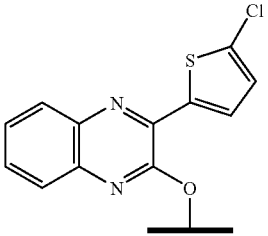 | 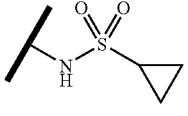 |
| 64 | 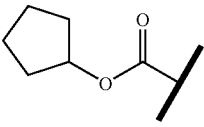 | 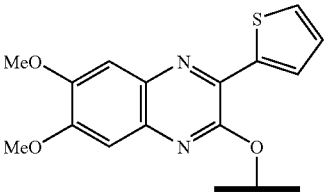 | 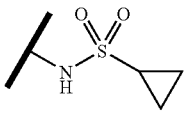 |
| 65 | 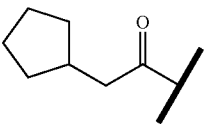 | 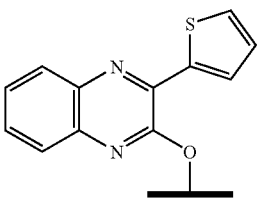 | 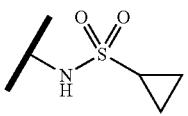 |
| 66 | 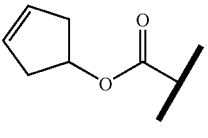 | 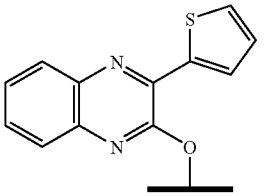 | 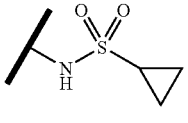 |
| 67 | 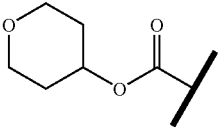 | 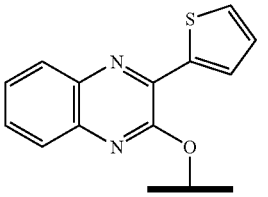 | 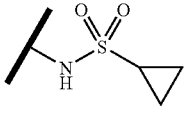 |

TABLE 1-continued
(IV)
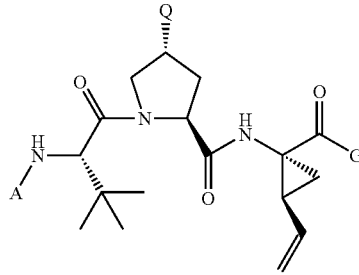
| Example# | A | Q | G |
|---|---|---|---|
| 68 | 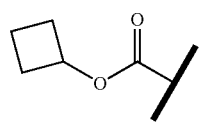 | 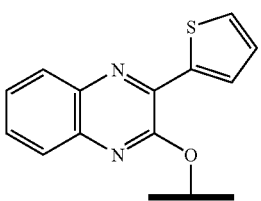 | 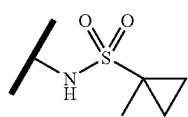 |
| 69 | 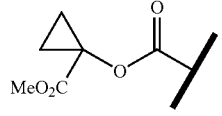 | 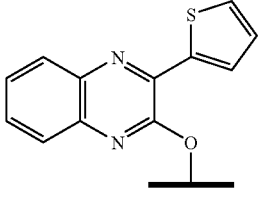 | 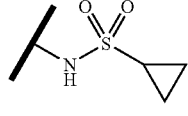 |
| 70 | 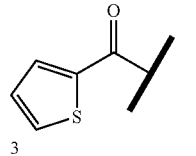 | 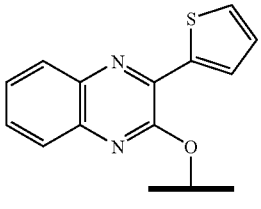 | 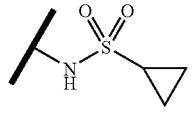 |
| 71 | 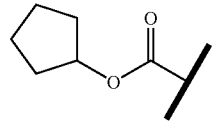 | 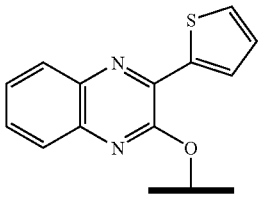 | 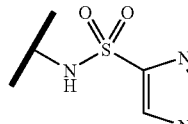 |
| 72 | 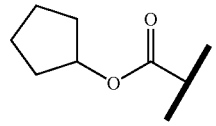 | 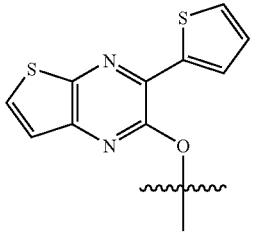 | 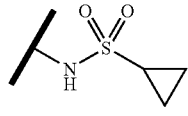 |

TABLE 1-continued
(IV)
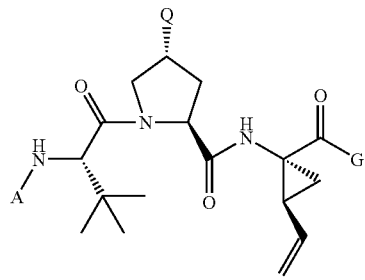
| Example# | A | Q | G |
|---|---|---|---|
| 73 | 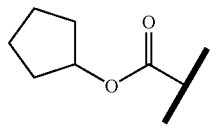 | 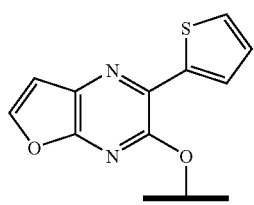 | 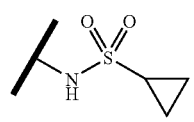 |
| 74 | 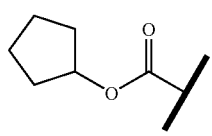 | 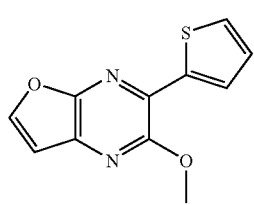 | 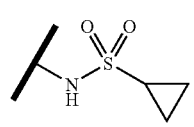 |
| 75 | 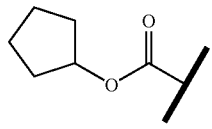 | 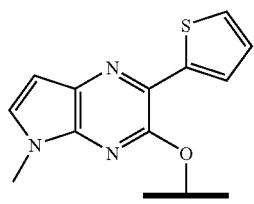 | 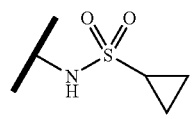 |
| 76 | 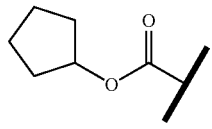 | 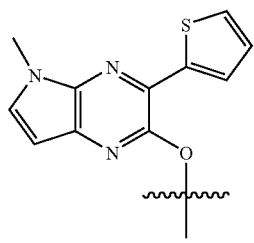 | 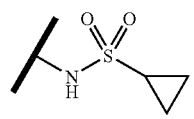 |
| 77 | 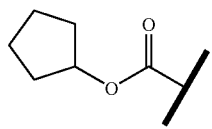 | 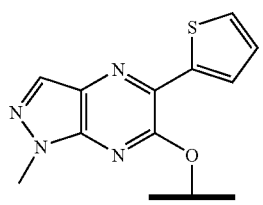 | 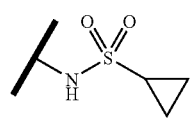 |

TABLE 1-continued
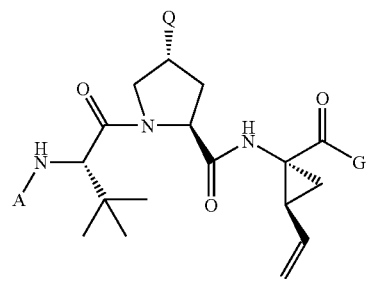
(IV)
| Example# | A | Q | G |
|---|---|---|---|
| 78 | 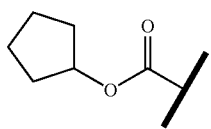 | 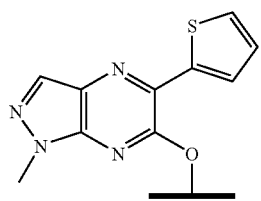 | 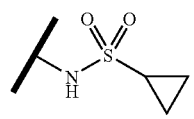 |
| 79 | 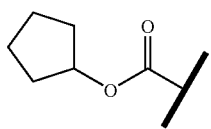 | 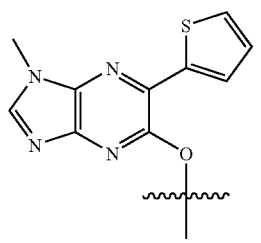 | 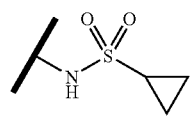 |
| 80 | 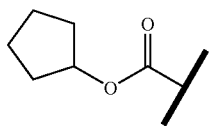 | 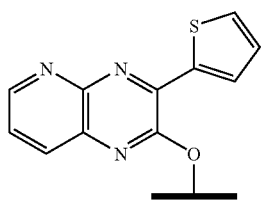 | 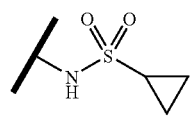 |
| 81 | 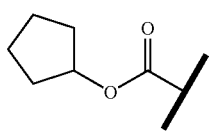 | 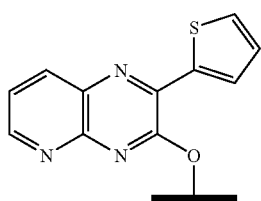 | 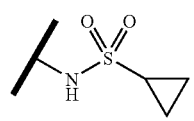 |
| 82 | 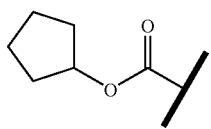 | 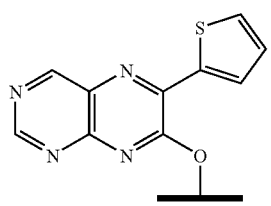 | 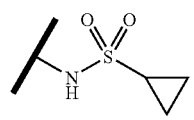 |

TABLE 1-continued
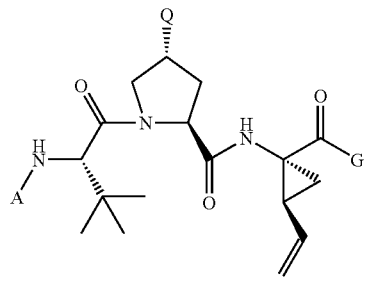
(IV)
| Example# | A | Q | G |
|---|---|---|---|
| 83 | 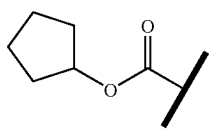 | 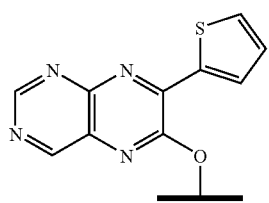 | 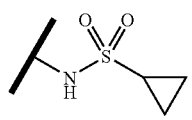 |
| 84 | 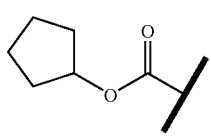 | 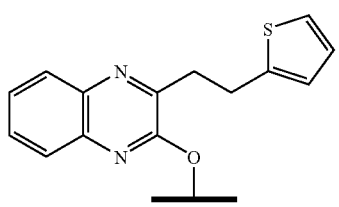 | 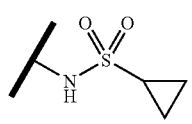 |
| 85 | 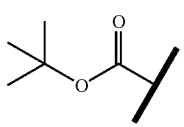 | 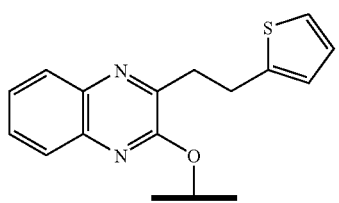 | 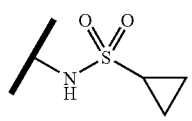 |
| 86 | 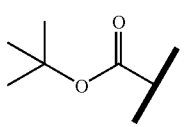 | 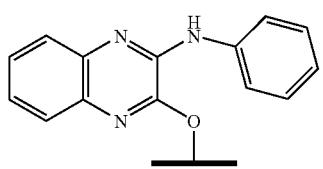 | 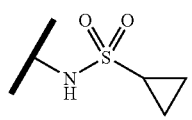 |
| 87 | 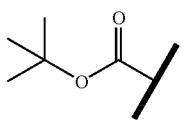 | 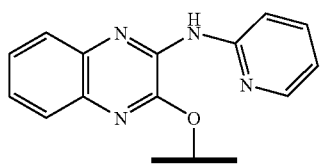 | 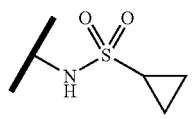 |
| 88 | 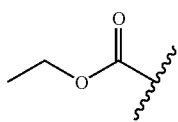 | 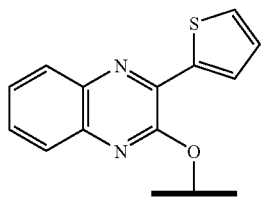 | 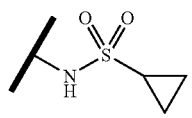 |

TABLE 1-continued
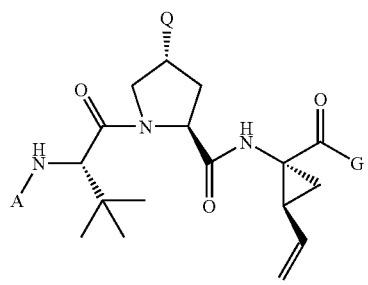
(IV)
| Example# | A | Q | G |
|---|---|---|---|
| 89 | 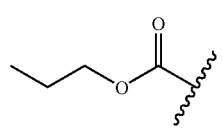 | 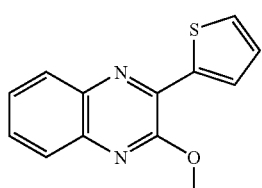 | 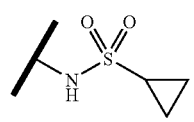 |
| 90 | 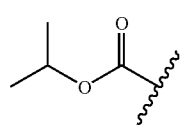 | 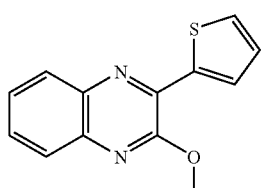 | 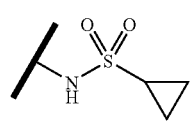 |
| 91 | 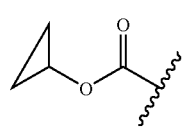 | 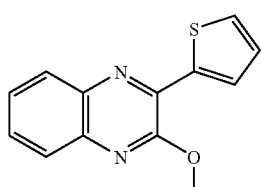 | 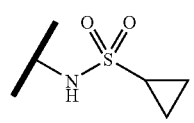 |
| 92 | 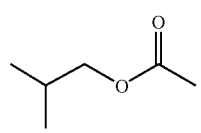 | 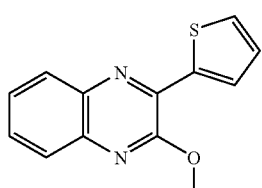 | 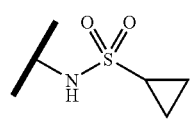 |
| 93 | 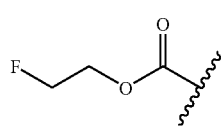 | 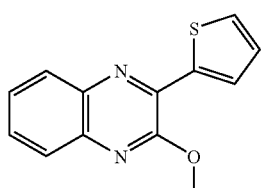 | 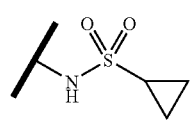 |
| 94 | 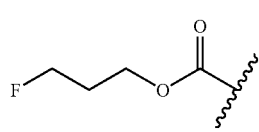 | 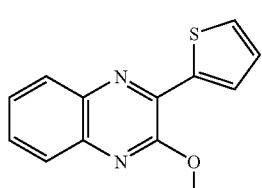 | 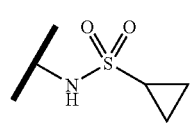 |

TABLE 1-continued
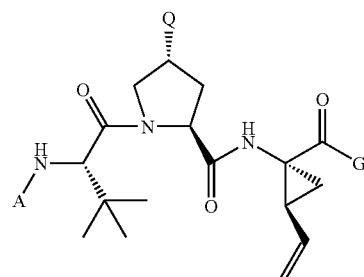
(IV)
| Example# | A | Q | G |
|---|---|---|---|
| 95 | 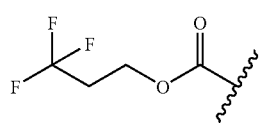 | 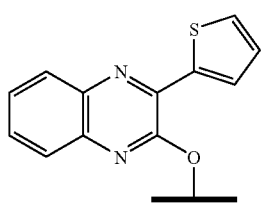 | 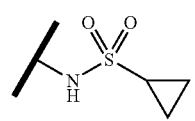 |
| 96 | 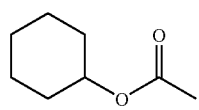 | 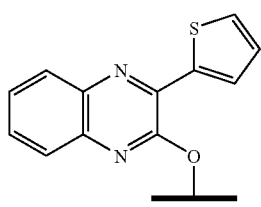 | 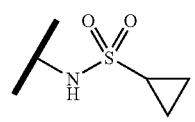 |
| 97 | 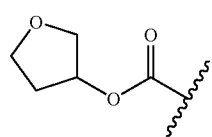 | 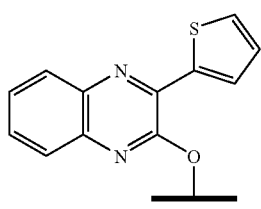 | 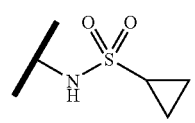 |
| 98 | 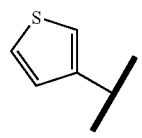 | 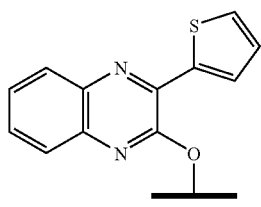 | 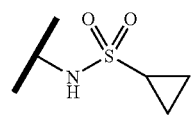 |
| 99 | 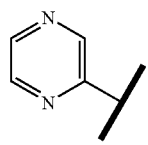 | 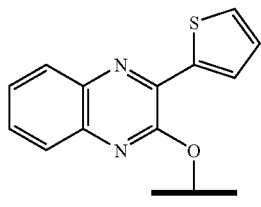 | 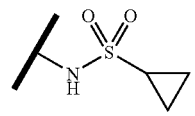 |
| 100 | 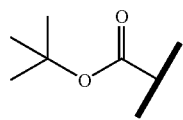 | 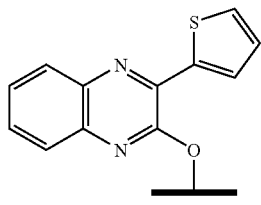 | 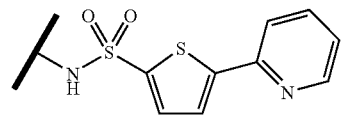 |

TABLE 1-continued
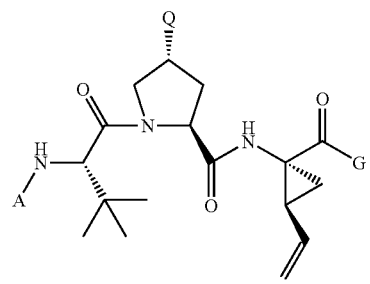
(IV)
| Example# | A | Q | G |
|---|---|---|---|
| 101 | 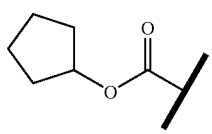 | 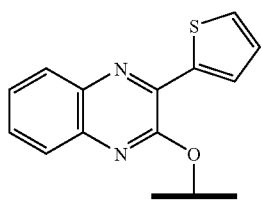 | 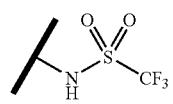 |
| 102 | 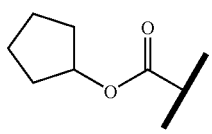 | 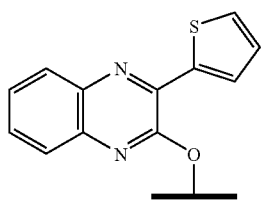 | 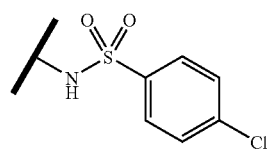 |
| 103 | 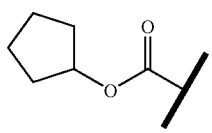 | 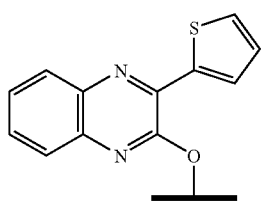 | 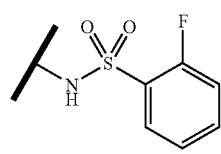 |
| 104 | 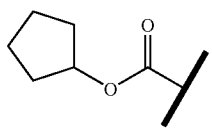 | 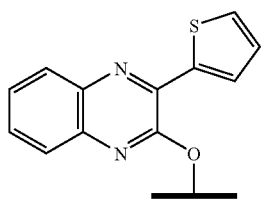 | 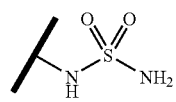 |
| 105 | 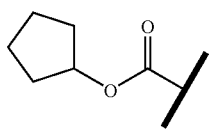 | 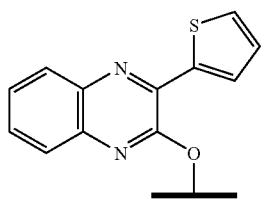 | 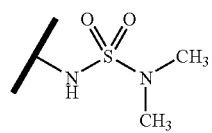 |
| 106 | 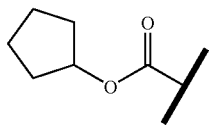 | 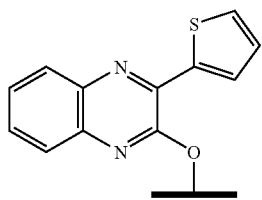 | 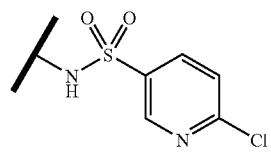 |

TABLE 1-continued
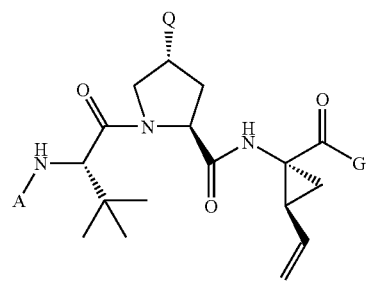
(IV)
| Example# | A | Q | G |
|---|---|---|---|
| 107 | 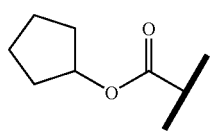 | 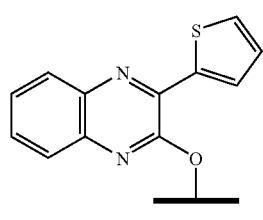 | 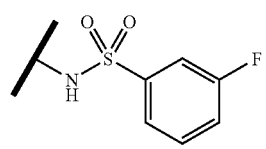 |
| 108 | 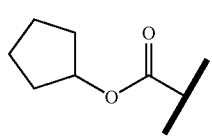 | 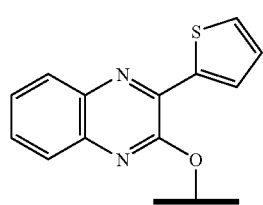 | 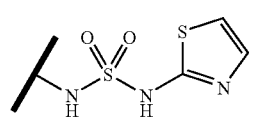 |
| 109 | 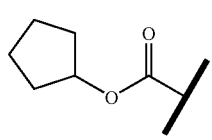 | 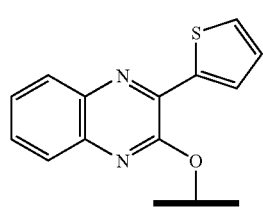 | 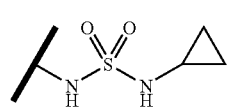 |
| 110 | 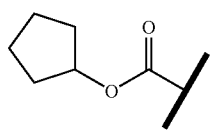 | 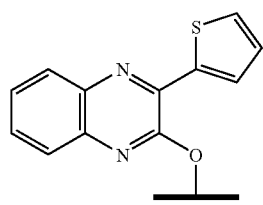 | 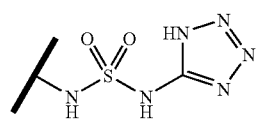 |
| 111 | 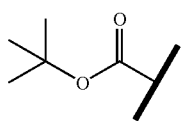 | 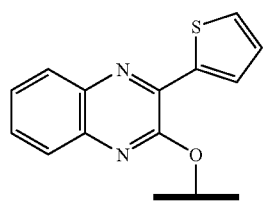 | 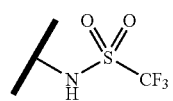 |
| 112 | 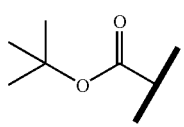 | 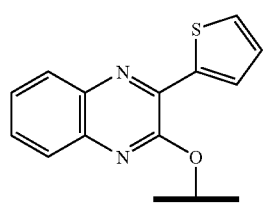 | 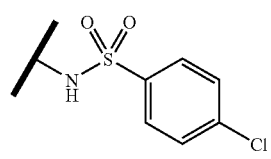 |

TABLE 1-continued
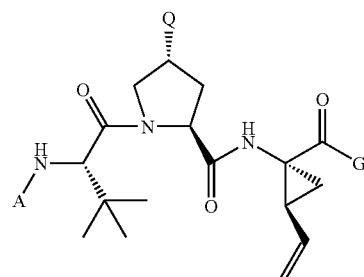
(IV)
| Example# | A | Q | G |
|---|---|---|---|
| 113 | 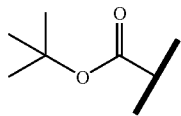 | 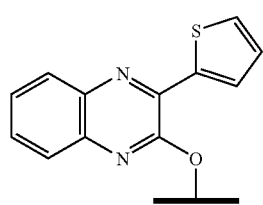 | 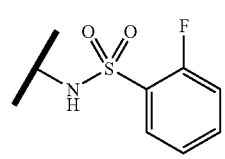 |
| 114 | 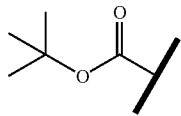 | 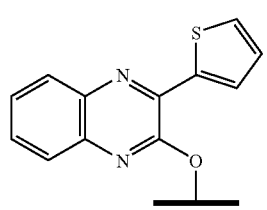 | 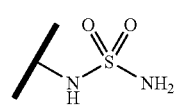 |
| 115 | 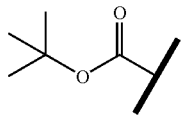 | 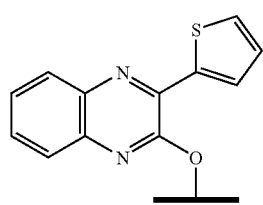 | 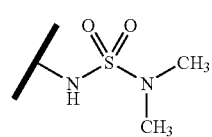 |
| 116 | 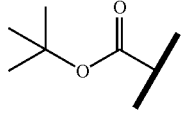 | 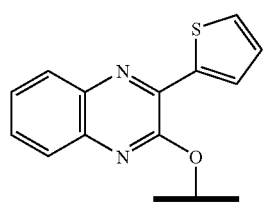 | 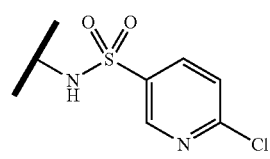 |
| 117 | 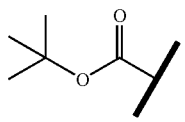 | 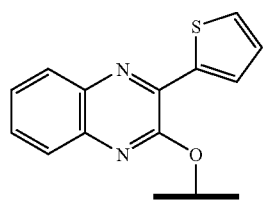 | 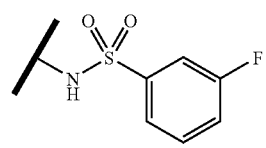 |
| 118 | 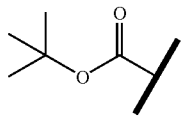 | 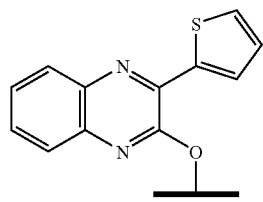 | 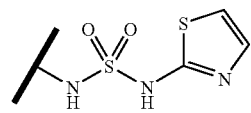 |

TABLE 1-continued
(IV)
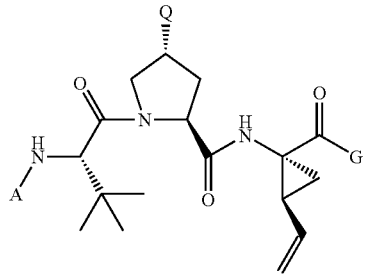
| Example# | A | Q | G |
|---|---|---|---|
| 119 | 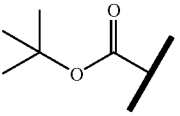 | 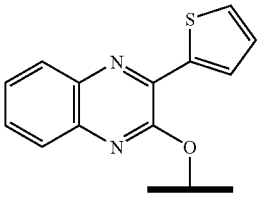 | 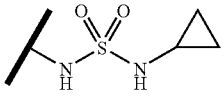 |
| 120 | 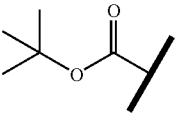 | 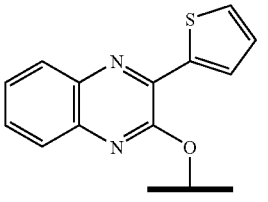 | 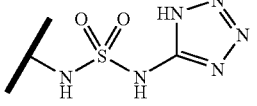 |
| 121 | 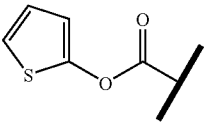 | 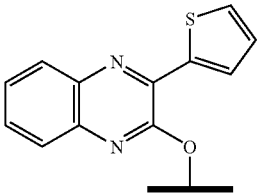 | 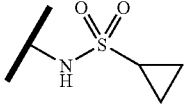 |
| 122 | 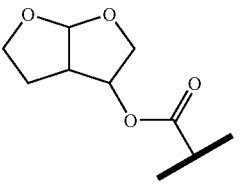 | 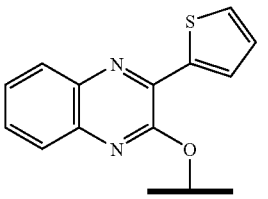 | 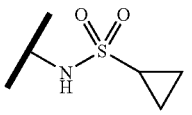 |
| 123 | 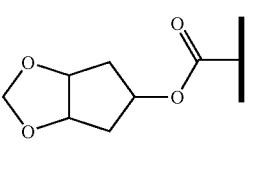 | 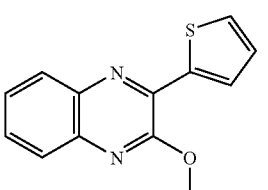 | 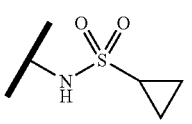 |
| 124 | 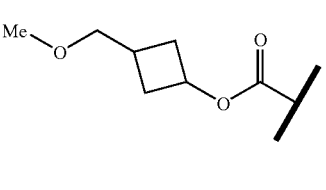 | 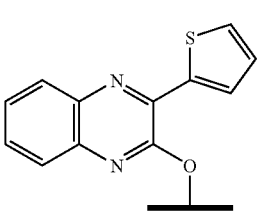 | 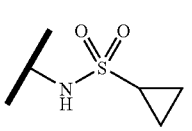 |

TABLE 1-continued
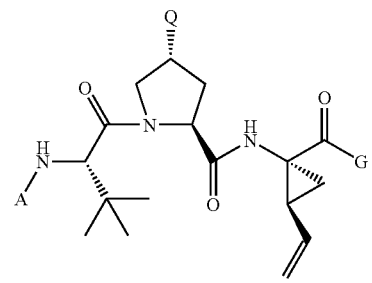
(IV)
| Example# | A | Q | G |
|---|---|---|---|
| 125 | 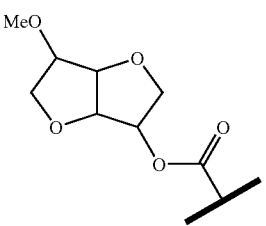 | 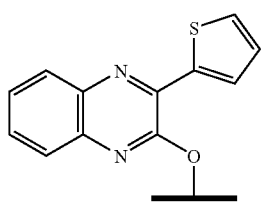 | 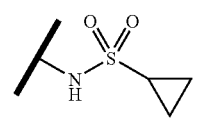 |
| 126 | 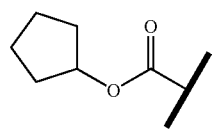 | 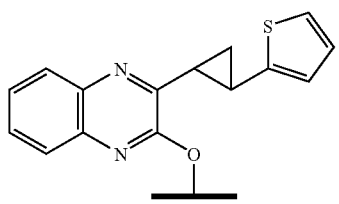 | 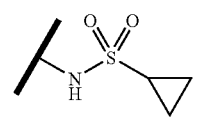 |
| 127 | 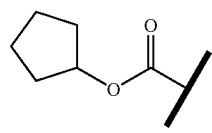 | 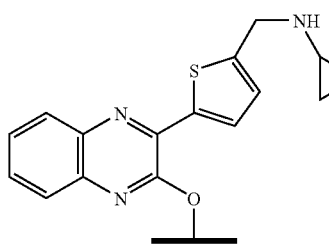 | 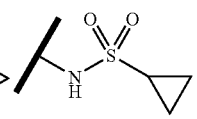 |
| 128 | 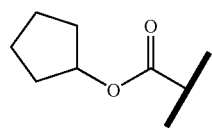 | 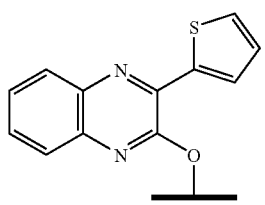 | 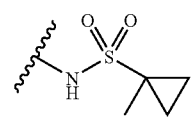 |
| 129 | 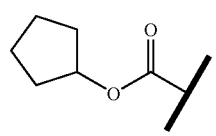 | 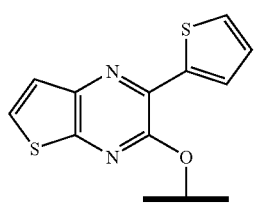 | 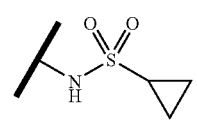 |

4. A compound of Formula IV:
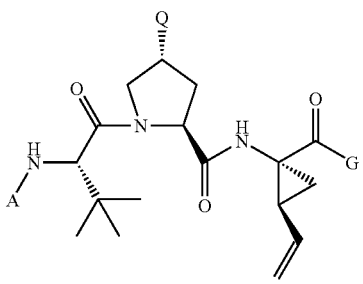
(IV)
wherein A is selected from the groups set forth in Table 2, Q is selected from the groups set forth in Table 3 and G is selected from the groups set forth in Table 4:
TABLE 2
A-Matrix
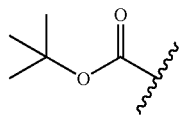
A-01
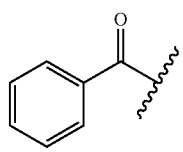
A-02
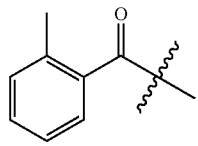
A-03
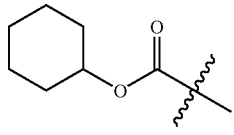
A-04
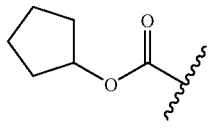
A-05
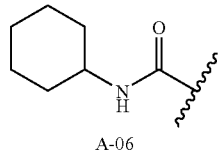
A-06
TABLE 2-continued
A-Matrix
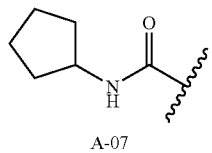
A-07
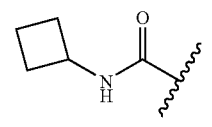
A-08
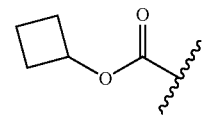
A-09
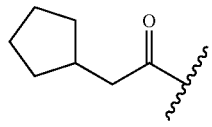
A-10
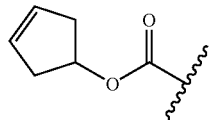
A-11
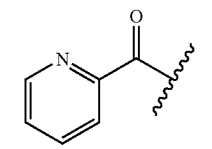
A-12
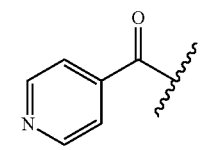
A-13
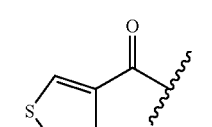
A-14
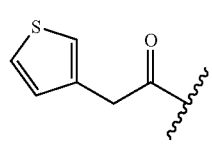
A-15

TABLE 2-continued
A-Matrix
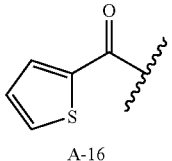
A-16
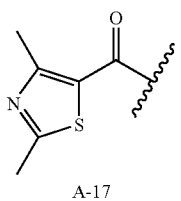
A-17
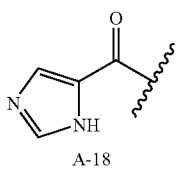
A-18
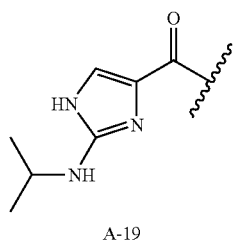
A-19
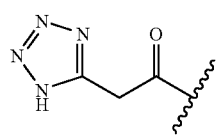
A-20
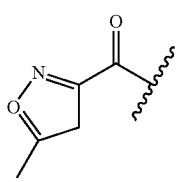
A-21
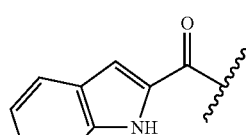
A-22
TABLE 2-continued
A-Matrix
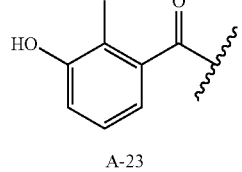
A-23
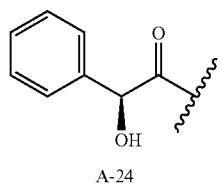
A-24
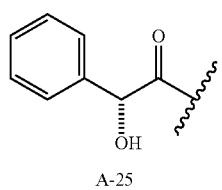
A-25
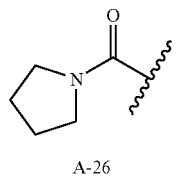
A-26
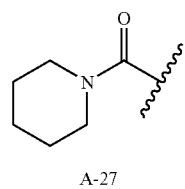
A-27
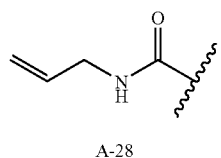
A-28
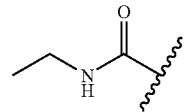
A-29
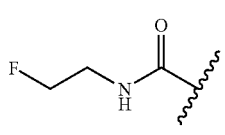
A-30

TABLE 2-continued
A-Matrix
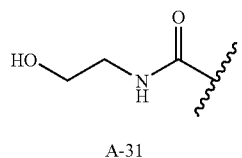
A-31
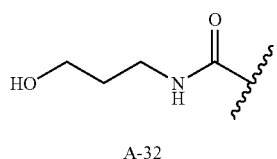
A-32
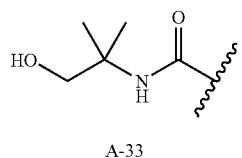
A-33
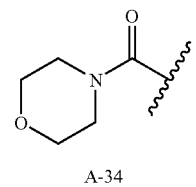
A-34
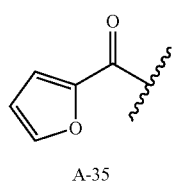
A-35
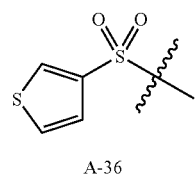
A-36
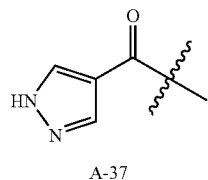
A-37
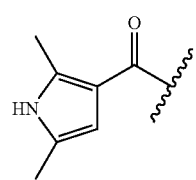
A-38
TABLE 2-continued
A-Matrix
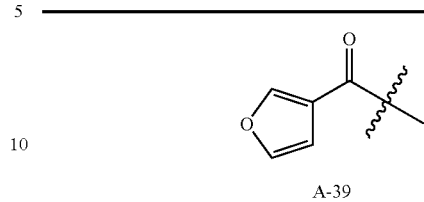
A-39
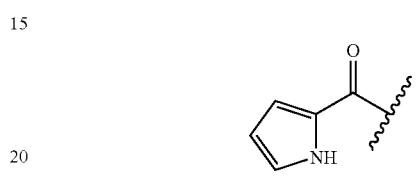
A-40
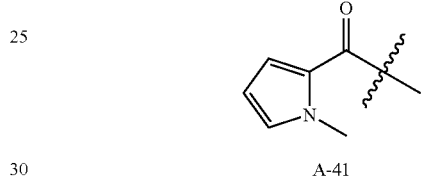
A-41
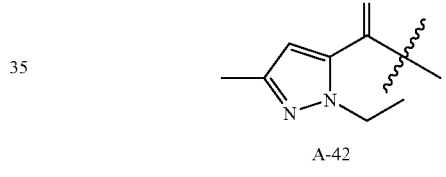
A-42
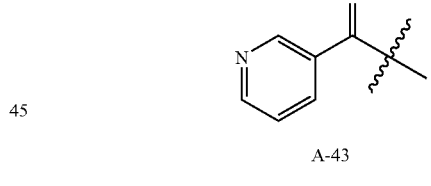
A-43
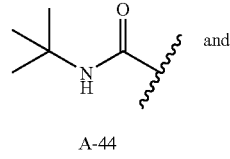 and
A-44
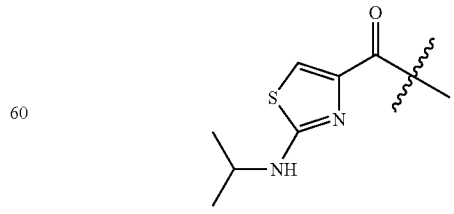
A-45

TABLE 3
Q-Matrix
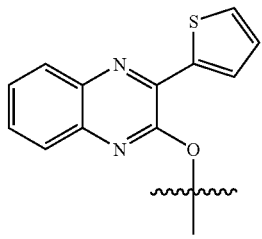
Q-01
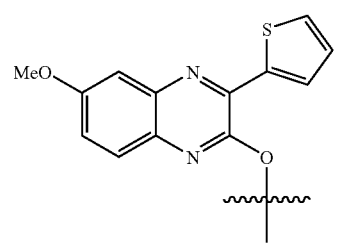
Q-02
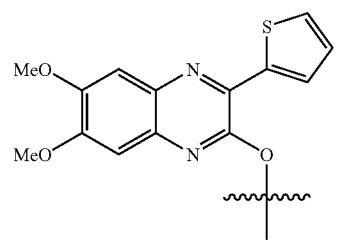
Q-03
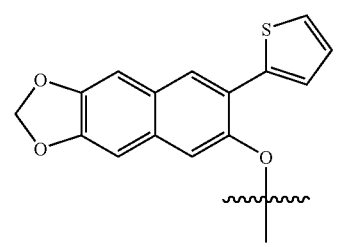
Q-04
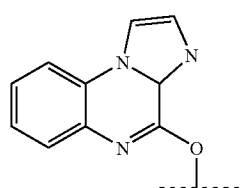
Q-05
TABLE 3-continued
Q-Matrix
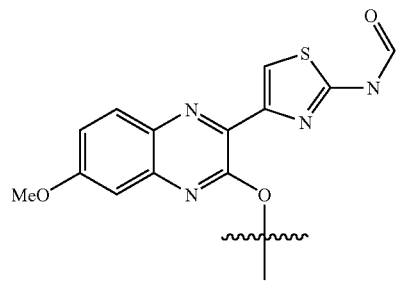
Q-06
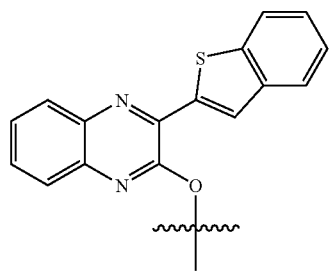
Q-07
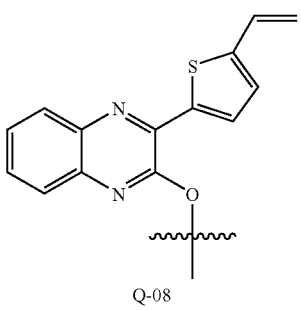
Q-08
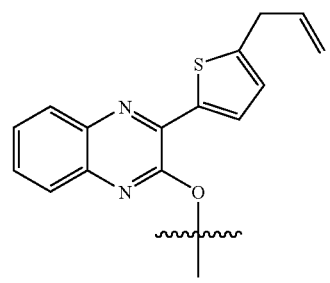
Q-09
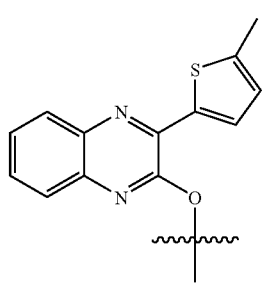
Q-10

TABLE 3-continued
Q-Matrix
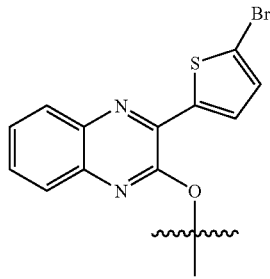
Q-11
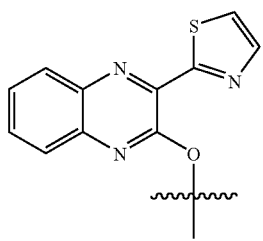
Q-12
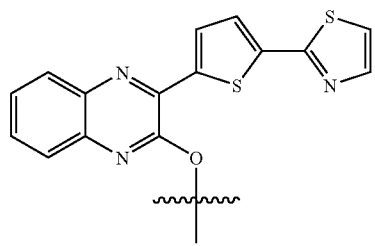
Q-13
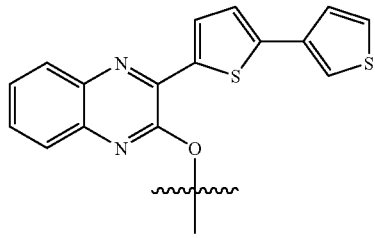
Q-14
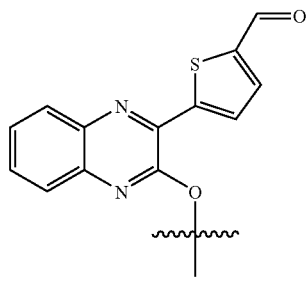
Q-15
TABLE 3-continued
Q-Matrix
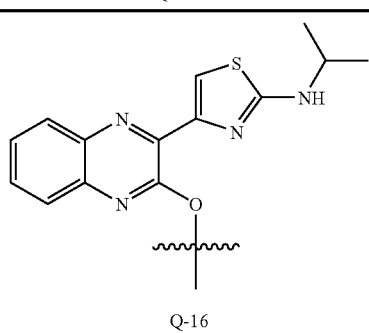
Q-16
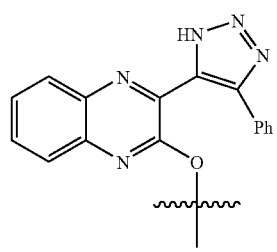
Q-17
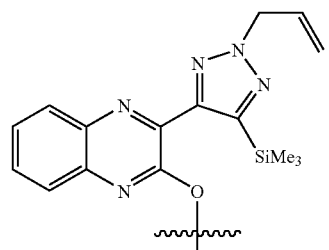
Q-18
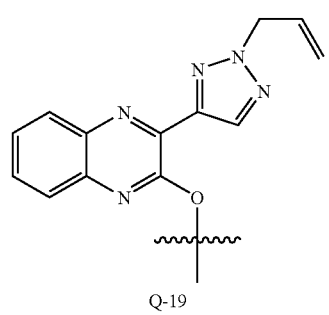
Q-19
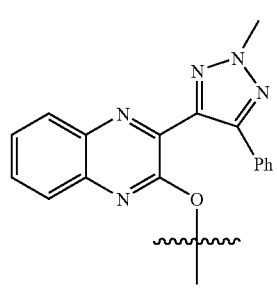
Q-20

TABLE 3-continued
Q-Matrix
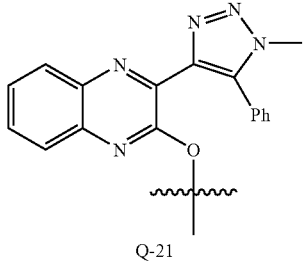
Q-21
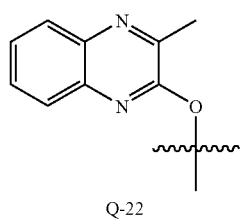
Q-22
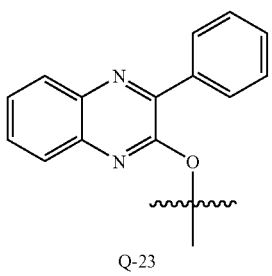
Q-23
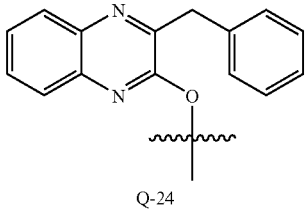
Q-24
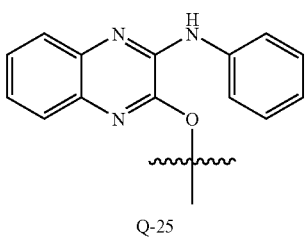
Q-25
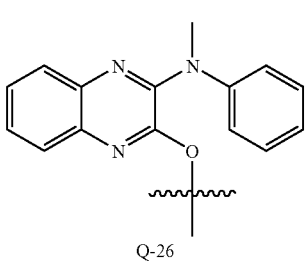
Q-26
TABLE 3-continued
Q-Matrix
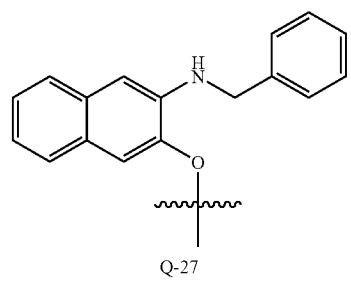
Q-27
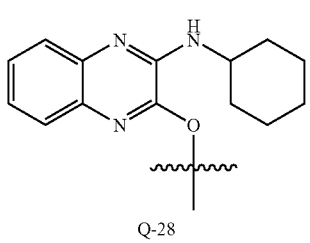
Q-28
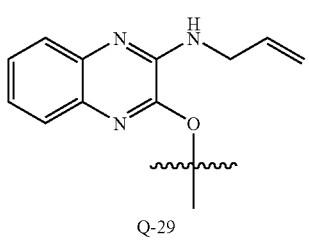
Q-29
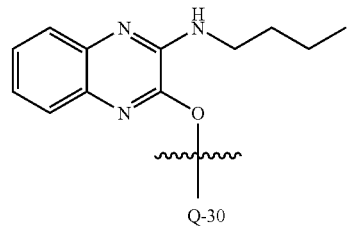
Q-30
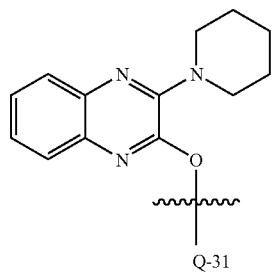
Q-31
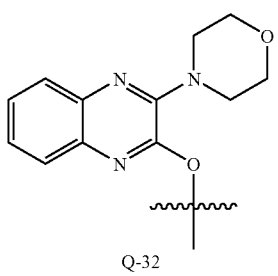
Q-32

TABLE 3-continued
Q-Matrix
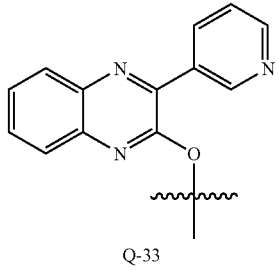
Q-33
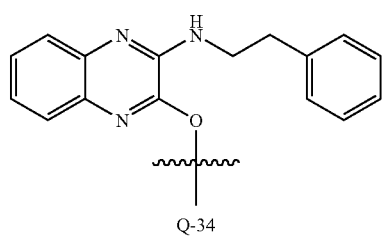
Q-34
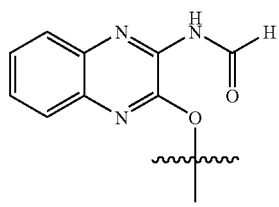
Q-35
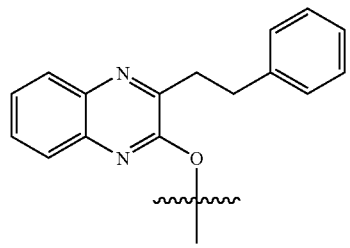
Q-37
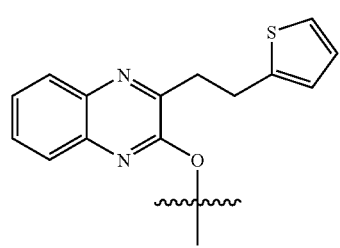
Q-38
TABLE 3-continued
Q-Matrix
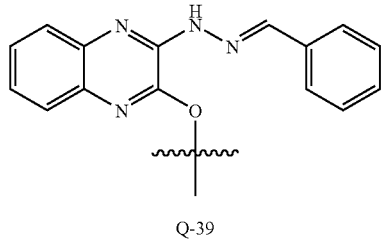
Q-39
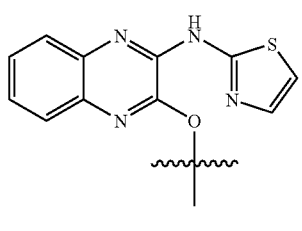
Q-40
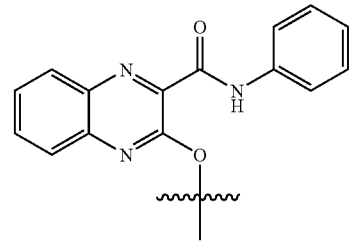
Q-41
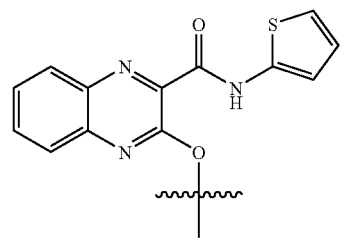
Q-42
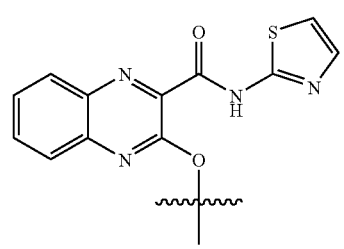
Q-43

TABLE 3-continued
Q-Matrix
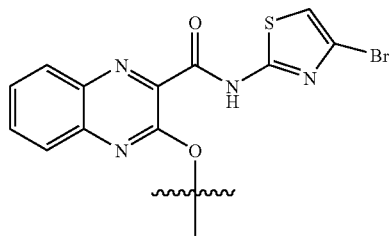
Q-44
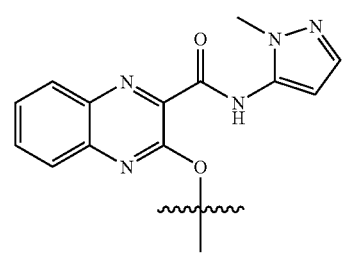
Q-45
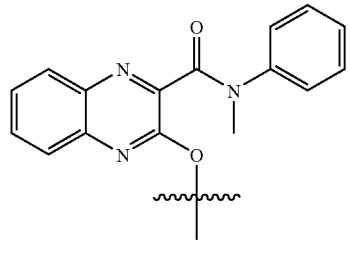
Q-46
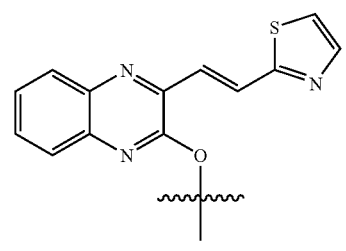
Q-47
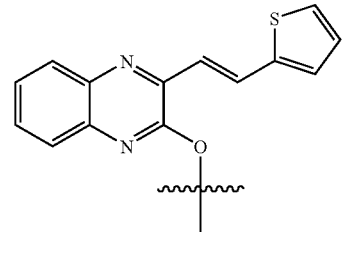
Q-48
TABLE 3-continued
Q-Matrix
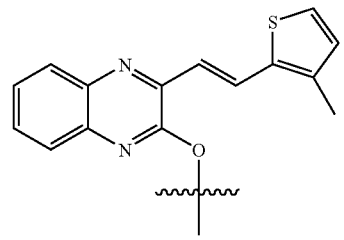
Q-49
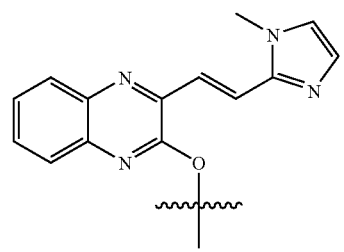
Q-50
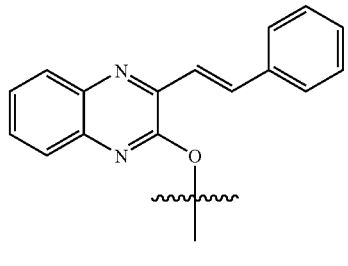
Q-51
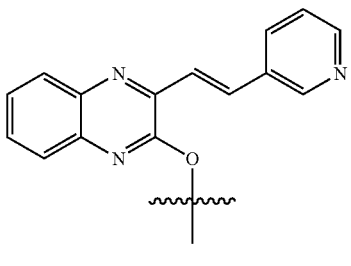
Q-52
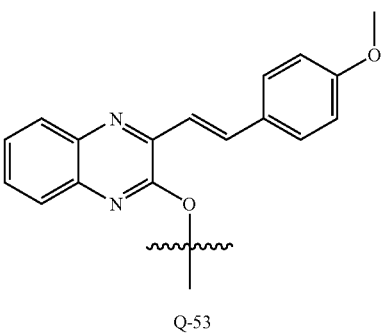
Q-53

TABLE 3-continued
Q-Matrix
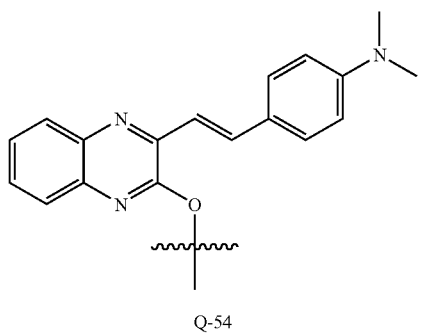
Q-54
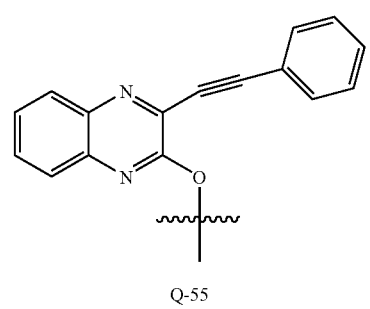
Q-55
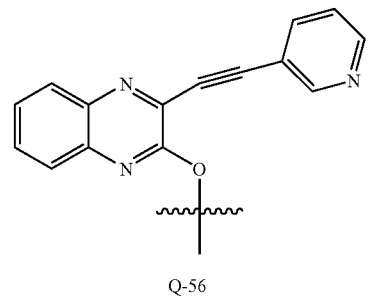
Q-56
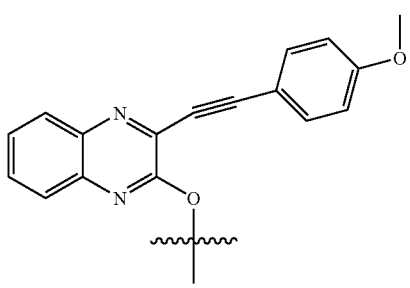
Q-57
TABLE 3-continued
Q-Matrix
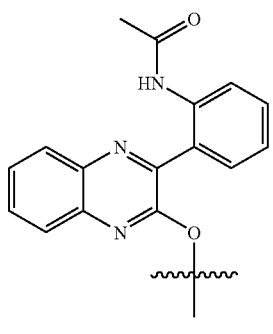
Q-58
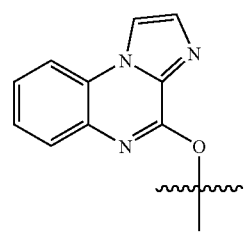
Q-59
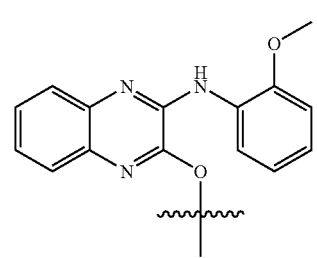
Q-60
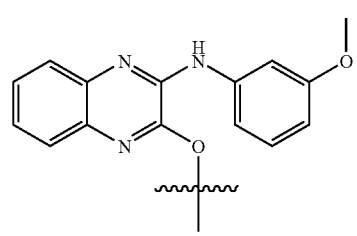
Q-61
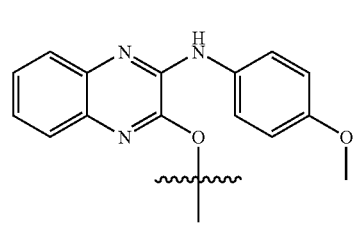
Q-62

TABLE 3-continued
Q-Matrix
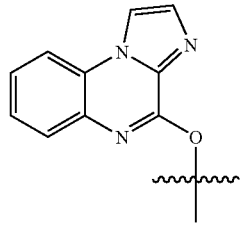
Q-63
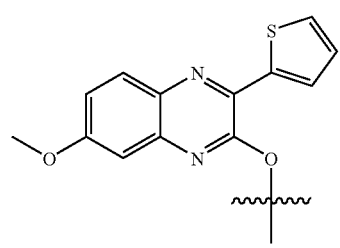
Q-64
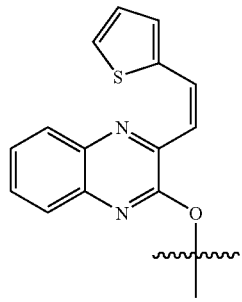
Q-65
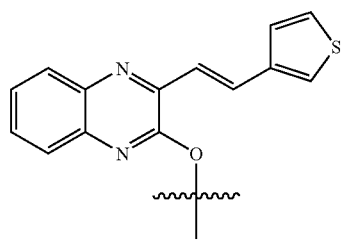
Q-66
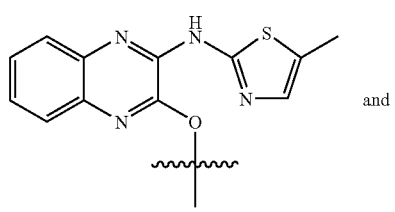
and
Q-67
TABLE 3-continued
Q-Matrix
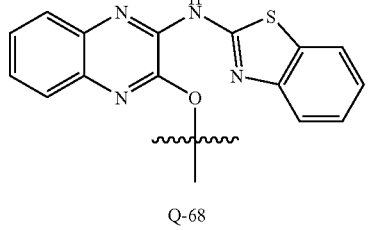
Q-68
TABLE 4
G-Matrix
—OH
G01
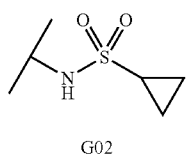
G02
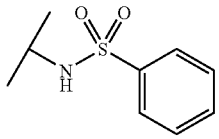
G03
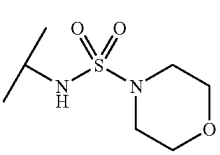
G04
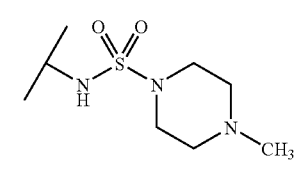
G05
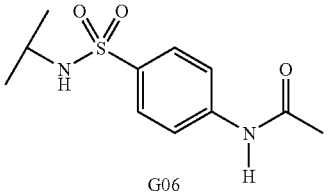
G06

TABLE 4-continued
G-Matrix
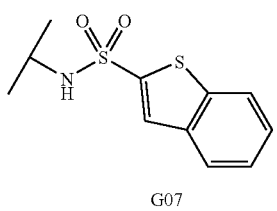
G07
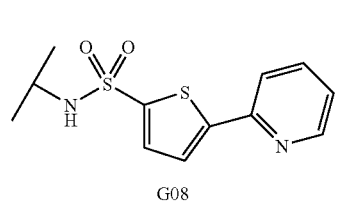
G08
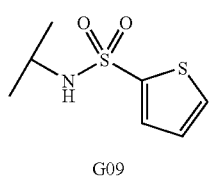
G09
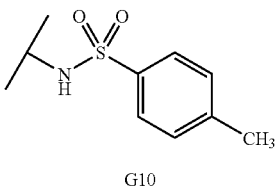
G10
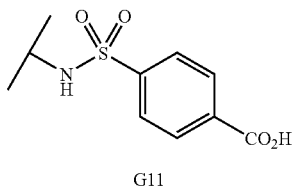
G11
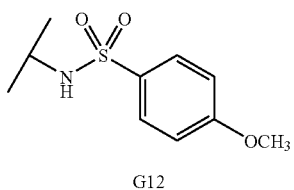
G12
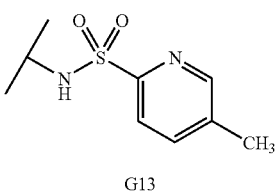
G13
TABLE 4-continued
G-Matrix
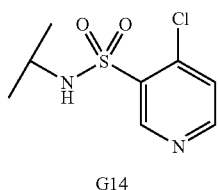
G14
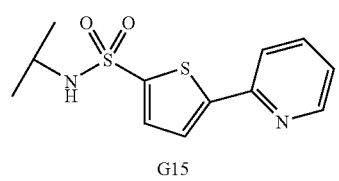
G15
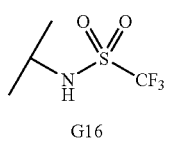
G16
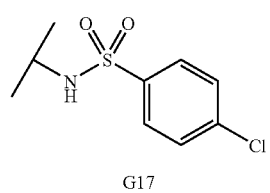
G17
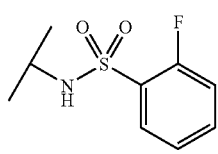
G18
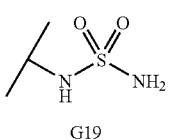
G19
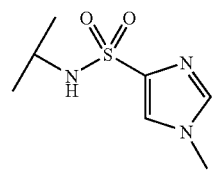
G20
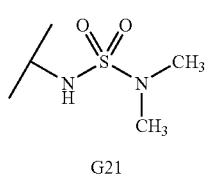
G21

TABLE 4-continued
G-Matrix
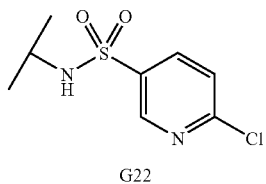
G22
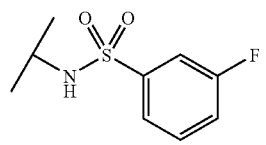
G23
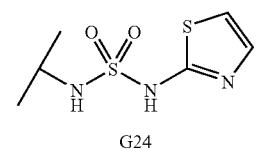
G24
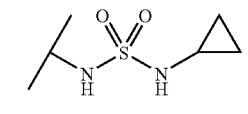
G25
TABLE 4-continued
G-Matrix
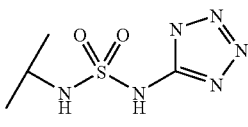
G26
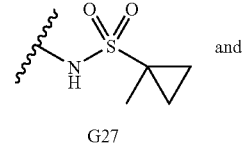
and
G27
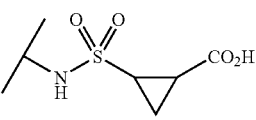
G28
5. A pharmaceutical composition comprising an inhibitory amount of a compound according to claim 1 or 4 alone or in combination with a pharmaceutically acceptable carrier or excipient.
* * * * *

UNITED STATES PATENT AND TRADEMARK OFFICE
CERTIFICATE OF CORRECTION

| | | |
|---|---|---|
| PATENT NO. | : 7,635,683 B2 | Page 1 of 1 |
| APPLICATION NO. | : 11/499917 | |
| DATED | : December 22, 2009 | |
| INVENTOR(S) | : Yonghua Gai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fifteenth Day of March, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,635,683 B2 | Page 1 of 1 |
| APPLICATION NO. | : 11/499917 | |
| DATED | : December 22, 2009 | |
| INVENTOR(S) | : Yonghua Gai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

This certificate supersedes the Certificate of Correction issued March 15, 2011.

Signed and Sealed this
Fourteenth Day of February, 2012

David J. Kappos
*Director of the United States Patent and Trademark Office*